(12) United States Patent
Li et al.

(10) Patent No.: US 9,908,934 B2
(45) Date of Patent: Mar. 6, 2018

(54) LUNG-TARGETING NANOBODIES AGAINST PULMONARY SURFACTANT PROTEIN A AND THEIR PREPARATION

(71) Applicant: SHANGHAI PULMONARY HOSPITAL, TONGJI UNIVERSITY SCHOOL OF MEDICINE, Shanghai (CN)

(72) Inventors: Huiping Li, Shanghai (CN); Shanmei Wang, Shanghai (CN)

(73) Assignees: Shanghai Pulmonary Hospital, Shanghai (CN); TONGJI UNIVERSITY SCHOOL OF MEDICINE, Shanghai (CN)

( * ) Notice: Subject to any disclaimer, the term of this patent is extended or adjusted under 35 U.S.C. 154(b) by 112 days.

(21) Appl. No.: 14/949,840

(22) Filed: Nov. 23, 2015

(65) Prior Publication Data

US 2017/0044242 A1   Feb. 16, 2017

Related U.S. Application Data

(62) Division of application No. 13/957,923, filed on Aug. 2, 2013, now Pat. No. 9,228,010.

(30) Foreign Application Priority Data

Apr. 17, 2013   (CN) .......................... 2013 1 0134673

(51) Int. Cl.
| | |
|---|---|
| *C07K 16/18* | (2006.01) |
| *C12N 5/10* | (2006.01) |
| *C12N 15/63* | (2006.01) |
| *C12N 15/64* | (2006.01) |
| *A61K 39/00* | (2006.01) |

(52) U.S. Cl.
CPC ........ *C07K 16/18* (2013.01); *A61K 2039/505* (2013.01); *C07K 2317/22* (2013.01); *C07K 2317/569* (2013.01)

(58) Field of Classification Search
CPC .............. C07K 16/18; C07K 2317/569; C07K 2317/22; C12N 5/10; C12N 15/63; C12N 2015/8518; C12N 15/64
See application file for complete search history.

(56) References Cited

U.S. PATENT DOCUMENTS 6,812,339 B1 * 11/2004 Venter .................. C12Q 1/6883
                                                    435/6.11
8,097,251 B2 *  1/2012 Muyldermans ........ C07K 16/18
                                                    424/133.1

FOREIGN PATENT DOCUMENTS

| CN | 102370620 A | 3/2012 |
| WO | WO 2004056311 A2 | 7/2004 |
| WO | WO 2007047922 A2 | 4/2007 |

OTHER PUBLICATIONS

Deffar, Khalissa et al. "Nanobodies—the new concept in antibody engineering", African Journal of Biotechnology, Jun. 17, 2009, vol. 8, No. 12, pp. 2545-2652.
International Search Report for corresponding PCT Application No. PCT/IB2013/001330, filed Jun. 24, 2013, dated Jan. 23, 2014.

* cited by examiner

*Primary Examiner* — Phuong Huynh
(74) *Attorney, Agent, or Firm* — Sheppard Mullin Richter & Hampton LLP

(57) ABSTRACT

The present invention relates to pharmaceutical and medical technologies, and more particularly to novel nanobodies against pulmonary surfactant protein A (SP-A) and their preparation methods. The nanobodies of the present invention comprises an amino acid sequence having certain formula. The present invention also relates to nucleic acid sequences encoding the nanobodies, their preparation method and their applications. Immunohistochemistry and in vivo imaging show that the nanobodies of the present inventions have high lung-targeting specificity.

5 Claims, 6 Drawing Sheets

LUNG-TARGETING NANOBODIES AGAINST PULMONARY SURFACTANT PROTEIN A AND THEIR PREPARATION

CROSS-REFERENCE TO RELATED APPLICATIONS

This application claims the benefit and priority of U.S. application Ser. No. 13/947,923, entitled "Lung-Targeting Nanobodies against Pulmonary Surfactant Protein A and Their Preparation," filed on Aug. 2, 2013, which is now U.S. Pat. No. 9,228,010 and claims the benefit and priority of Chinese Patent Application No. 201310134673.1, entitled "Lung-Targeting Nanobodies against Pulmonary Surfactant Protein A and Their Preparation," filed on Apr. 17, 2013. The entire disclosures of each of the above applications are incorporated herein by reference.

SEQUENCE LISTING

The instant application contains a Sequence Listing which has been submitted in ASCII format and is hereby incorporated by reference in its entirety. Said ASCII copy, created on Aug. 30, 2013, is named 35JK-178791_SL.txt and is 115,422 bytes in size.

TECHNICAL FIELD

The present invention relates to the field of biochemistry and pharmaceutical technologies, particularly to nanobodies that bind to pulmonary surfactant protein A (SP-A) with specificity.

BACKGROUND OF THE INVENTION

In the beginning of 20th century, the Nobel Prize-winning German scientist Paul Ehrlich proposed the idea of "magic bullet" for future drug development, i.e., an ideal drug that would selectively destroy diseased cells without affecting healthy cells. In the past several decades, scientists have been exploring to develop such ideal drugs.

In the 1970s, targeted drug delivery system was developed and widely used for the treatment of cancer. It was reported that targeted anti-cancer drugs accounted for more than 30% of the world's anti-cancer drug sales, and that this figure is forecasted to rise to 55% in 2025. Meanwhile, with the advancement in research, new targeted drug delivery carriers has emerged, the routes of administration has been broadened, and targeted drug delivery system has been expanded to treat many diseases other than cancer.

Developing targeted drugs for respiratory diseases is one of the hotspots of the research, which is primarily focused on the following areas:

1. Targeted treatment of airways diseases by inhalation. Starting from the earlier 1950s, inhaled corticosteroids have been used for the treatment of asthma and COPD. Since then, with improvement in inhaled drugs and devices, inhaled corticosteroids have become the main therapeutic agents for the treatment of asthma and COPD. However, inhaled drugs are mainly suitable for topical treatment of airways diseases, and are not effective against parenchyma and interstitial lung diseases due to low bioavailability.

2. Passive lung-targeting drugs through drug carriers. Currently, a variety of drug carriers such as liposomes, microparticles, microspheres have been researched for lung-targeted drug delivery. However, these passive targeting drugs have poor tissue selectivity, and cannot avoid significant residue in the liver, spleen and other organs. Therefore, they don't achieve optimal targeting effect.

The ligand-receptor or antigen-antibody binding is a special recognition mechanism of the human body, and as reported in the literature, this mechanism can achieve active drug targeting to enhance drug efficacy and reduce the side effects. For example, a composite drug made of paclitaxel liposome and a monoclonal antibody against the epidermal growth factor has anti-tumor effect that is 25 times greater that of the drug without the monoclonal antibody. Thus, to achieve ideal active lung targeting effect, it is critical to find a receptor in the lung tissue with high specificity and prepare a targeting ligand with high affinity. Studies have shown that pulmonary alveolar type II epithelial cells in the lung tissue have proliferation and secretion functions, and account for 16% of the total cells in lung parenchyma. Type II cells can synthesize and secrete pulmonary surfactant. The main components of the pulmonary surfactant are lipids (90%) and proteins (10%), and the proteins are specific pulmonary surfactant proteins (SP). SP has been named as SP-A, SP-B, SP-C, SP-D, SP-A based on the order it was discovered, and SP-A was discovered first, and has strong expression in pulmonary alveolar type II epithelial cells with abundant signals, and is rarely expressed in other tissues. Thus, SP-A is highly lung-specific, and is an ideal receptor in the lung tissue with specificity.

In addition to high affinity, an ideal targeting ligand should also have a small molecular weight, high tissue penetration, and weak immunogenicity. Antigen-antibody binding is the strongest recognition mechanism, and therefore antibody is the preferred ligand. However, although of high affinity, full antibodies have large molecular weight (with a relative molecular weight of 150,000), weak tissue penetration and strong immunogenicity, and are not ideal ligands. With the development of antibody and gene engineering technologies, antibody fragments (Fab, ScFv) now have the advantages of small molecular weight and weak immunogenicity, but they has lower stability and affinity than full antibodies.

In 1993, scientists from Belgian first reported the existence of Heavy Chain antibody (HCAbs) without the light chain in the blood of camelids. The variable domain (VHH) of the heavy chains of HCAbs has a complete and independent antigen-binding capacity, and if cloned, a single domain antibodies in the nanometer scale can be obtained, which are known as Nanobodies® (Nbs). Nanobody has many advantages as a ligand: 1) small molecular weight, strong tissue penetration, and high affinity. It has the least molecular weight among the known antibody molecules, with a molecular weight of only 15,000; its ability to penetrate tissues is significantly superior to full antibody, and its affinity with specific antigen is of nmol scale. 2) Stable structure. It can maintain high degree of stability even if stored at 37° C. for a week, under high temperature (90° C.), or under strong denaturing conditions such as being exposed to chaotropic agent, protease and strong PH value. 3) Weak immunogenicity. AS its gene has high homology with human VH III family, it has weak immunogenicity and good biocompatibility. Because of these advantages, nanobody has been studied extensively as a new antibody drug, but its use as targeted ligand for SP-A has not been reported.

SUMMARY OF THE INVENTION

The present invention provides lung-targeting nanobodies and their applications.

SP-A was the first discovered pulmonary surfactant protein, has strong expression in pulmonary alveolar type II epithelial cells with abundant signals, and is rarely expressed in other tissues. SP-A is highly lung-specific, and is an ideal lung-specific receptor. In accordance with embodiments of the present invention, alpacas was immunized with SP-A, an antibody library was built, affinity selection was employed to screen and identify genes with lung-targeting specificity, and SP-A nanobodies with high affinity was obtained by prokaryotic expression. In vivo and in vitro experiments were conducted to verify that the nanobody has high specificity for targeting lung tissue.

In accordance with an embodiment of the present invention, a lung-targeting nanobody, called SPA-Nb, is provided. The nanobody comprises an amino acid sequence having the formula of $Q(x)_2LVESGG(x)_2V\ (x)_2G(x)\ SL(x)\ LS(x)_{24}E\ (x)_{n2}KG(x)_4S(x)_{n3}T(x)_2Y(x)\ C(x)_{n4}S(x)_{n5}V(x)_{n6}R$; wherein x is any amino acid; $1 \le n2 \le 21$; $1 \le n3 \le 19$; $1 \le n4 \le 50$; $1 \le n5 \le 22$; $1 \le n6 \le 8$.

Preferably, $17 \le n2 \le 21$; $18 \le n3 \le 19$; $16 \le n4 \le 50$; $17 \le n5 \le 22$; $7 \le n6 \le 8$.

For example, the nanobody comprises an amino acid sequence of MQAQLAGQLQ LVESGGGLVQ PGGSLRLSCV xSGTISxYGM GWxRQAPGKG RExVSTIxSx GxTxxxxYYA DSVKGRFTIS RDNAKNTLYL QMNSLKPEDT AxYYCxLxGx xxxxxxxxxx xxxxxxxxxH RGQGxxxxxx xxxTQVTVSS xxEPKTPKPQ GPRGLAAAGA PVPYPDPLEP RAA (SEQ ID NO 69), wherein x is any amino acid.

In accordance with another embodiment of the present invention, the nanobody comprise an amino acid sequence having the formula of $Q\ (X_1)LVESGG(X_2)V(X_3)G\ (X_4)SL\ (X_5)\ LS(X_6)\ E\ (X_7)\ KG(X_8)\ S(X_9)\ T(X_{10})\ Y(X_{11})\ C(X_{12})\ S(X_{13})\ V(X_{14})R$, wherein $X_1$ is selected from a group consisting of LQ and VK;

$X_2$ is selected from a group consisting of GS, GL, GR, GM, RL and GT;

$X_3$ is selected from a group consisting of is QA, QP, QI, AP and EV;

$X_4$ is selected from a group consisting of R, G and E;

$X_5$ is selected from a group consisting of K, N, R, M and T;

$X_6$ is selected from a group consisting of CTASGSDYRWMYIARFRQCPGKER, CAASGRAFSVYAVGWYRQIPGNQR, CTASETTFEIYPMAWYRQAPGKQR, CAASGSDFSIYHMGWYRQAPGKQR, CAASGDIFTLASMGWYREDLHKKR, CEASGFTFDDYAIGWFRQAPGKER, CVALGFTLDGYAIGWFRQAPGKER, CTASKFHLDSYAVAWFRQTPGKER, CVVSGVTISNYGMTWVRQAPGKGL, CVVSGVTFNNYGMTWVRQAPGKGL, CVTSGFTFSRHDMSWVRQAPGKGP, CAASGFIFSRYDMGWVRQTPGKGR, CAASGIILNFYGMGWDRQTPGQGL, CTASEFTLDYHSIGWFRQAPGKER, CAASGRAFSVYAVGWYRQPPGKQR, CEVSGSRGSIYFSGWYRQAPGKQR, CVASGSMFNFYGMAWYRQAPGKQR and RTFSGLYLHSSAFGWFPHVPREAR;

$X_7$ is selected from a group consisting of GVAAIYTDDTDDSSPIYATSA, MVAAISSGGNTKYSDSV, LVAGINMISSTKYIDSV, LVAAITSGGSTNYADSV, LVAQLMSDGTANYGDSV, EVSCISHNGGTTNYADSV, KISCISSTGDSTNYDDSV, AVSFINTSDDVTYFADSV, WISTIYSNGHTYSADSV, WISSIYSNGHTYSADSV, WISGIGTSGTSGRYASSV, WVSGINSGGGRTYYADSV, GVSYVNNNGMTNYADSV, GVSCISYGDGTTFYTDSV, LVASITDGGSTNYADSV, LVASITSGGTTNYADSV, LVASIDSEGRTTNYPDSL and GVAFLCNSGSDPIYLHPE;

$X_8$ is selected from a group consisting of RFTI, RVTI, RFSI, RFTA, RFTV and IFTL, $X_9$ is selected from a group consisting of QDKDKNAVYLQMNSPKPED, RDNDKNTMYLQMNSLKPED, SDNAKNTVYLQMNSLKPED, RDDVDTTVHLRMNTLQPSD, RDNAKNTVYLQMNGLKPED, RDTAKSTVFLQMNNLIPED, RDNSKNTVYLQMNVLKPED, RDNANNTLYLQMNSLKPED, RDNAKNTLYLQMISLKPED, RDNAKDTLYLQMDSLKPED, RDDDKATLYLSMDGLKPED, RDNAKNTMYLQMNSLKPED, RDNAKNTVTLQMNSLKPED, RDNARNTAYLDMNSLKVED, RDNAKNTVYLQMNSLKPED, RDDAKSTAYLQMNNLIPDD, RHCVKTVSPFEDNDTVEH, RDNAKNTLYLQMNSLKPED and NULL;

$X_{10}$ is selected from a group consisting of PT, AV, AD, AL, GL, AK, AN, AI, SV, GE, AM and NULL;

$X_{11}$ is any amino acid or NULL;

$X_{12}$ is selected from a group consisting of AARAFGGTWSLSSPDDFSAWGQGTQVTVS, NLDTTMVEGVEYWGQGTQVTVS, NADGVPEYSDYASGPVYWGQGTQVTVS, YIHTSREITWGRGTQVTVSQGESSAPQSSAPQATVS, AGARSGLCVFFELQDYDYWGQGTQVTVS, GADLLARCGRVWYFPPDLNYRGQGTQVTVS, AAVRSPGPTGPSMQPMWSVPDLYDYWGQGTQVTVS, KLTGETHRGQGTQVTVS, KLVGETHRGQGTQVTVS, RLTGETYRGQGTQVTVS, TTGGVYSAYVQPRGKGTQVTVS, VRFTVKTPQGYYYLNDFDYWGQGTQVTVS, NVSAYTYRSNYYYPWGQANHVTVS, AASPGRLLLFRLCMSEDEYDFWGQGTQVTVS, NANYGGSVLYNYWGPGTQVTVS, NIGRYGLGGSWGQGTQVTVS, NAFRGRMYDYWGQGTQVTVS, PTHLVITHPCICIPSAMDYRGKGTLVPLS and NULL;

$X_{13}$ is selected from a group consisting of STNEVCKWPPRPCGRRCAGA, SHHSEDPGPRGLAAAGAP, SEPKTPKPQGPRGLAAAGAP, TEPKTPKPQGPRGLAAAGAP, SKPTTPKPRAPKALRPQ, SAHHSEDPGPRGLAAAGAP and SQRKTRKAQGRARLADAGAP;

$X_{14}$ is selected from a group consisting of PYPDPLEP, SGSAGTAC, PHADQMEQ and PRCRIRF。

NULL means there is no amino acid at this position.

Preferably, $X_{11}$ is selected from a group consisting of Q, Y, H, V and F.

In accordance with another embodiment of the present invention, the nanobody comprises an amino acid sequence comprising any of SEQ ID NOs 37 to 67.

The present invention also provides nucleic acids encoding the lung-targeting nanobody.

In accordance with an embodiment of the present invention, the nucleic acid comprise a polynucleotide sequence comprising any of SEQ ID NOs 1 to 36.

The nanobody of the present invention can be used as lung-targeting ligand specifically targeting pulmonary surfactant protein A (SP-A).

In accordance with another embodiment of the present invention, a method of preparing the nanobody is provided; the method comprises the steps of:

(a) immunizing an alpacas using pulmonary surfactant protein A (SP-A);

(b) selecting and obtaining gene sequences with a high affinity with SP-A; and (c) inducing the expression of the obtained gene sequences.

Preferably, the step (b) comprises affinity selection.

In accordance with an embodiment of the present invention, high purity pulmonary surfactant protein A (rSP-A) was prepared using gene synthesis and prokaryotic expression, and used to immunize alpaca; an alpaca antibody library was built by the isolation of peripheral blood lymphocytes, RNA extraction, cDNA synthesis, and gene amplification; the library had a capacity of 31 5.7×106 cfu. Through affinity selection and indirect phage ELISA, 31 clones with high affinity with rSP-A were finally obtained. Sequencing analysis showed they were all VHH sequences (nanobody sequences).

Nb6 and Nb17 had the highest affinity, and were selected as the preferred embodiments for prokaryotic expression to obtain nanobodies with a molecular weight of about 170,000 and a size of nanometer scale. In in vitro Western Blot and ELISA experiments, Nb6 and Nb17 showed good affinity with rSP-A, immunohistochemistry and in vivo imaging results showed that had lung-targeting specificity as they can bind to natural SP-A in the lung tissue.

In accordance to an embodiment of the present invention, synthetic method was used to obtain the polypeptide of the nanobody.

To further optimize the nanobody of the present invention, the active region of the polypeptide sequences of the selected clones were tested. Testing results showed that the functional polypeptides of Nb6 and Nb17 (without the MQAQKAG part) have good lung-targeting specificity.

To further verify that the 31 nanobody sequences all have lung-targeting affinity with rat pulmonary surfactant protein A, respectively, 21 clones (excluding those with the same sequence with Nb17) were expressed and purified, all proteins were obtained through soluble expression, with Nb1 had the least expression level of 3 mg/L, while the rest had an average protein expression level of 8 mg/L.

In Western blot and ELISA analysis, all 21 expressed proteins had clear affinity, where 7 nanobodies, namely Nb9, Nb11, Nb18, Nb19, Nb36, Nb32, and Nb48 had OD450 values 5 times greater than the negative control group.

Immunohistochemical staining also showed that these clones had strong affinity. All clones showed significant differences with the negative control group.

In vivo testing showed that 7 nanobodies, namely Nb9, NB11, NB18, NB19, Nb36, NB32, and Nb48 had targeting effect similar to that of Nb17; though their clustering levels vary, all the images showed significant clustering in the lung.

Similarly, functional polypeptides were synthesized using Nb18 and Nb36 as representative examples (Nb36 was without the MQAQLAV at the N-end, NB18 was without MQAQKAG at the N-end). Western blot and immunohistochemical showed that affinity was not affected.

The present invention provides a nanobody (SPA-Nb) against rat pulmonary surfactant protein A (SP-A). Tests showed that the SPA-Nb of the present invention had high lung-targeting specificity.

In accordance with embodiments of the present invention, the SPA-Nb coding sequence refers to the nucleotide sequence of the SPA-Nb polypeptide, such as the sequences from SEQ ID NO 37 to SEQ ID NO 67 and its degenerate sequence. The degenerate sequence refers to sequences from SEQ ID NO 37 to SEQ ID No. 67 wherein one or more codons were substituted.

The SPA-Nb coding sequences also include variants of SEQ ID NO 37 to SEQ ID No. 67 that encoding proteins with the same functions as SPA-Nb. Such variants include (but are not limited to): the deletion, insertion or substitution of a plurality (usually 1-90, preferably 1-60, more preferably 1-20, most preferably 1-10) of nucleotides, and the adding at the 5' and/or 3' end of a plurality of (typically less than 60, preferably less than 30, more preferably less than 10, the top for 5 or less) nucleotides.

Once the SPA-Nb coding sequence is obtained, large quantities of the recombinant sequences can be obtained. This is usually done by cloning the sequence into a vector, and transferred to the cells, then using conventional methods to isolate the sequences from the proliferated host cell.

In addition, the sequences can also be obtained by synthetic methods, as the length of the inhibitory factor of the nanobodies of the present invention is short. Typically, a number of small fragments can be synthesized first, and a long fragment can be formed by linking the small fragments.

In accordance with the present invention, various forms of vectors known in the art, such as those that are commercially available, can be used. For example, using a commercially available vector, the nucleotide sequence encoding the polypeptide of the invention can be operably linked to expression control sequence to form a protein expression vector.

As used herein, the term "operably linked" means the situation where part of the DNA sequence can affect the activity of other part of the DNA sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase.

In accordance with embodiments of the present invention, the term "host cell" includes prokaryotic cells and eukaryotic cells. Examples of commonly used prokaryotic host cells include *Escherichia coli, Bacillus subtilis*, etc. Commonly used eukaryotic host cells include yeast cells, insect cells, and mammalian cells. Preferably, the host cell is a eukaryotic cells, such as CHO cells, COS cells and the like.

The antibodies of the present invention can be prepared by various techniques known to those skilled in the art. For example, purified SP-A, or its antigenic fragments can be administrated to animals to induce the production of antibodies. Similarly, cells expressing SP-A or its antigenic fragments can be used to immunize animals to produce antibodies. Antibodies in the invention can be produced by routine immunology techniques and using fragments or functional regions of SP-A gene product. These fragments and functional regions can be prepared by recombinant methods or synthesized by a polypeptide synthesizer. Antibodies binding to unmodified L SP-A gene product can be produced by immunizing animals with gene products produced by prokaryotic cells (e.g., *E. coli*); antibodies binding to post-translationally modified forms thereof can be acquired by immunizing animals with gene products produced by eukaryotic cells (e.g., yeast or insect cells).

The invention also relates to nucleotide sequences or nucleic acids that encode amino acid sequences, fusion proteins and constructs described herein. The invention further includes genetic constructs that include the foregoing nucleotide sequences or nucleic acids and one or more elements for genetic constructs known per se. The genetic construct may be in the form of a plasmid or vector.

The invention also relates to hosts or host cells that contain such nucleotide sequences or nucleic acids, and/or that express (or are capable of expressing), the amino acid sequences, fusion proteins and constructs described herein.

The invention also relates to a method for preparing an amino acid sequence, fusion protein or construct as described herein, which method comprises cultivating or maintaining a host cell as described herein under conditions such that said host cell produces or expresses an amino acid sequence, fusion protein or construct as described herein, and optionally further comprises isolating the amino acid sequence, fusion protein or construct so produced.

The invention also relates to a pharmaceutical composition that comprises at least one amino acid sequence, fusion protein or construct as described herein, and optionally at least one pharmaceutically acceptable carrier, diluent or excipient.

Thus, in another aspect, the invention relates to a method for the prevention and/or treatment of lung disease or disorder that can be prevented or treated by the use of a fusion protein or construct as described herein, which method comprises administering, to a subject in need thereof, a pharmaceutically active amount of a fusion protein or construct of the invention, and/or of a pharmaceutical composition comprising the same. The diseases and disorders that can be prevented or treated by the use of a fusion protein or construct as described herein will generally be the same as the diseases and disorders that can be prevented or treated by the use of the therapeutic moiety that is present in the fusion protein or construct of the invention.

The present invention provides nanobodies that bind to pulmonary surfactant protein A (SP-A) with specificity. In accordance with embodiments of the present invention, alpacas was immunized with SP-A, gene sequences with high affinity with rSP-A were obtained by constructing an alpacas antibody library and affinity selection, and nanobodies with high affinity and small molecule weight were obtained by induced expression of the gene sequences through a prokaryotic expression vector. Immunohistochemistry and in vivo imaging in rat showed the nanobodies have high specificity for targeting lung tissue. By providing nanobodies with lung-targeting specificity, the present invention provides tools for further research on lung-targeting ligands for targeted drug delivery for lung diseases.

DESCRIPTION OF THE PREFERRED EMBODIMENTS

The present invention is further illustrated using the following embodiments, but any of the embodiments or its combinations thereof should not be construed as a limitation to the scope of the present invention. The scope of the present invention is defined by the appended claims, which can be clearly understood by those skilled in the art by reference to this specification and general knowledge in the art. Without departing from the spirit and scope of the present invention, modifications or changes can be made to the present invention by those skilled in the art, and such modifications and changes are also within the scope of the present invention.

Example 1. The Preparation and Testing of Rat Pulmonary Surfactant Protein A (rSP-A)

1.1 the Preparation of Rat Pulmonary Surfactant Protein A (rSP-A)

Figure 1A:
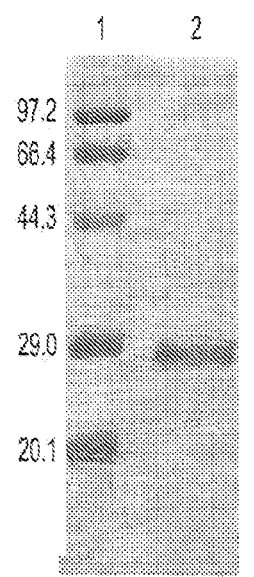
FIG. 1A is SDA-PAGE for rSP-A: 1 Mark; 2, rSP-A.

The protein coding sequence (CDS) of rSP-A gene sequence (*Rattus norvegicus* Sftpa, 1) was searched from the NCBI gene library. Artificial gene synthesis was performed, the sequence was tested and verified, prokaryotic expression vector was constructed, and the rSP-A was expressed from inclusion bodies having a molecular weight of 26,000. The rSP-A was purified by nickel affinity chromatography and dialysis refolding, and made into dry powders by freezing. (FIG. 1A).

1.2 rSP-A Testing 1.2.1 Western Blot Testing

Figure 1B:
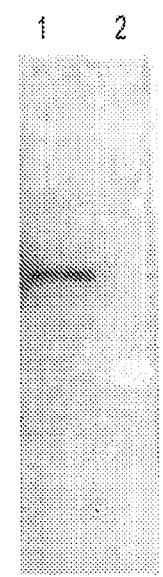
FIG. 1B is Western blot of rSP-A: 1, rSP-A; 2, Mark.

Purified rSP-A was isolated by SDS-PAGE and transferred onto nitrocellulose membrane. It was sealed in 5 g/L skim milk and incubated for 2 hours, then immune serum containing rabbit polyclonal antibody against rSP-A (at room temperature for 2 hours, and washed 3 times with PBS) and serum containing goat anti-rabbit IgG-HRP (at room temperature for 1 hours, washed 3 times with PBS) were added sequentially. DAB was added last to develop the image, and photographs of the image were taken. The photographs contain a single stripe with a molecule weight of 26 Kd (FIG. 1B).

1.2.2 ELISA Test

Figure 1C:
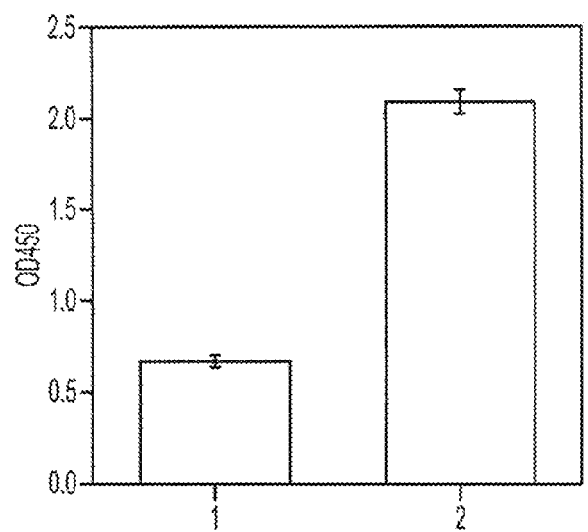
FIG. 1C is ELISA: 1. negative protein; 2, rSP-A.

ELISA test was performed to measure the immunological activity of the purified protein. An ELISA plate with 96 wells were coated with purified rSP-A and an unrelated protein (GST), and incubated overnight at 4° C. The next day, it was sealed in 3% skim milk and incubated at 37° C. for an hour, then immune serum containing rabbit polyclonal antibody against rSP-A (at room temperature for 2 hours, and washed 3 times with PBS) and serum containing goat anti-rabbit IgG-HRP (at room temperature for 1 hours, washed 3 times with PBS) were added sequentially. DAB was added last to develop the image, and sulfuric acid was added to stop the reaction. The OD value of each well was measured using the chromogenic microplate, which showed that, compared with the control group, both purified rSP-A and SP-A polyclonal antibody had obvious binding activity (FIG. 1C).

1.2.3 Protein Spectrum Analysis

Spectrum analysis was performed on dry rSP-A powder obtained through freezing, and the results shown its sequence was the exactly the same as the original gene sequence.

Example 2. Alpaca Immunization and Test for Immunization Effect 2.1 Alpaca Immunization The prepared rSP-A and an equal volume of Freund's complete adjuvant were emulsified, and injected subcutaneously into an alpaca at multiple points of the neck and limbs. The immunization dose is 1 mg each time. Afterwards, every two weeks, the same dose was mixed with Freund's incomplete adjuvant and injected 5 more times. 10 ml of peripheral blood was collected before each immunization and 14 days after the immunization. The serum was separated for antibody titer. Also, the serum collected before the immunization was purified and isolated for the preparation of polyclonal rabbit anti-alpaca IgG antibody.

2.2 Preparation of Polyclonal Rabbit Anti-Alpaca IgG Antibody Serum

Purified alpaca IgG was mixed with Freund's complete adjuvant, and injected subcutaneously into New Zealand white rabbits at multiple points of the back. The immunization dose is 200 µg each. Afterwards, every week, half of the original dose was mixed with Freund's incomplete adjuvant, and injected into the rabbits four more times. The peripheral blood was collected 14 days after the end immunization. The serum was separated, and HRP marking was performed. The serum was stored at 50° C.

2.3 Testing of rSP-A Antibody Level in Alpaca Serum

ELISA was used to test the change of in goat anti-alpaca rSPA antibody level in the prepared rabbit anti-alpaca serum. The results showed that the antibody titer after 4 immunizations was maintained at 1:10,000.

Example 3. Construction and Verification of Alpaca Antibody Library 3.1 Total RNA Extraction from Peripheral Blood Lymphocytes and cDNA Synthesis 200 ml alpaca peripheral blood was collected 14 days after the immunization, lymphocytes were separated and the total RNA was extracted using the single-step method with Trizol Reagent. Measured by the Nanodrop Spectrophotometer, its concentration was 1205 ng/ul, and OD260/OD280 is 1.82. Three stripes were visible through 1% agarose gel electrophoresis at 28S, 18S and 5S RNA respectively, wherein the 28S RNA stripe was brighter than the 18S RNA stripe, which meant that the total RNA was fairly complete, and suitable for cDNA synthesis.

3.2 VHH Gene Amplification and Restriction Digestion 3.2.1 Design of Primer for Gene Amplification and Amplification Procedure cDNA product was used as the template, and VHH-LD primer and CH2-R were used for the first PCR amplification. All the reagents were 50 ul. The PCR product of VHH gene fragments was tested with a 1.5% agarose gel electrophoresis, and cut out of the gel under ultraviolet light. The extracted fragments were purified by gel extraction kit, and the resulted purified fragments were then used as the template for the second PCR reaction. Two sets of primers were used for PCR amplification of two heavy chain antibody VHH gene fragments. The primers were designed as follows:

| Primer | Seqence Listing |
|---|---|
| VHH-LD | CTTGGTGGTCCTGGCTGC (SEQ ID NO 1) |
| CH2-R | GGTACGTGCTGTTGAACTGTTCC (SEQ ID NO 2) |
| ALP-Vh-SfiI | CCGTGGCCAAGCTGGCCGKTCAGTTGCAGCTCGT GGAGTCNGGNGG (mixed primers: K: G or T; N: A, T, G, C) (SEQ ID NO 3) |
| VHHR1-SfiI | CCGTGGCCTCGGGGGCCGGGGTCTTCGCTGTGGTGCG (SEQ ID NO 4) |
| VHHR2-SfiI | CCGTGGCCTCGGGGGCCTTGTGGTTTTGGTGTCTTGGG (SEQ ID NO 5) |

3.3 Restriction Digestion of PCR Product and Construction of VHH Antibody Library 3.3.1 Restriction Digestion of PCR Products and Phagemid pCANTAB 5E Carrier The above PCR products and phagemid pCANTAB 5E carrier were digested by Sfi I restriction enzyme.

3.3.2 Ligation of Phagemid Vector pCANTAB 5e and VHH Gene

After digestion by Sfi I restriction enzyme, the phagemid pCANTAB 5E vector and gene fragment were purified and quantified, and ligation reaction was performed at a mass ratio of 1:3 in water at 16° C. for 14 hours.

3.3.3 Construction of VHH Antibody Library

The ligation product was transformed into *E. coli* TG1, and 1 ul of transformed solution was plated. 280 positive growing clones were obtained the following day. 20 clones were randomly chosen for bacilli propagation and sequencing. The results showed that 19 clones contained the construct sequence, and most of the sequences were different. It can be determined that VHH recombinant fragment insertion rate was about 95%. The antibody library has good diversity. It was calculated the VHH antibody library's capacity was approximately $2.66 \times 10^5$ cfu.

3.3.4 Propagation of M13KO7 Helper Phage Propagation and Titer Measurement

M13KO7 helper phage was inoculated in 2YT solid medium. Well separated plaques were chosen for propagation. Phage solution was diluted in 1:10, 1:100, 1:1000 and so on, and titer measurements were taken.

The phage titer was calculated as $3.8 \times 10^{15}$ pfu, using the number of plaques times dilution factor times 10.

3.3.5 the Expression and Isolation of VHH Phage Antibody Library

The VHH antibody library constructed with M13KO7 helper phage with a titer measurement of $10^{15}$ pfu was used to obtain the VHH phage library through precipitation with 20% PEG8000-NaCl, settlement with sterile PBS suspension, and separation of the recombinant phage particles. The capacity of the VHH phage library was measured, and the VHH phage library had a titer of $3.5 \times 10^{12}$.

Example 4. Screening of rSPA-Specific Nanobody (rSPA-Nb)

Affinity selection technique was employed to screen the VHH antibody library with rSP-A.

4.1 Simplified Procedure of Affinity Selection:

(1) The immunization tubes were coated with rSP-A, and incubated at 4° C. overnight.

(2) The tubes were washed 3 times using PBS, and dried by shaking.

(3) The tubes were blocked using 3% MPBS (3% skim milk added to PBS) and incubated for 2 hours at 37° C. The blocking solution was poured, and the tubes were washed 3 times using PBS, and dried by shaking.
(4) 2 mL of the prepared phage library was added to each immunization tubes, and incubated for 30 minutes with gentle shake, and incubated for 1.5 hours without shaking.
(5) The phage library in the tubes was disposed, and the tubes were washed three times with PBS, and dried by shaking.
(6) The host strain TG1 was added to wash away the bound phage library. This completed the first round of selection, and the first antibody library was obtained. The output of the antibody library was calculated.
(7) The selection steps were repeated for 3 times to obtain the third antibody library.

4.2 Preliminary Selection of Positive Nanobodies Using Indirect Phage ELISA.
(1) Single clones obtained from the three rounds of selections and grown on 2YTAG plates were inoculated into the 72-well culture plate at 30° C., and cultured with shaking overnight.
(2) 400 ul of M13K07 helper phage was put in each well of another 72-well culture plate (labeled P1 Plate) the next day.
(3) 40 ul of cultured medium were taken from each well of the Master Plate, which was cultured overnight, and put in each well of the P1 Plate, and incubated at 37° C. with shaking overnight. The culture supernatant was prepared by centrifugation at 1500 g for 20 minutes set aside, and the recombinant antibody was obtained.
(4) A 96-well microtiter plate was coated with rSP-A.
(5) 160 ul of recombinant antibody was mixed with 40 μL of MPBS, incubated for 20 minutes at room temperature. It was then added to blocked microtiter wells and reacted for 2 hours at 37° C.
(6) Washing and adding HRP secondary antibody: HRP-labeled antibody against M13K07 was diluted 1:4000 in PBS, 200 ul of that was added to each well, and incubated and reacted for 1 hour at 37° C.
(7) 200 ul TMB substrate solution was added to each well, incubated at 37° C. for about 45 minutes to develop the image, 100 ul of stop solution was added to each well to stop the development process, and measurements were taken at 450 nm. Preliminary screening was conducted to select positive clones binding to rSP-A with specificity. If a clone has affinity value greater than 3 times the affinity value for the negative control great, then it is considered to be a positive clone.

Preliminary screening by indirect Phage ELISA showed that 31 sequences had affinity value greater three times the affinity value for the negative control group, and these 31 sequences were positive clones.

Figure 2A:
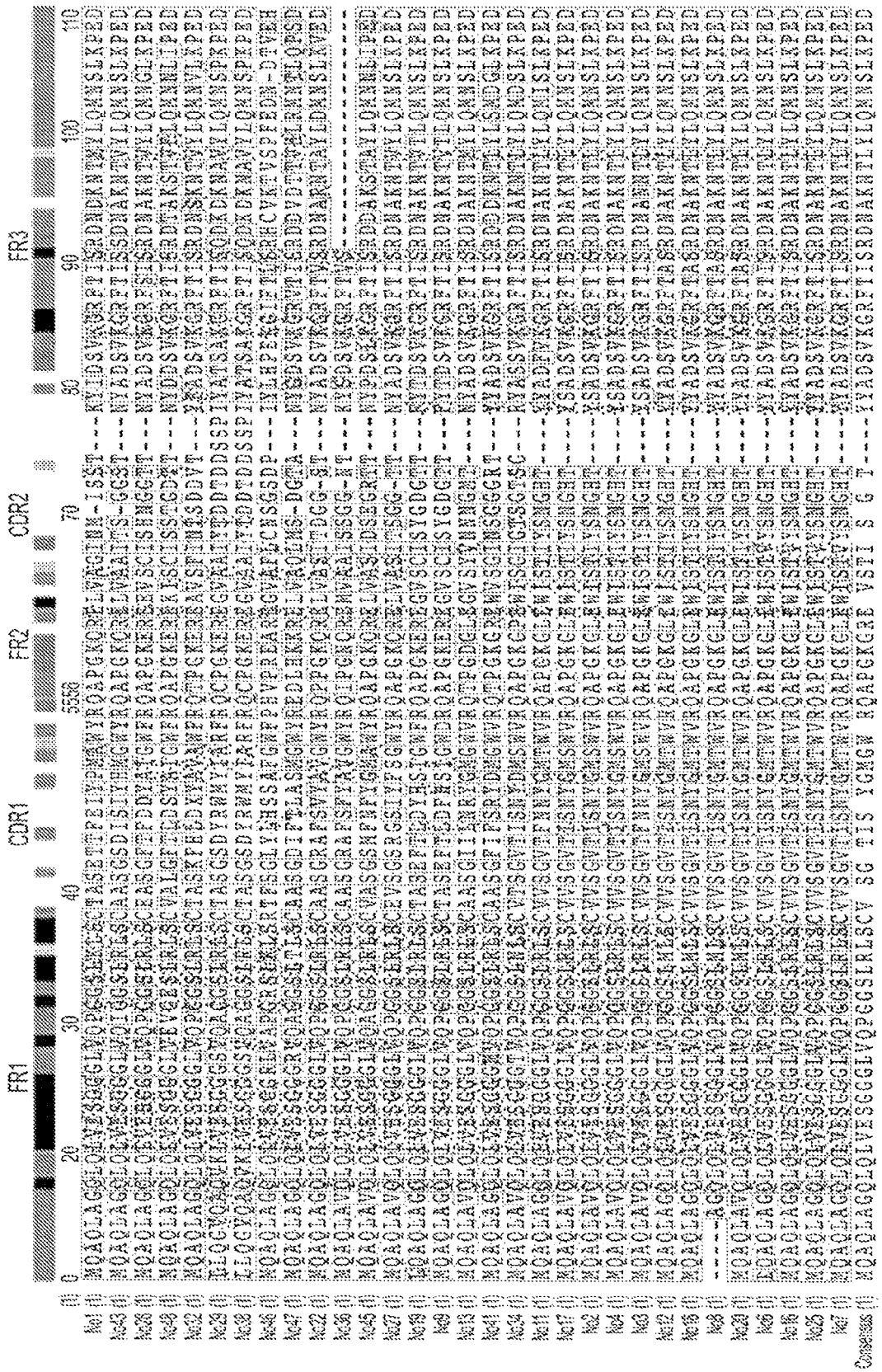
FIG. 2A is a diagram showing the comparison of the coding sequences of the clones.
Figure 2B:
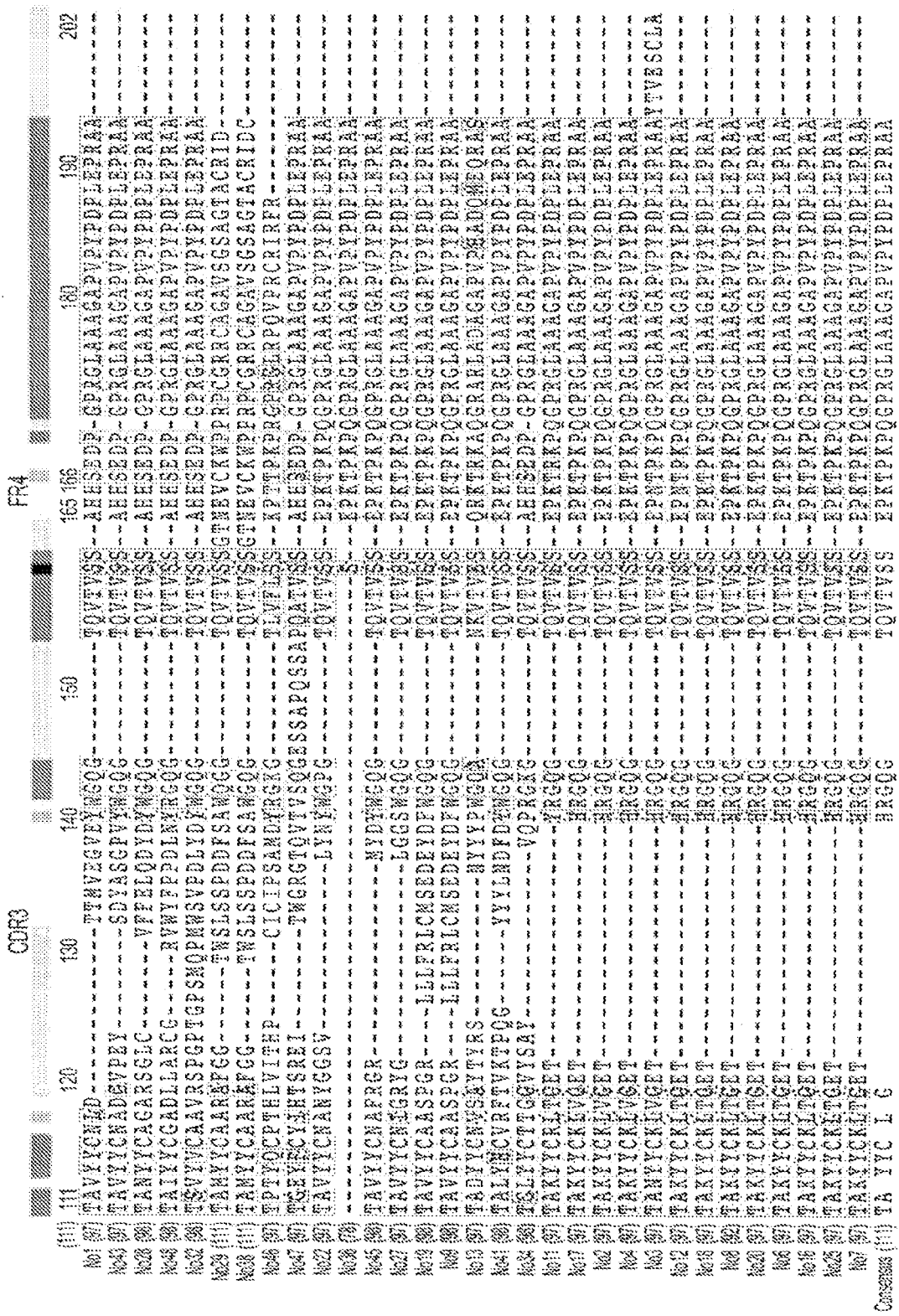
FIG. 2B is a diagram showing the comparison of the coding sequences of the clones.

Example 5. Expression and Purification of rSPA-Nb with Specificity 5.1 Construction of rSPA-Nb Prokaryotic Expression Vector The 31 clones selected by Phage ELISA were sent for sequencing (FIGS. 2A and 2B). No. 6 (Nb6), which had a low affinity value, and 17 (Nb17), which had a high affinity were PCR amplified using clone plasmid carrying BamH I and Xho I restriction sites. After the restriction digest, it was cloned to PET-30a plasmid, and sent for sequencing.

5.2 Expression and Purification of Nanobodies

Figure 3:
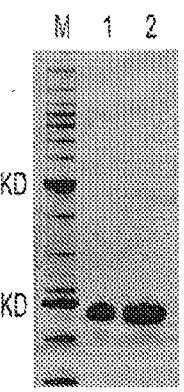
FIG. 3 is a diagram of SDS-PAGE of Nb6 and Nb17: M, Mark; 1, Nb6; 2, Nb17.
Figure 4:
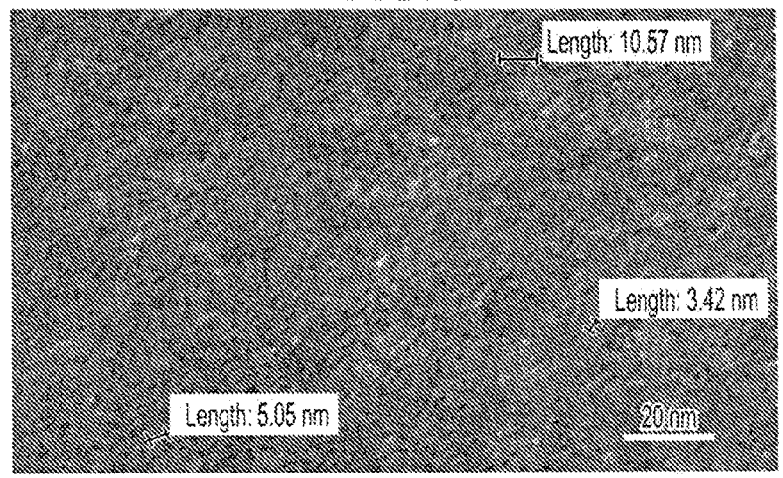
FIG. 4 is a diagram of Electron microscopy image of Nb17.

Recombinant plasmid with correct sequence was transformed into *E. coli* BL21 (DE3), the expression conditions were optimized, and protein expression was induced at 25° C., 0.8 mmol/L IPTG. The expressed product was purified with nickel affinity chromatography and Superdex 75 columns. SDS-PAGE electrophoresis showed that the expressed nanobody had a molecular weight of 17 kDa (FIG. 3). As measured by BCA, the purified proteins had concentration levels of 10 mg/L and 12 mg/L, respectively. Observed under the electron microscope, the size of the antibodies was in the nanometer scale. (FIG. 4).

The 31 clones obtained by the present invention are effective lung-targeting ligands as their nucleotide sequences and amino acid sequences specifically bind to SP-A, which are listed below:
1) Nucleotide sequence listing:

```
NO. 1, Nb1
                                                        (SEQ ID NO 6)
ATGCAGGCCCAGCTGGCCGGTCAGTTGCAGCTCGTGGAGTCCGGGGGAGGCTTGG
TGCAGCCTGGGGGGTCTCTGAAACTCTCCTGTACAGCCTCAGAAACCACGTTCGAG
ATCTATCCCATGGCCTGGTACCGCCAGGCTCCAGGGAAGCAGCGCGAGTTGGTCG
CGGGCATTAATATGATCAGTAGTACAAAGTATATAGACTCTGTGAAGGGCCGATTC
ACCATCTCCAGAGACAACGACAAGAACACGATGTATCTGCAAATGAACAGCCTGA
AACCTGAGGATACGGCCGTCTATTACTGTAATTTAGACACCACAATGGTGGAAGGT
GTCGAGTACTGGGGCCAGGGGACCCAGGTCACCGTCTCCTCCGCGCACCACAGCG
AAGACCCCGGCCCCCGAGGCCTTGCGGCCGCAGGTGCGCCGGTGCCGTATCCGGA
TCCGCTGGAACCGCGTGCCGCATAG

NO. 2, Nb2
                                                        (SEQ ID NO 7)
ATGCAGGCCCAGCTGGCCGTTCAGTTGCAGCTCGTGGAGTCAGGGGGAGGCTTGG
TGCAACCTGGGGGGTCTCTGAGACTCTCCTGTGTAGTCTCTGGAGTCACCATCAGT
AATTATGGTATGAGCTGGGTCCGCCAGGCTCCGGGAAAGGGGCTCGAGTGGATCT
CAACTATTTATAGTAATGGTCACACATACTCTGCGGACTCCGTGAAGGGCCGATTC
ACCATCTCCAGAGACAACGCCAAGAACACGCTGTATCTGCAAATGAACAGCCTGA
AACCTGAGGACACGGCCAAGTATTATTGTAAATTGGTGGGAGAGACCCACCGGGG
CCAGGGGACCCAGGTCACCGTCTCCTCAGAACCCAAGACACCAAAACCACAAGGC
CCCCGAGGCCTTGCGGCCGCAGGTGCGCCGGTGCCGTATCCGGATCCGCTGGAAC
CGCGTGCCGCATAG

NO. 3, Nb3
                                                        (SEQ ID NO 8)
ATGCAGGCCCAGCTGGCCGTTCAGTTGCAGCTCGTGGAGTCAGGGGGAGGCTTGG
TGCAACCTGGGGGGTCTCTGAGACTCTCCTGTGTAGTCTCTGGAGTCACCTTCAAT
AATTATGGTATGAGCTGGGTCCGCCAGGCTCCGGGAAAGGGGCTCGAGTGGATCT
```

-continued
CAAGTATTTATAGTAATGGTCACACATACTCTGCGGACTCCGTGAAGGGCCGATTC
ACCATCTCCAGAGACAACGCCAACAACACCCTGTATCTGCAAATGAACAGCCTGA
AACCTGAGGACACGGCCAACTATTATTGTAAATTGGTGGGAGAGACCCACCGGGG
CCAGGGGACCCAAGTCACCGTCTCCTCAGAACCCAACACACCAAAACCACAAGGC
CCCCGAGGCCTTGCGGCCGCAGGTGCGCCGGTGCCGTATCCGGATCCGCTGGAAC
CGCGTGCCGCATATACTGTTGAAAGTTGTTTAGCATAACCTCATACAGAAAATTCA
TTTACTAG NO. 4, Nb4
(SEQ ID NO 9)

ATGCAGGCCCAGCTGGCCGTTCAGTTGCAGCTCGTGGAGTCAGGGGGAGGCTTGG
TGCAACCTGGGGGGTCTCTGAGACTCTCCTGTGTAGTCTCTGGAGTCACCATCAGT
AATTATGGTATGAGCTGGGTCCGCCAGGCTCCGGGAAGGGGCTCGAGTGGATCT
CAACTATTTATAGTAATGGTCACACATACTCTGCGGACTCCGTGAAGGGCCGATTC
ACCATCTCCAGAGACAACGCCAAGAACACGCTGTATCTGCAAATGAACAGCCTGA
AACCTGAGGACACGGCCAAGTATTATTGTAAATTGGTGGGAGAGACCCACCGGGG
CCAGGGGACCCAGGTCACCGTCTCCTCAGAACCCAAGACACCAAAACCACAAGGC
CCCCGAGGCCTTGCGGCCGCAGGTGCGCCGGTGCCGTATCCGGATCCGCTGGAAC
CGCGTGCCGCATAG

NO. 6, Nb6
(SEQ ID NO 10)

ATGCAGGCCCAGCTGGCCGTTCAGTTGCAGCTCGTGGAGTCGGGAGGGAGGCCTG
GTGCAGCCTGGGGGGTCTCTGAGACTCTCCTGTACAGCCTCCGAGATCACTTTGGA
TTATTATGTCATAGGCTGGTTCCGCCAGGCCCCAGGGAAGGAGCGTGAGCGCCTC
TCATGTATTAGTAACAATGATGATAATGGCCACATTGAGCCTTCCGTCAAGGGCCG
ATTCGCTATTTCCAGAGACAGCGCCAAGAACACGCTGTGTCTGCAAATGAACAGC
CTGAAACCTGAGGACACGGCCGTGTATTACTGTGATTTTTGGCGTGCTATCTATAA
TGGGACCATATCTACTGGGGCCAGGGGAGCCAGGTCACCAGCTCCTCAGCGCACC
ACAGCGAAGACCCCGGCCCCCGAGGCCTTGCGGCCGCAGGTGCGCCGGTGCCGTA
TCCGGATCCGCTGGAACCGCGTGCCGCATAG

NO. 7, Nb7
(SEQ ID NO 11)

ATGTTCTTTCTATGCAGGCCCAGCTGGCCGGTCAGTTGCAGCTCGTGGAGTCTGGG
GGAGGCTTGGTGCAACCTGGGGGGTCTCTGAGACTCTCCTGTGTAGTCTCTGGAGT
CACCATCAGTAATTATGGTATGACCTGGGTCCGCCAGGCTCCGGGAAAGGGGCTC
GAATGGATCTCAACTGTTTATAGTAATGGTCACACATACTATGCGGACTCCGTGAA
GGGCCGATTCACCATCTCCAGAGACAACGCCAAGAACACGCTGTATCTGCAAATG
AACAGCCTGAAACCTGAGGACACGGCCAAGTATTATTGTAAATTGACGGGAGAGA
CCCACCGGGGCCAGGGGACCCAGGTCACCGTCTCCTCAGAACCCAAGACACCAAA
ACCACAAGGCCCCCGAGGCCTTGCGGCCGCAGGTGCGCCGGTGCCGTATCCGGAT
CCGCTGGAACCGCGTGCCGCATAGN0.8,

NO. 8
(SEQ ID NO 12)

ATGCAGGCCAGCTGGCCGGTCAGTTGCAGCTCGTGGAGTCTGGGGGAGGCTTGGT
GCAACCTGGGGGGTCTCTGATGCTCTCCTGTGTAGTCTCTGGAGTCACCATCAGTA
ATTATGGTATGACCTGGGTCCGCCAGGCTCCGGGAAGGGGCTCGAGTGGATCTC
AACTATTTATAGTAATGGTCACACATACTATGCGGACTCCGTGAAGGGCCGATTCA
CCGCCTCCAGAGACAACGCCAAGAACACGCTGTATCTGCAAATGAACAGCCTGAA
ACCTGAGGACACGGCCAAGTATTATTGTAAATTGACGGGAGAGACCCACCGGGGC
CAGGGGACCCAGGTCACCGTCTCCTCAGAACCCAAGACACCAAAACCACAAGGCC
CCCGAGGCCTTGCGGCCGCAGGTGCGCCGGTGCCGTATCCGGATCCGCTGGAACC
GCGTGCCGCATAG

NO. 9, Nb9
(SEQ ID NO 13 )

ATGTCCTTTCATGCAGGCCCAGCTGGCCGGTCAGTTGCAGCTCGTGGAGTCTGGGG
GAGGCTTGGTGCAGCCTGGGGGGTCTCTGAGACTCTCCTGTACAGCCTCTGAATTC
ACTTTGGATTACCATTCCATAGGCTGGTTCCGCCAGGCCCCAGGGAAGGAGCGTG
AGGGGGTCTCATGTATTAGTTATGGTGATGGTACCACATTTTATACAGACTCCGTG
AAGGGCCGATTCACCATCTCCAGAGACAACGCCAAGAACACGGTGACTCTGCAAA
TGAACAGCCTGAAACCTGAGGACACAGCCGTTTATTACTGTGCAGCATCACCCGG
TCGATTACTATTGTTCAGGCTATGTATGTCCGAGGATGAATATGACTTTTGGGGCC
AGGGGACCCAGGTCACCGTCTCCTCAGAACCCAAGACACCAAAACCACAAGGCCC
CCGAGGCCTTGCGGCCGCAGGTGCGCCGGTGCCGTATCCGGATCCGCTGGAACCG
CGTGCCGCATAG

NO. 11, Nb11
(SEQ ID NO 14)

ATGCAGGCCCAGCTGGCCGGTCAGTTGCAGCTCGTGGAGTCCGGGGGAGGCTTGG
TGCAACCTGGGGGGTCTCTGAGACTCTCCTGTGTAGTCTCTGGAGTCACCTTCAAT
AATTATGGTATGACCTGGGTCCGCCAGGCTCCGGGAAGGGGCTCGAGTGGATCT
CAACTATTTATAGTAATGGTCACACATACTATGCGGACTTCGTGAAGGGCCGATTC
ACCATCTCCAGAGACAACGCCAAGAACACGTTGTATCTGCAAATGATCAGCCTGA
AACCTGAGGACACGGCCAAGTATTATTGTAGATTGACGGAGAGACCTACCGGGG
CCAGGGGACCCAGGTCACCGTCTCCTCAGAACCCAAGACACGAAAACCACAAGGC
CCCCGAGGCCTTGCGGCCGCAGGTGCGCCGGTGCCGTATCCGGATCCGCTGGAAC
CGCGTGCCGCATATACTGTTGAAAGTTGTTTAGCAAAACCTCATACAGAAAATTCA
TTTACTAG

-continued

NO. 12, Nb12

(SEQ ID NO 15)

ATGCAGGCCCAGCTGGCCGGTCAGTTGCAGCTCGTGGAGTCTGGGGGAGGCTTGG
TGCAACCTGGGGGGTCTCTGATGCTCTCCTGTGTAGTCTCTGGAGTCACCATCAGT
AATTATGGTATGACCTGGGTCCGCCAGGCTCCGGGAAAGGGGCTCGAGTGGATCT
CAACTATTTATAGTAATGGTCACACATACTATGCGGACTCCGTGAAGGGCCGATTC
ACCGCCTCCAGAGACAACGCCAAGAACACGCTGTATCTGCAAATGAACAGCCTGA
AACCTGAGGACACGGCCAAGTATTATTGTAAATTGACGGGAGAGACCCACCGGGG
CCAGGGGACCCAGGTCACCGTCTCCTCAGAACCCAAGACACCAAAACCACAAGGC
CCCCGAGGCCTTGCGGCCGCAGGTGCGCCGGTGCCGTATCCGGATCCGCTGGAAC
CGCGTGCCGCATAG

NO. 13, Nb13

(SEQ ID NO 16)

ATGCAGGCCCAGCTGGCCGTTCAGTTGCAGCTCGTGGAGTCTGGGGGAGGCTTGG
TGCAACCTGGGGGGTCTCTGAGACTCTCCTGTGCAGCCTCTGGAATCATCTTGAAT
TTCTATGGGATGGGCTGGGACCGCCAGACTCCAGGCCAGGGGCTCGAGGGGGTCT
CATATGTTAATAATAATGGTATGACAAACTATGCAGACTCCGTGAAGGGCCGATT
CACCATCTCCAGAGACAACGCCAAGAACACAATGTATCTGCAAATGAACAGCCTG
AAACCTGAGGACACGGCCGACTATTACTGTAATGTGAGTGCATACACCTATAGGA
GTAATTACTACTACCCCTGGGGCCAGGCAAACCACGTCACAGTCTCATCACAACG
CAAGACACGAAAAGCACAAGGACGCGCACGCCTTGCGGACGCAGGTGCGCCGGT
GCCGCATGCCGATCAGATGGAACAACGTGCCTCATAAACTGTTGAAAGTTGTTTAT
CAAATCCTCATATATAAAATTAATATACAAATTTCTATAAATACGATAAATCTTAA
GATCGTTAG

NO. 16, Nb16

(SEQ ID NO 17)

ATGCAGGCCCAGCTGGCCGGTCAGTTGCAGCTCGTGGAGTCTGGGGGAGGCTTGG
TGCAACCTGGGGGGTCTCTGAGACTCTCCTGTGTAGTCTCTGGAGTCACCATCAGT
AATTATGGTATGACCTGGGTCCGCCAGGCTCCGGGAAAGGGGCTCGAATGGATCT
CAACTGTTTATAGTAATGGTCACACATACTATGCGGACTCCGTGAAGGGCCGATTC
ACCATCTCCAGAGACAACGCCAAGAACACGCTGTATCTGCAAATGAACAGCCTGA
AACCTGAGGACACGGCCAAGTATTATTGTAAATTGACGGGAGAGACCCACCGGGG
CCAGGGGACCCAGGTCACCGTCTCCTCAGAACCCAAGACACCAAAACCACAAGGC
CCCCGAGGCCTTGCGGCCGCAGGTGCGCCGGTGCCGTATCCGGATCCGCTGGAAC
CGCGTGCCGCATAG

NO. 17, Nb17

(SEQ ID NO 18)

ATGCAGGCCCAGCTGGCCGTTCAGTTGCAGCTCGTGGAGTCAGGGGGAGGCTTGG
TGCAACCTGGGGGGTCTCTGAGACTCTCCTGTGTAGTCTCTGGAGTCACCATCAGT
AATTATGGTATGAGCTGGGTCCGCCAGGCTCCGGGAAAGGGGCTCGAGTGGATCT
CAACTATTTATAGTAATGGTCACACATACTCTGCGGACTCCGTGAAGGGCCGATTC
ACCATCTCCAGAGACAACGCCAAGAACACGCTGTATCTGCAAATGAACAGCCTGA
AACCTGAGGACACGGCCAAGTATTATTGTAAATTGGTGGGAGAGACCCACCGGGG
CCAGGGGACCCAGGTCACCGTCTCCTCAGAACCCAAGACACCAAAACCACAAGGC
CCCCGAGGCCTTGCGGCCGCAGGTGCGCCGGTGCCGTATCCGGATCCGCTGGAAC
CGCGTGCCGCATAG

NO. 18, Nb18

(SEQ ID NO 19)

ATGCAGGCCCAGCTGGCCGGTCAGTTGCAGCTCGTGGAGTCTGGGGGAGGCTTGG
TGCAACCTGGGGGGTCTCTGATGCTCTCCTGTGTAGTCTCTGGAGTCACCATCAGT
AATTATGGTATGACCTGGGTCCGCCAGGCTCCGGGAAAGGGGCTCGAGTGGATCT
CAACTATTTATAGTAATGGTCACACATACTATGCGGACTCCGTGAAGGGCCGATTC
ACCGCCTCCAGAGACAACGCCAAGAACACGCTGTATCTGCAAATGAACAGCCTGA
AACCTGAGGACACGGCCAAGTATTATTGTAAATTGACGGGAGAGACCCACCGGGG
CCAGGGGACCCAGGTCACCGTCTCCTCAGAACCCAAGACACCAAAACCACAAGGC
CCCCGAGGCCTTGCGGCCGCAGGTGCGCCGGTGCCGTATCCGGATCCGCTGGAAC
CGCGTGCCGCATAG

NO. 19, Nb19

(SEQ ID NO 20)

ATGTATTAGTTATGGTGATGGTACCACATTTTATACAGACTCCGTGAAGGGCCGAT
TCACCATCTCCAGAGACAACGCCAAGAACACGGTGACTCTGCAAATGAACAGCCT
GAAACCTGAGGACACAGCCGTTTATTACTGTGCAGCATCACCCGGTCGATTACTAT
TGTTCAGGCTATGTATGTCCGAGGATGAATATGACTTTTGGGCCCAGGGGACCCA
GGTCACCGTCTCCTCAGAACCCAAGACACCAAAACCACAAGGCCCCCGAGGCCTT
GCGGCCGCAGGTGCGCCGGTGCCGTATCCGGATCCGCTGGAACCGCGTGCCGCAT
AG

NO. 20, Nb20

(SEQ ID NO 21)

ATGCAGGCCCAGCTGGCCGTTCAGTTGCAGCTCGTGGAGTCGGGGGGAGGCTTGG
TGCAACCTGGGGGGTCTCTGATGCTCTCCTGTGTAGTCTCTGGAGTCACCATCAGT
AATTATGGTATGACCTGGGTCCGCCAGGCTCCGGGAAAGGGGCTCGAGTGGATCT
CAACTATTTATAGTAATGGTCACACATACTATGCGGACTCCGTGAAGGGCCGATTC
ACCGCCTCCAGAGACAACGCCAAGAACACGCTGTATCTGCAAATGAACAGCCTGA
AACCTGAGGACACGGCCAAGTATTATTGTAAATTGACGGGAGAGACCCACCGGGG
CCAGGGGACCCAGGTCACCGTCTCCTCAGAACCCAAGACACCAAAACCACAAGGC

-continued

CCCCGAGGCCTTGCGGCCGCAGGTGCGCCGGTGCCGTATCCGGATCCGCTGGAAC
CGCGTGCCGCATAG

NO. 22, Nb22 (SEQ ID NO 22)

ATGCAGGCCCAGCTGGCCGGTCAGTTGCAGCTCGTGGAGTCTGGGGGAGGCTTGG
TGCAGCCTGGGGGGTCTCTGAGACTCTCCTGTGCAGCCTCCGGAAGAGCCTTCAGT
GTGTATGCCGTGGGCTGGTATCGCCAGCCTCCAGGGAAGCAGCGCGAGCTGGTCG
CGAGTATCACTGATGGTGGAAGCACAAACTATGCAGACTCGGTGAAGGGCCGATT
CACCGTCTCCAGAGACAACGCCAGAAATACGGCGTACCTGGATATGAACAGCCTG
AAAGTTGAGGACACGGCCGTCTATTACTGTAATGCAAATTATGGGGGTAGTGTCC
TATACAACTACTGGGGCCCGGGAACCCAAGTCACCGTCTCCACAGAACCCAAGAC
ACCAAAACCACAAGGCCCCCGAGGCCTTGCGGCCGCAGGTGCGCCGGTGCCGTAT
CCGGATCCGCTGGAACCGCGTGCCGCATAG

NO. 25, Nb25 (SEQ ID NO 23)

ATGCAGGCCCAGCTGGCCGGTCAGTTGCAGCTCGTGGAGTCTGGGGGAGGCTTGG
TGCAACCTGGGGGGTCTCTGAGACTCTCCTGTGTAGTCTCTGGAGTCACCATCAGT
AATTTATGGTATGACCTGGGTCCGCCAGGCTCCGGGAAGGGGCTCGAATGGATCT
CAACTGTTTATAGTAATGGTCACACATACTATGCGGACTCCGTGAAGGGCCGATTC
ACCATCTCCAGAGACAACGCCAAGAACACGCTGTATCTGCAAATGAACAGCCTGA
AACCTGAGGACACGGCCAAGTATTATTGTAAATTGACGGGAGAGACCCACCGGGG
CCAGGGGACCCAGGTCACCGTCTCCTCAGAACCCAAGACACCAAAACCACAAGGC
CCCCGAGGCCTTGCGGCCGCAGGTGCGCCGGTGCCGTATCCGGATCCGCTGGAAC
CGCGTGCCGCATAG

NO. 27, Nb27 (SEQ ID NO 24)

ATGCAGGCCCAGCTGGCCGTTCAGTTGCAGCTCGTGGAGTCAGGGGGAGGCTTGG
TGCAGCCTGGGGGGTCTCTGAGACTCTCCTGTGAAGTCTCTGGAAGCAGAGGCAG
TATCTATTTCTCGGGCTGGTACCGCCAGGCTCCAGGGAAGCAGCGCGAGTTGGTC
GCAAGTATTACTAGTGGTGGTACTACAAATTATGCAGACTCCGTGAAGGGCCGAT
TCACCATCTCCAGAGACAACGCCAAGAACACGGTGTATCTGCAAATGAACAGCCT
GAAACCTGAGGACACGGCCGTCTATTACTGTAATATAGGTCGATACGGATTGGGC
GGGTCCTGGGGTCAGGGGACCCAGGTCACCGTCTCCTCAGAACCCAAGACACCAA
AACCACAAGGCCCCCGAGGCCTTGCGGCCGCAGGTGCGCCGGTGCCGTATCCGGA
TCCGCTGGAACCGCGTGCCGCATAG

NO. 28, Nb28 (SEQ ID NO 25)

ATGCAGGCCCAGCTGGCCGGTCAGTTGCAGCTCGTGGAGTCCGGTGGAGGCTTGG
TGCAGCCTGGGGGGTCTCTGAGACTCTCCTGTGAAGCCTCTGGCTTCACTTTCGAC
GATTATGCCATAGGCTGGTTCCGCCAGGCCCCAGGGAAGGAGCGTGAGGAGGTCT
CATGTATTAGTCATAATGGAGGTACCACAAACTATGCAGACTCCGTGAAGGGCCG
ATTCTCCATCTCCAGAGACAACGCCAAGAACACGGTGTATCTGCAAATGAACGGC
CTGAAACCTGAGGACACAGCCAACTATTACTGTGCAGGCGCGCGTTCCGGACTAT
GTGTGTTTTTTGAGTTGCAAGATTATGACTACTGGGGCCAGGGGACCCAGGTCACC
GTCTCCTCAGCGCACCACAGCGAAGACCCCGGCCCCCGAGGCCTTGCGGCCGCAG
GTGCGCCGGTGCCGTATCCGGATCCGCTGGAACCGCGTGCCGCATAG

NO. 29, Nb29 (SEQ ID NO 26)

ATGCAGGCCCAGCCGGCCGTCCTGGCTGCTCTTCTACAAGGTGTCCAGGCTCAGGT
GAAGCTGGTGGAGTCTGGGGGAGGCTCGGTGCAGGCTGGAGGGTCTCTGAGACTC
TCCTGTACAGCCTCTGGATCAGACTACAGATGGATGTACATCGCCCGGTTTCGCCA
ATGTCCAGGGAAGGAGCGCGAGGGGGTCGCAGCAATTTATACTGATGATACTGAT
GATAGTAGTCCGATCTATGCCACCTCCGCCAAGGGCCGATTCACCATCTCCCAAGA
CAAGGACAAGAACGCGGTATATCTGCAAATGAACAGCCCGAAACCTGAGGACAC
TGCCATGTACTACTGTGCGGCAAGAGCGTTCGGTGGTACCTGGAGCTTGAGCTCCC
CGGACGACTTTAGTGCCTGGGGCCAGGGGACCCAGGTCACCGTCTCCTCAGGAAC
GAATGAAGTATGCAAGTGGCCCCCGAGGCCTTGCGGCCGCAGGTGCGCCGGTGCC
GTATCCGGATCCGCTGGAACCGCGTGCCGCATAG

NO. 32, Nb32 (SEQ ID NO 27)

ATGCAGGCCCAGCTGGCCGGTCAGTTGCAGCTCGTGGAGTCTGGGGGAGGCTTGG
TGCAGCCTGGGGGGTCTCTGAGACTCTCCTGTACAGCCTCTAAATTCCATTTGGAT
TCTTATGCCGTAGCCTGGTTCGCCAGACCCCAGGGAAGGAGCGTGAGGCGGTCT
CATTTATAAATACTAGTGATGATGTCACATACTTTGCTGACTCCGTAAAGGGCCGA
TTCACCATCTCCAGAGACAACTCCAAGAACACGGTATATCTGCAAATGAACGTCC
TGAAACCAGAAGACACTTCCGTTTATGTGTGTGCAGCGGTAAGAAGTCCCGGCCC
TACCGGCCCAGTATGCAGCCTATGTGGTCGGTGCCTGACCTGTATGACTACTGGG
GCCAGGGGACCCAGGTCACCGTCTCCTCAGCGCACCACAGCGAAGACCCCGGCCC
CCGAGGCCTTGCGGCCGCAGGTGCGCCGGTGCCGTATCCGGATCCGCTGGAACCG
CGTGCCGCATAG

NO. 34, Nb34 (SEQ ID NO 28)

ATGCAGGCCCAGCTGGCCGTTCAGTTGCAGCTCGTGGAGTCCGGTGGAGGCACGG
TGCAGCCTGGGGGGTCTCTGAACCTCTCCTGTGTAACTTCTGGATTCACCTTCAGT

-continued

AGGCATGATATGAGTTGGGTCCGCCAGGCTCCAGGGAAGGGGCCCGAGTGGATCT
CAGGTATTGGTACTAGTGGTACAAGCGGACGTTATGCGAGCTCCGTGAAGGGCCG
ATTCACCATCTCCAGAGACAACGCCAAGGATACGCTGTATCTCCAAATGGATAGC
CTGAAACCTGAAGCACGGGCCTATATTACTGCACGACCGGCGGCGTTTATAGCG
CCTATGTACAACCCGGGGCAAGGGGACGCAGGTCACCGTCTCCTCGGCGCACCA
CAGCGAAGACCCCGGCCCCCGAGGCCTTGCGGCCGCAGGTGCGCCGGTGCCGTAT
CCGGATCCGCTGGAACCGCGTGCCGCATAG

NO. 36, Nb36
(SEQ ID NO 29)
ATGCAGGCCCAGCTGGCCGTTCAGTTGCAGCTCGTGGAGTCGGGTGGAGGCTTGG
TGCAGCCTGGGGGGTCTCTGAGACTCTCCTGTGCAGCCTCCGGAAGAGCCTTCAGT
GTGTATGCCGTGGGCTGGTACCGCCAGATTCCAGGGAATCAGCGCGAAATGGTCG
CAGCTATTAGTAGCGGTGGTAACACAAAATACTCGGACTCCGTGAAGGGCCGCTT
CACCGTCTCCTCAGAACCCAAGACACCAAAACCACAAGGCCCCCGAGGCCTTGCG
GCCGCAGGTGCGCCGGTGCCGTATCCGGATCCGCTGGAACCGCGTGCCGCATAG

NO. 38, Nb38
(SEQ ID NO 30)
ATGCAGGCCCAGCCGGCCGTCCTGGCTGCTCTTCTACAAGGTGTCCAGGCTCAGGT
GAAGCTGGTGGAGTCTGGGGGAGGCTCGGTGCAGGCTGGAGGGTCTCTGAGACTC
TCCTGTACAGCCTCTGGATCAGACTACAGATGGATGTACATCCGGTTTCGCCA
ATGTCCAGGGAAGGAGCGCGAGGGGGTCGCAGCAATTTATACTGATGATACTGAT
GATAGTAGTCCGATCTATGCCACCTCCGCCAAGGGCCGATTCACCATCTCCAAGA
CAAGGACAAGAACGCGGTATATCTGCAAATGAACAGCCCGAAACCTGAGGACAC
TGCCATGTACTACTGTGCGGCAAGAGCGTTCGGTGGTACCGGAGCTTGAGCTCCC
CGGACGACTTTAGTGCCTGGGGCCAGGGGACCCAGGTCACCGTCTCCTCAGGAAC
GAATGAAGTATGCAAGTGGCCCCCGAGGCCTTGCGGCCGCAGGTGCGCCGGTGCC
GTATCCGGATCCGCTGGAACCGCGTGCCGCATAG

NO. 41, Nb41
(SEQ ID NO 31)
ATGCAGGCCCAGCTGGCCGGTCAGTTGCAGCTCGTGGAGTCGGGTGGAGGCATGG
TGCAGCCTGGGGGGTCTCTGAGACTTCTCCTGTGCAGCCTCTGGATTCATTTTCAGT
CGCTATGACATGGGTTGGGTCCGCCAAACTCCAGGGAAGGGGCGCGAGTGGGTCT
CAGGTATTAATTCTGGTGGTGGGCGTACATACTATGCGGACTCCGTGAAGGGCCG
ATTCACCATCTCCAGAGACGACGATAAGGCTACGTTGTATTTGTCAATGGACGGCC
TGAAACCTGAGGACACGGCCCTGTACCATTGTGTGAGATTCACCGTGAAAACGCC
GCAAGGTTACTACTACCTGAACGATTTCGACTACTGGGGCCAGGGGACCCAGGTC
ACCGTCTCCTCCGAACCCAAGACACCAAAACCACAAGGCCCCCGAGGCCTTGCGG
CCGCAGGTGCGCCGGTGCCGTATCCGGATCCGCTGGAACCGCGTGCCGCATA

NO. 43, Nb43
(SEQ ID NO 32)
ATGCAGGCCCAGCTGGCCGGTCAGTTGCAGCTCGTGGAGTCTGGGGGAGGCTTGG
TGCAGATTGGGGGGTCTCTGAGACTCTCCTGTGCAGCCTCTGGAAGCGACTTCAGT
ATCTATCACATGGGCTGGTACCGCCAGGCTCCAGGGAAGCAGCGCGAGTTGGTCG
CAGCTATTACTAGTGGTGGTAGCACAAACTATGCAGACTCCGTGAAGGGCCGATT
CACCATCTCCAGTGACAACGCCAAGAACACGGTGTATCTGCAAATGAACAGCCTG
AAACCTGAGGACACGGCCGTCTATTATTGTAATGCAGATGGGGTCCCCGAGTATA
GCGACTATGCCTCCGGCCCGGTGTACTGGGGCCAGGGGACCCAGGTCACCGTCTC
CTCAGCGCACCACAGCGAAGACCCCGGCCCCCGAGGCCTTGCGGCCGCAGGTGCG
CCGGTGCCGTATCCGGATCCGCTGGAACCGCGTGCCGCATAG

NO. 45, Nb45
(SEQ ID NO 33)
ATGCAGGCCCAGCTGGCCGTTCAGTTGCAGCTCGTGGAGTCGGGTGGAGGCTTGG
TGCAGGCTGGGGGGTCTCTGAGACTGTCCTGTGTGGCCTCTGGAAGTATGTTCAAT
TTCTATGGCATGGCCTGGTACCGGCAGGCTCCAGGGAAGCAGCGCGAGTTGGTCG
CATCAATTGATAGTGAGGGTAGAACGACAAACTATCCAGACTCCCTGAAGGGCCG
ATTCACCATCTCCAGGGACGACGCCAAGAGCACGGCGTATCTGCAAATGAACAAC
CTGATTCCTGACGCACACGGCCGTCTATTACTGTAATGCCTTCCGAGGGAGGATGTA
TGACTACTGGGGCCAGGGGACCCAGGTCACCGTCTCCTCAGAACCCAAGACACCA
AAACCACAAGGCCCCCGAGGCCTTGCGGCCGCAGGTGCGCCGGTGCCGTATCCGG
ATCCGCTGGAACCGCGTGCCGCATAG

NO. 46, Nb46
(SEQ ID NO 34)
ATGCAGGCCCAGCTGGCCGGTCAGTTGCAGCTCGTGGAGTCTGGTGGAAGGTTGG
TTGCACCCGGGAGGTCTTTGAAACTCTCCCGGACCTTCTCTGGTCTCTATTTGCATT
CAAGTGCCTTTGGCTGGTTTCCCCACGTTCCAGGGAAGCGCGTGAAGGGGTTGCC
TTCCTTTGTAATTCCGGTTCTGACCCAATATATTTACACCCCGAGAAGGGCATTTTC
ACTCTCTCCAGACACTGTGTCAAATGAACGGTTTCTCCGTTTGAGGACAACGATAC
TGTAGAACACACCCCTACTTATCAGTGCCCAACACATCTAG

NO. 47, Nb47
(SEQ ID NO 35)
ATGCAGGCCCAGCTGGCCGGTCAGTTGCAGCTCGTGGAGTCGGGTGGAGGCAGGG
TGCAGGCTGGGGGGTCTCTGACACTCTCCTGTGCAGCCTCTGGAGACATCTTCACT
CTCGCTTCCATGGGATGGTATCGTGAAGATCTACACAAAAAGCGCGAGTTGGTGG
CCCAACTGATGAGTGATGGTACCGCGAATTATGGAGATTCCGTGAAGGGCCGAGT

-continued

```
CACCATCTCCAGAGACGACGTCGATACCACAGTGCATCTGCGAATGAATACCCTG
CAACCGTCCGACACGGGAGAATATTTTTGTTATATCCATACTTCCCGCGAAATTAC
CTGGGGCCGGGGGACCCAGGTCACCGTCTCCCAGGGAGAGTCCTCGGCGCCTCAG
TCCTCGGCGCCTCAGGCCACCGTCTCCTCGGCGCACCACAGCGAAGACCCCGGCC
CCCGAGGCCTTGCGGCCGCAGGTGCGCCGGTGCCGTATCCGGATCCGCTGGAACC
GCGTGCCGCATAG
```

NO. 48, Nb48

(SEQ ID NO 36)

```
ATGCAGGCCCAGCTGGCCGGTCAGTTGCAGCTCGTGGAGTCTGGGGGAGGCCTGG
TCGAAGTTGGGGAGTCTCTGAGACTCTCCTGTGTAGCACTCGGATTCACTTTGGAC
GGGTATGCCATTGGCTGGTTCCGCCAGGCCCCGGGGAAGGAGCGTGAGAAAATCT
CATGCATTAGTAGTACTGGCGATAGTACAAATTATGATGACTCCGTGAAGGGCCG
ATTCACCATCTCCAGAGACACTGCCAAGAGCACGGTGTTTCTGCAAATGAACAAC
CTGATACCTGAGGACACAGCCATTTATTACTGTGGCGCAGACCTCTTGGCGCGGTG
TGGTCGTGTTTGGTACTTCCCGCCCGACCTTAATTACCGGGGCCAGGGGACCCAGG
TCACCGTTTCTTCAGCGCACCACAGCGAAGACCCCGGCCCCCGAGGCCTTGCGGC
CGCAGGTGCGCCGGTGCCGTATCCGGATCCGCTGGAACCGCGTGCCGCATAG
```

2) Amino acid sequence listing:

(1) (SEQ ID NO 37) Nb1
```
  1  MQAQLAGQLQ LVESGGGLVQ PGGSLKLSCT ASETTFEIYP MAWYRQAPGK QRELVAGINM
 61  ISSTKYIDSV KGRFTISRDN DKNTMYLQMN SLKPEDTAVY YCNLDTTMVE GVEYWGQGTQ
121  VTVSSAHHSE DPGPRGLAAA GAPVPYPDPL EPRAA
```

(2) (SEQ ID NO 38) Nb2
```
  1  MQAQLAVQLQ LVESGGGLVQ PGGSLRLSCV VSGVTISNYG MSWVRQAPGK GLEWISTIYS
 61  NGHTYSADSV KGRFTISRDN AKNTLYLQMN SLKPEDTAKY YCKLVGETHR GQGTQVTVSS
121  EPKTPKPQGP RGLAAAGAPV PYPDPLEPRA A
```

(3) (SEQ ID NO 39) Nb3
```
  1  MQAQLAVQLQ LVESGGGLVQ PGGSLRLSCV VSGVTFNNYG MSWVRQAPGK GLEWISSIYS
 61  NGHTYSADSV KGRFTISRDN ANNTLYLQMN SLKPEDTANY YCKLVGETHR GQGTQVTVSS
121  EPNTPKPQGP RGLAAAGAPV PYPDPLEPRA AYTVESCLA
```

(4) (SEQ ID NO 40) Nb4
```
  1  MQAQLAVQLQ LVESGGGLVQ PGGSLRLSCV VSGVTISNYG MSWVRQAPGK GLEWISTIYS
 61  NGHTYSADSV KGRFTISRDN AKNTLYLQMN SLKPEDTAKY YCKLVGETHR GQGTQVTVSS
121  EPKTPKPQGP RGLAAAGAPV PYPDPLEPRA A
```

(6) (SEQ ID NO 41) Nb6
```
  1  LQAQLAGQLQ LVESGGGLVQ PGGSLRLSCV VSGVTISNYG MTWVRQAPGK GLEWISTVYS
 61  NGHTYYADSV KGRFTISRDN AKNTLYLQMN SLKPEDTAKY YCKLTGETHR GQGTQVTVSS
121  EPKTPKPQGP RGLAAAGAPV PYPDPLEPRA A
```

(7) (SEQ ID NO 42) Nb7
```
  1  MQAQLAGQLQ LVESGGGLVQ PGGSLRLSCV VSGVTISNYG MTWVRQAPGK GLEWISTVYS
 61  NGHTYYADSV KGRFTISRDN AKNTLYLQMN SLKPEDTAKY YCKLTGETHR GQGTQVTVSS
121  EPKTPKPQGP RGLAAAGAPV PYPDPLEPRA A
```

(8) (SEQ ID NO 43) Nb8
```
  1  AGQLQLVESG GGLVQPGGSL MLSCVVSGVT ISNYGMTWVR QAPGKGLEWI STIYSNGHTY
 61  YADSVKGRFT ASRDNAKNTL YLQMNSLKPE DTAKYYCKLT GETHRGQGTQ VTVSSEPKTP
121  KPQGPRGLAA AGAPVPYPDP LEPRAA
```

(9) (SEQ ID NO 44) Nb9
```
  1  MQAQLAGQLQ LVESGGGLVQ PGGSLRLSCT ASEFTLDYHS IGWFRQAPGK EREGVSCISY
 61  GDGTTFYTDS VKGRFTISRD NAKNTVTLQM NSLKPEDTAV YYCAASPGRL LLFRLCMSED
121  EYDFWGQGTQ VTVSSEPKTP KPQGPRGLAA AGAPVPYPDP LEPRAA
```

(11) (SEQ ID NO 45) Nb 11
```
  1  MQAQLAGQLQ LVESGGGLVQ PGGSLRLSCV VSGVTFNNYG MTWVRQAPGK GLEWISTIYS
 61  NGHTYYADFV KGRFTISRDN AKNTLYLQMI SLKPEDTAKY YCRLTGETYR GQGTQVTVSS
121  EPKTRKPQGP RGLAAAGAPV PYPDPLEPRA A
```

(12) (SEQ ID NO 46) Nb12
```
  1  MQAQLAGQLQ LVESGGGLVQ PGGSLMLSCV VSGVTISNYG MTWVRQAPGK GLEWISTIYS
 61  NGHTYYADSV KGRFTASRDN AKNTLYLQMN SLKPEDTAKY YCKLTGETHR GQGTQVTVSS
121  EPKTPKPQGP RGLAAAGAPV PYPDPLEPRA A
```

(13) (SEQ ID NO 47) Nb13
```
  1  MQAQLAVQLQ LVESGGGLVQ PGGSLRLSCA ASGIILNFYG MGWDRQTPGQ GLEGVSYVNN
 61  NGMTNYADSV KGRFTISRDN AKNTMYLQMN SLKPEDTADY YCNVSAYTYR SNYYYPWGQA
121  NHVTVSSQRK TRKAQGRARL ADAGAPVPHA DQMEQRAS
```

(16) (SEQ ID NO 48) Nb161
```
  1  MQAQLAGQLQ LVESGGGLVQ PGGSLRLSCV VSGVTISNYG MTWVRQAPGK GLEWISTVYS
 61  NGHTYYADSV KGRFTISRDN AKNTLYLQMN SLKPEDTAKY YCKLTGETHR GQGTQVTVSS
121  EPKTPKPQGP RGLAAAGAPV PYPDPLEPRA A
```

(17) (SEQ ID NO 49) Nb17
  1   MQAQLAVQLQ LVESGGGLVQ PGGSLRLSCV VSGVTISNYG MSWVRQAPGK GLEWISTIYS
 61   NGHTYSADSV KGRFTISRDN AKNTLYLQMN SLKPEDTAKY YCKLVGETHR GQGTQVTVSS
121   EPKTPKPQGP RGLAAAGAPV PYPDPLEPRA A

(18) (SEQ ID NO 50) Nb18
  1   MQAQLAGQLQ LVESGGGLVQ PGGSLMLSCV VSGVTISNYG MTWVRQAPGK GLEWISTIYS
 61   NGHTYYADSV KGRFTASRDN AKNTLYLQMN SLKPEDTAKY YCKLTGETHR GQGTQVTVSS
121   EPKTPKPQGP RGLAAAGAPV PYPDPLEPRA A

(19) (SEQ ID NO 51) Nb19
  1   MQAQLAGQLQ LVESGGGLVQ PGGSLRLSCT ASEFTLDYHS IGWFRQAPGK EREGVSCISY
 61   GDGTTFYTDS VKGRFTISRD NAKNTVTLQM NSLKPEDTAV YYCAASPGRL LLFRLCMSED
121   EYDFWGQGTQ VTVSSEPKTP KPQGPRGLAA AGAPVPYPDP LEPRAA

(20) (SEQ ID NO 52) Nb20
  1   MQAQLAVQLQ LVESGGGLVQ PGGSLMLSCV VSGVTISNYG MTWVRQAPGK GLEWISTIYS
 61   NGHTYYADSV KGRFTASRDN AKNTLYLQMN SLKPEDTAKY YCKLTGETHR GQGTQVTVSS
121   EPKTPKPQGP RGLAAAGAPV PYPDPLEPRA A

(22) (SEQ ID NO 53) Nb22
  1   MQAQLAGQLQ LVESGGGLVQ PGGSLRLSCA ASGRAFSVYA VGWYRQPPGK QRELVASITD
 61   GGSTNYADSV KGRFTVSRDN ARNTAYLDMN SLKVEDTAVY YCNANYGGSV LYNYWGPGTQ
121   VTVSTEPKTP KPQGPRGLAA AGAPVPYPDP LEPRAA

(25) (SEQ ID NO 54) Nb25
  1   MQAQLAGQLQ LVESGGGLVQ PGGSLRLSCV VSGVTISNYG MTWVRQAPGK GLEWISTVYS
 61   NGHTYYADSV KGRFTISRDN AKNTLYLQMN SLKPEDTAKY YCKLTGETHR GQGTQVTVSS
121   EPKTPKPQGP RGLAAAGAPV PYPDPLEPRA A

(27)  SEQ ID NO 55) Nb27
  1   MQAQLAVQLQ LVESGGGLVQ PGGSLRLSCE VSGSRGSIYF SGWYRQAPGK QRELVASITS
 61   GGTTNYADSV KGRFTISRDN AKNTVYLQMN SLKPEDTAVY YCNIGRYGLG GSWGQGTQVT
121   VSSEPKTPKP QGPRGLAAAG APVPYPDPLE PRAA

(28) (SEQ ID NO 56) Nb28
  1   MQAQLAGQLQ LVESGGGLVQ PGGSLRLSCE ASGFTFDDYA IGWFRQAPGK EREEVSCISH
 61   NGGTTNYADS VKGRFSISRD NAKNTVYLQM NGLKPEDTAN YYCAGARSGL CVFFELQDYD
121   YWGQGTQVTV SSAHHSEDPG PRGLAAAGAP VPYPDPLEPR AA

(29) (SEQ ID NO 57) Nb29
  1   MQAQPAVLAA LLQGVQAQVK LVESGGGSVQ AGGSLRLSCT ASGSDYRWMY IARFRQCPGK
 61   EREGVAAIYT DDTDDSSPIY ATSAKGRFTI SQDKDKNAVY LQMNSPKPED TAMYYCAARA
121   FGGTWSLSSP DDFSAWGQGT QVTVSSGTNE VCKWPPRPCG RRCAGAVSGS AGTACRID

(32) (SEQ ID NO 58) Nb32
  1   MQAQLAGQLQ LVESGGGLVQ PGGSLRLSCT ASKFHLDSYA VAWFRQTPGK EREAVSFINT
 61   SDDVTYFADS VKGRFTISRD NSKNTVYLQM NVLKPEDTSV YVCAAVRSPG PTGPSMQPMW
121   SVPDLYDYWG QGTQVTVSSA HHSEDPGPRG LAAAGAPVPY PDPLEPRAA

(34) (SEQ ID NO 59) Nb34
  1   MQAQLAVQLQ LVESGGGTVQ PGGSLNLSCV TSGFTFSRHD MSWVRQAPGK GPEWISGIGT
 61   SGTSGRYASS VKGRFTISRD NAKDTLYLQM DSLKPEDTGL YYCTTGGVYS AYVQPRGKGT
121   QVTVSSAHHS EDPGPRGLAA AGAPVPYPDP LEPRAA

(36) (SEQ ID NO 60) Nb36
  1   MQAQLAVQLQ LVESGGGLVQ PGGSLRLSCA ASGRAFSVYA VGWYRQIPGN QREMVAAISS
 61   GGNTKYSDSV KGRFTVSSEP KTPKPQGPRG LAAAGAPVPY PDPLEPRAA

(38) (SEQ ID NO 61) Nb38
  1   MQAQPAVLAA LLQGVQAQVK LVESGGGSVQ AGGSLRLSCT ASGSDYRWMY IARFRQCPGK
 61   EREGVAAIYT DDTDDSSPIY ATSAKGRFTI SQDKDKNAVY LQMNSPKPED TAMYYCAARA
121   FGGTWSLSSP DDFSAWGQGT QVTVSSGTNE VCKWPPRPCG RRCAGAVSGS AGTACRIDC

(41) (SEQ ID NO 62) Nb41
  1   MQAQLAGQLQ LVESGGGMVQ PGGSLRLSCA ASGFIFSRYD MGWVRQTPGK GREWVSGINS
 61   GGGRTYYADS VKGRFTISRD DDKATLYLSM DGLKPEDTAL YHCVRFTVKT PQGYYYLNDF
121   DYWGQGTQVT VSSEPKTPKP QGPRGLAAAG APVPYPDPLE PRAA

(43) (SEQ ID NO 63) Nb43
  1   MQAQLAGQLQ LVESGGGLVQ IGGSLRLSCA ASGSDFSIYH MGWYRQAPGK QRELVAAITS
 61   GGSTNYADSV KGRFTISSDN AKNTVYLQMN SLKPEDTAVY YCNADGVPEY SDYASGPVYW
121   GQGTQVTVSS AHHSEDPGPR GLAAAGAPVP YPDPLEPRAA

(45) (SEQ ID NO 64) Nb45
  1   MQAQLAVQLQ LVESGGGLVQ AGGSLRLSCV ASGSMFNFYG MAWYRQAPGK QRELVASIDS
 61   EGRTTNYPDS LKGRFTISRD DAKSTAYLQM NNLIPDDTAV YYCNAFRGRM YDWGQGTQV
121   TVSSEPKTPK PQGPRGLAAA GAPVPYPDPL EPRAA

-continued

(46) (SEQ ID NO 65) Nb46
  1  MQAQLAGQLQ LVESGGRLVA PGRSLKLSRT FSGLYLHSSA FGWFPHVPRE AREGVAFLCN
 61  SGSDPIYLHP EKGIFTLSRH CVKTVSPFED NDTVEHTPTY QCPTHLVITH PCICIPSAMD
121  YRGKGTLVPL SSKPTTPKPR APKALRPQVP RCRIRFR

(47) (SEQ ID NO 66) Nb47
  1  MQAQLAGQLQ LVESGGGRVQ AGGSLTLSCA ASGDIFTLAS MGWYREDLHK KRELVAQLMS
 61  DGTANYGDSV KGRVTISRDD VDTTVHLRMN TLQPSDTGEY FCYIHTSREI TWGRGTQVTV
121  SQGESSAPQS SAPQATVSSA HHSEDPGPRG LAAAGAPVPY PDPLEPRAA

(48) (SEQ ID NO 67) Nb48
  1  MQAQLAGQLQ LVESGGGLVE VGESLRLSCV ALGFTLDGYA IGWFRQAPGK EREKISCISS
 61  TGDSTNYDDS VKGRFTISRD TAKSTVFLQM NNLIPEDTAI YYCGADLLAR CGRVWYFPPD
121  LNYRGQGTQV TVSSAHHSED PGPRGLAAAG APVPYPDPLE PRAA

SEQ ID NOs 6 to 36 correspond with SEQ ID NOs 37 to 67, respectively.

Example 6. Testing of rSPA-Nb's Lung-Specificity

To further verify the affinity between rSPA-Nb and rat pulmonary surfactant protein A (rSPA), and whether rSPA-Nb has lung-specificity, Western blot and ELISA were used to preliminarily measure the antigen specificity of rSPA-Nb, and immunohistochemistry and in vivo imaging were used to verify its lung-specificity in vivo.

6.1 Western Blot and ELISA

Figure 5A:
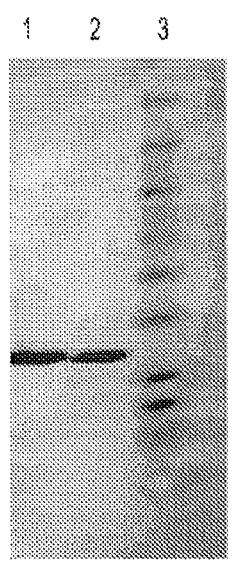
FIG. 5A is Western_Blot: 1, Nb6; 2, NB17.
Figure 5B:
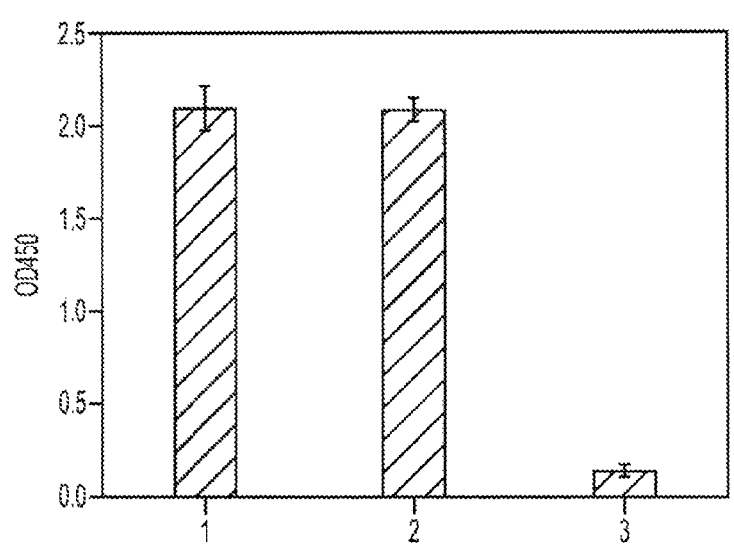
FIG. 5B is ELISA: 1, Nb6; 2, Nb17; 3, negative control group.

Monoclonal antibody against His was chosen as the primary antibody to test the affinity between of purified rSPA-Nb and rSPA using Western blot and ELISA (using the same method described in section 1.2). The results showed that Nb6 and Nb17 had significant binding specificity with rSPA (FIG. 5A, B).

6.2 Immunohistochemistry

Figure 6:
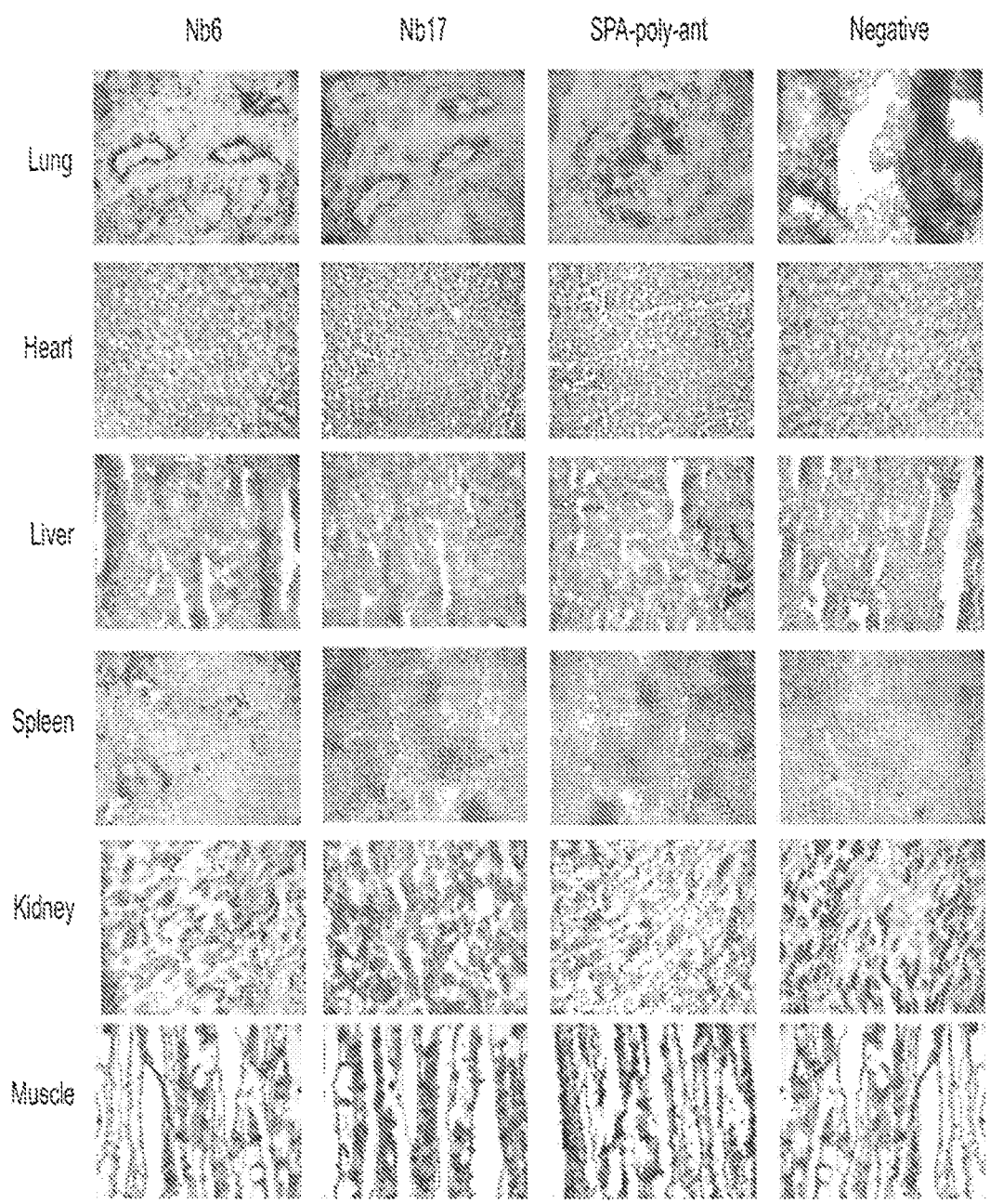
FIG. 6 is a diagram of immunostaining of Nb6 and Nb17 with sliced tissues of rat lung, heart, liver, spleen, muscle.
Figure 7A:
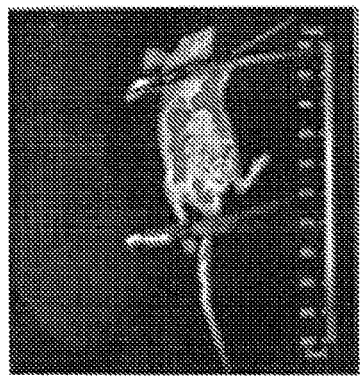
FIG. 7A: 15 minutes after intravenous injection at the tail.
Figure 7B:
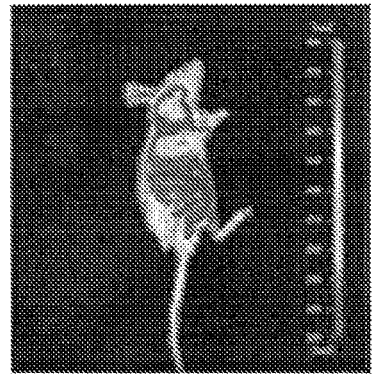
FIG. 7B: 1 hour after intravenous injection at tail.
Figure 7C:
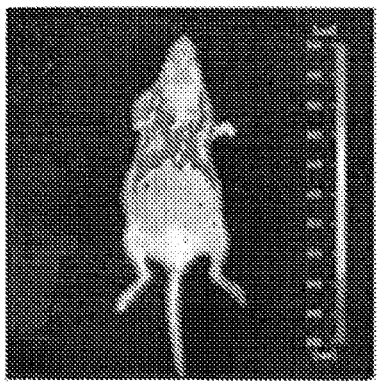
FIG. 7C: 2 hours after intravenous injection at tail.
Figure 7D:
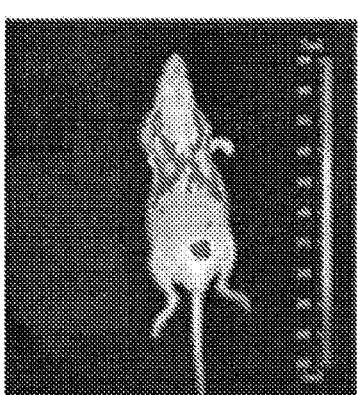
FIG. 7D: 3 hours after intravenous injection at tail.
Figure 7E:
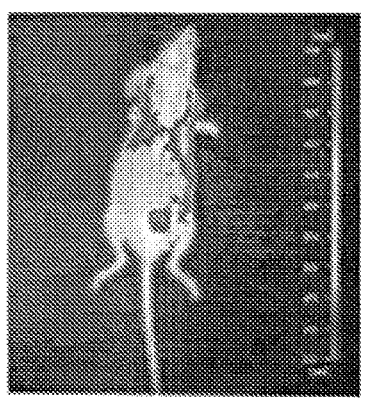
FIG. 7E: 5 hours after intravenous injection at tail.
Figure 7F:
FIG. 7F: 15 minutes after nasal inhalation.

Fresh tissues from the lung, heart, liver, spleen, kidney, muscle of rat were fixed and sliced, and diluted primary antibody (Nb6, Nb17 for the experimental groups, SPA polyclonal antibody (SPA-poly-ant) as a positive control group, and Alliinase as a negative control group) was dropped on. The secondary antibody was HIS-IgG-HRP. The results showed that Nb6, Nb17, and SPA polyclonal antibody (SPA-poly-ant) had significant binding effect with rat lung tissue (shown as brown). The binding effect of Nb17 was similar to that of SPA-poly-ant, while Nb6 had weaker binding effect than Nb17, as there is differences in the amino acid sequence at the antigen binding region between these two. All three antibodies had no obvious binding effect with rat heart, liver, spleen, kidney, muscle tissues, nor had the negative control group (FIG. 6).

6.3 In Vivo Lung-Specificity Testing Using FITC-Marked Nanobody in Mice

Sequence homology analysis showed that there is a high degree of homology between the amino acid sequence of rat and mouse rSPA. Since it is easier to obtain in vivo imaging using nude mice, nude mice were chosen for testing specificity in vivo. Two-week-old nude mice were chosen, and after intraperitoneal anesthesia, 10 ul FITC-labeled nanobody was injected intravenously at the tail, and the dose was 1 mg/kg of the animal body weight. The nude mice were imaged at 15 minutes, 1 hour, 2 hours, 3 hours, and 5 hours after the injection, respectively. At the same time, nasal inhalation was administrated to the positive control group was (FIG. 7). The results showed that 0.5 hours after intravenous injection, the FITC-labeled nanobody began to clearly cluster in the lung. 5 hours after the injection, the clustering in the lung was still obvious, and the lung-targeting effect was similar to that of the nasal inhalation.

The above experiment was repeated using the functional region of the polypeptides of synthetic Nb6 and Nb17 (without the MQAQKAG portion). It was found that the synthetic polypeptides also binds to rSPA with specificity, and are clustered around the lung in in vivo testing.

Example 7. Clone Protein Expression and Targeting Detection

Sequence homology comparative analysis was conducted on the selected 31 sequences, and it was found that Nb16, Nb25, Nb7, and Nb6 had high sequence similarity; Nb17, NB4 and NB2 had the same polypeptide sequence; Nb20, Nb18, Nb12, Nb8 had high sequence similarity; while the rest of the sequences were quite different.

To further verify that the 31 nanobody sequences exhibits lung-targeting affinity with SP-A, 21 clones (excluding those with the same sequence as Nb17) were expressed and purified in accordance with the method described in Examples 5 and 6. Soluble expressions of these nanobodies were obtained, where Nb1 has the least protein expression concentration of 3 mg/L, while the rest of nanobodies have an average protein expression concentration of 8 mg/L.

In Western blot and ELISA, affinity was clearly shown in all 21 proteins, and the OD450 value in ELISA for 7 nanobodies, namely Nb9, Nb11, Nb18, Nb19, Nb36, Nb32, and Nb48, was 5 times greater than that of the negative control group. Immunohistochemical staining showed that these clones had strong affinity. All clones showed significant differences with the negative control group.

In vivo specificity testing in mice showed that seven nanobodies, namely Nb9, NB11, NB18, NB19, Nb36, NB32, and Nb48, had specificity similar to that of Nb17; while there were variations in the clustering effect, all the images exhibited obvious clustering in the lung.

8. rSPA-Nb Construct or Fusion Protein

The rSPA-Nb disclosed above can be linked to a one therapeutic moiety to form a construct or fusion protein that specifically binds to SP-A. Thus, in another aspect, the invention relates to a method for the prevention and/or treatment of lung disease or disorder that can be prevented or treated by the use of a fusion protein or construct as described herein, which method comprises administering, to a subject in need thereof, a pharmaceutically active amount of a fusion protein or construct of the invention, and/or of a pharmaceutical composition comprising the same. The diseases and disorders that can be prevented or treated by the use of a fusion protein or construct as described herein will generally be the same as the diseases and disorders that can be prevented or treated by the use of the therapeutic moiety that is present in the fusion protein or construct of the invention.

The therapeutic moiety can be an immunoglobulin sequence or a fragment thereof. The therapeutic moiety can also be a single domain antibody or an immunoglobulin variable domain sequence. The therapeutic moiety can also be a drug that is effective for treating lung-related diseases. The therapeutic moiety can be directly linked to the rSPA-Nb, or there could be a spacer between the therapeutic moiety and the rSPA-Nb. Nanobodies are very small antibodies molecule with intact antigen-binding ability. Their high stability and solubility, ability to bind epitopes not accessible to conventional antibodies, and rapid tissue penetration make them particular suitable as a target ligand.

Glucocorticoids are considered the most effective anti-inflammatory drug for chronic inflammatory and immune diseases, which are widely used in many pulmonary conditions. such as in asthma, croup (Laryngotracheobronchitis), respiratory distress syndrome (RDS), allergic bronchopulmonaryaspergillosis, interstitial lung disease, hemangioma of trachea, and pulmonary eosinophilic disorders. Glucocorticoids are also used empirically to treat some other conditions, such as idiopathic pulmonary hemosiderosis, bronchiolitis, hypersensitivity pneumonitis, hyperplasia of thymus, bronchiolitis, acute respiratory distress syndrome, aspiration syndromes, atypical pneumonias, laryngeal diphtheria, AIDS, SARS, and sarcoidosis. However, conventional steroids dosage forms are associated with significant adverse effects because of their indiscriminately targeting effects, and the long-term use of high doses of glucocorticoids may lead to side effects such as infection, bleeding, hyperglycemia and ulcers, which limits its clinical application. Hence, there is a need for more efficacious lung-targeting glucocorticoids drug delivery systems.

SP-A nanobodies (SPANbs) can be used as the ligand to prepare active targeting SPA-DXM-NLP to improve treatment efficiency, reduce the systemic side effects, and provide a new method for clinical applications of glucocorticoids.

Poly(lactic-co-glycolic acid) (PLGA) Poly lactic acid (PLA) has been widely used for the encapsulation and sustained delivery of drugs because it is biocompatible, biodegradable, nontoxic, non-immunogenicity, non-carcinogenicity. It is also helpful in controlling the rate of drug release and enhancing drug stability, and is suitable for large scale production. Thus, it can be used as a carrier for SPA-DXM-NLP.

In accordance with an embodiment of the present invention, a SP-A targeting immunonanoliposome was provided, the immunonanoliposome comprises a nanobody against SP-A, a therapeutic moiety, and a nanoliposome, wherein the therapeutic moiety is glucocorticoid. In a preferred embodiment, the therapeutic moiety is dexamethasone sodium phosphate (DXM). The immunonanoliposome has lung-targeting specificity because of the presence of the nanobody against SP-A. The nanoliposome may comprise phospholipids, cholesterol and a liposomes excipient. The liposomes excipients may be distearoyl phosphatidyl ethanolamine-polyethylene glycol 2000 (DSPE-PEG2000) and distearoyl phosphatidyl ethanolamine-polyethylene glycol 2000-pyridyl-associated mercapto-propionate (DSPE-PEG2000-PDP). The phospholipid may be soybean lecithin (SPC), egg yolk lecithin (EPC), and dipalmitoyl phosphatidyl choline (DPPC). The therapeutic moisty may be hydrocortisone, prednisolone, and methylprednisolone.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

In another embodiment, the invention relates to a method for immunotherapy, and in particular for passive immunotherapy, which method comprises administering, to a subject suffering from or at risk of the diseases and disorders mentioned herein, a pharmaceutically active amount of a fusion protein or construct of the invention, and/or of a pharmaceutical composition comprising the same.

The fusion protein or construct and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific nanobody of the invention to be used, the specific route of administration and pharmaceutical formulation or composition to be used, the age, gender, weight, diet, general condition of the patient, and similar factors well known to the clinician.

Generally, the treatment regimen will comprise the administration of one or more fusion proteins or constructs of the invention, or of one or more compositions comprising the same, in one or more pharmaceutically effective amounts or doses. The specific amount(s) or doses to administer can be determined by the clinician, again based on the factors cited above.

Generally, for the prevention and/or treatment of the diseases and disorders mentioned herein and depending on the specific disease or disorder to be treated, the potency and/or the half-life of the specific fusion proteins or constructs to be used, the specific route of administration and the specific pharmaceutical formulation or composition used. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single nanobody of the invention will be used. It is however within the scope of the invention to use two or more Nanobodies of the invention in combination.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

The invention claimed is:

1. An isolated nucleic acid sequence encoding an isolated nanobody comprising an amino acid sequence selected from the group consisting of SEQ ID No: 37 to 67.

2. An isolated polynucleotide sequence comprising any of SEQ ID No: 3 to 36.

3. An isolated polynucleotide sequence encoding an amino acid sequence that can bind to pulmonary surfactant protein A (SP-A), the polynucleotide sequence comprises any of SEQ ID No: 3 to 36.

4. An expression vector comprising the polynucleotide of claim 3.

5. A host cell comprising the vector of claim 4.

* * * * *

```
                              SEQUENCE LISTING

<160> NUMBER OF SEQ ID NOS: 162

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cttggtggtc ctggctgc                                                       18

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtacgtgct gttgaactgt tcc                                                 23

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(41)
<223> OTHER INFORMATION: a, c, t or g
<220> FEATURE:
<221> NAME/KEY: modified_base
<222> LOCATION: (44)..(44)
<223> OTHER INFORMATION: a, c, t or g

<400> SEQUENCE: 3
ccgtggccaa gctggccgkt cagttgcagc tcgtggagtc nggngg                        46

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgtggcctc gggggccggg gtcttcgctg tggtgcg                                  37

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 5
ccgtggcctc gggggccttg tggttttggt gtcttggg        38

<210> SEQ ID NO 6
<211> LENGTH: 468
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgcaggccc agctggccgg tcagttgcag ctcgtggagt ccggggggagg cttggtgcag        60 cctgggggt ctctgaaact ctcctgtaca gcctcagaaa ccacgttcga gatctatccc        120
atggcctggt accgccaggc tccagggaag cagcgcgagt tggtcgcggg cattaatatg        180
atcagtagta caaagtatat agactctgtg aagggccgat tcaccatctc cagagacaac        240
gacaagaaca cgatgtatct gcaaatgaac agcctgaaac tgaggatac ggccgtctat        300 tactgtaatt tagacaccac aatggtggaa ggtgtcgagt actggggcca ggggacccag        360
gtcaccgtct cctccgcgca ccacagcgaa gaccccggcc ccgaggcct tgcggccgca        420 ggtgcgccgg tgccgtatcc ggatccgctg aaccgcgtg ccgcatag        468

<210> SEQ ID NO 7
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgcaggccc agctggccgt tcagttgcag ctcgtggagt caggggagg cttggtgcaa        60 cctgggggt ctctgagact ctcctgtgta gtctctggag tcaccatcag taattatggt        120
atgagctggg tccgccaggc tccgggaaag gggctcgagt ggatctcaac tatttatagt        180
aatggtcaca catactctgc ggactccgtg aagggccgat tcaccatctc cagagacaac        240
gccaagaaca cgctgtatct gcaaatgaac agcctgaaac ctgaggacac ggccaagtat        300
tattgtaaat tggtgggaga gacccaccgg ggccagggga cccaggtcac cgtctcctca        360
gaacccaaga caccaaaaacc acaaggcccc cgaggcttg cggccgcagg tgcgccggtg        420
ccgtatccgg atccgctgga accgcgtgcc gcatag        456

<210> SEQ ID NO 8
<211> LENGTH: 506
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgcaggccc agctggccgt tcagttgcag ctcgtggagt caggggagg cttggtgcaa        60 cctgggggt ctctgagact ctcctgtgta gtctctggag tcaccttcaa taattatggt        120
atgagctggg tccgccaggc tccgggaaag gggctcgagt ggatctcaag tatttatagt        180
aatggtcaca catactctgc ggactccgtg aagggccgat tcaccatctc cagagacaac        240
gccaacaaca ccctgtatct gcaaatgaac agcctgaaac ctgaggacac ggccaactat        300

```
tattgtaaat tggtgggaga gacccaccgg ggccagggga cccaagtcac cgtctcctca    360
gaacccaaca caccaaaacc acaaggcccc cgaggccttg cggccgcagg tgcgccggtg    420
ccgtatccgg atccgctgga accgcgtgcc gcatatactg ttgaaagttg tttagcataa    480
cctcatacag aaaattcatt tactag                                        506
```

<210> SEQ ID NO 9
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgcaggccc agctggccgt tcagttgcag ctcgtggagt caggggggagg cttggtgcaa    60 cctggggggt ctctgagact ctcctgtgta gtctctggag tcaccatcag taattatggt    120
atgagctggg tccgccaggc tccgggaaag gggctcgagt ggatctcaac tatttatagt    180
aatggtcaca catactctgc ggactccgtg aagggccgat tcaccatctc cagagacaac    240
gccaagaaca cgctgtatct gcaaatgaac agcctgaaac ctgaggacac ggccaagtat    300
tattgtaaat tggtgggaga gacccaccgg ggccagggga cccaggtcac cgtctcctca    360
gaacccaaga caccaaaacc acaaggcccc cgaggccttg cggccgcagg tgcgccggtg    420
ccgtatccgg atccgctgga accgcgtgcc gcatag                             456
```

<210> SEQ ID NO 10
<211> LENGTH: 474
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
atgcaggccc agctggccgt tcagttgcag ctcgtggagt cgggagggag gcctggtgca    60
gcctgggggg tctctgagac tctcctgtac agcctccgag atcactttgg attattatgt    120
cataggctgg ttccgccagg ccccagggaa ggagcgtgag cgcctctcat gtattagtaa    180
caatgatgat aatggccaca ttgagccttc cgtcaagggc cgattcgcta tttccagaga    240
cagcgccaag aacacgctgt gtctgcaaat gaacagcctg aaacctgagg acacggccgt    300
gtattactgt gattttggc gtgctatcta taatgggacc atatcactg gggccagggg    360 agccaggtca ccagctcctc agcgcaccac agcgaagacc ccggccccg aggccttgcg    420 gccgcaggtg cgccggtgcc gtatccggat ccgctggaac cgcgtgccgc atag         474
```

<210> SEQ ID NO 11
<211> LENGTH: 467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgttctttc tatgcaggcc cagctggccg gtcagttgca gctcgtggag tctgggggag    60
gcttggtgca acctgggggg tctctgagac tctcctgtgt agtctctgga gtcaccatca    120
gtaattatgg tatgacctgg gtccgccagg ctccgggaaa ggggctcgaa tggatctcaa    180
```

```
ctgtttatag taatggtcac acatactatg cggactccgt gaagggccga ttcaccatct    240
ccagagacaa cgccaagaac acgctgtatc tgcaaatgaa cagcctgaaa cctgaggaca    300
cggccaagta ttattgtaaa ttgacgggag agacccaccg gggccagggg acccaggtca    360
ccgtctcctc agaacccaag acaccaaaac acaaggccc cgaggccttt gcggccgcag     420
gtgcgccggt gccgtatccg gatccgctgg aaccgcgtgc cgcatag                  467

<210> SEQ ID NO 12
<211> LENGTH: 455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgcaggcca gctggccggt cagttgcagc tcgtggagtc tggggaggc ttggtgcaac      60 ctgggggtc tctgatgctc tcctgtgtag tctctggagt caccatcagt aattatggta    120
tgacctgggt ccgccaggct ccgggaaagg ggctcgagtg gatctcaact atttatagta   180
atggtcacac atactatgcg gactccgtga agggccgatt caccgcctcc agagacaacg    240
ccaagaacac gctgtatctg caaatgaaca gcctgaaacc tgaggacacg gccaagtatt    300
attgtaaatt gacgggagag acccaccggg gccaggggac ccaggtcacc gtctcctcag    360
aacccaagac accaaaacca caggccccc gaggccttgc ggccgcaggt gcgccggtgc     420
cgtatccgga tccgctggaa ccgcgtgccg catag                               455

<210> SEQ ID NO 13
<211> LENGTH: 511
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgtcctttc atgcaggccc agctggccgg tcagttgcag ctcgtggagt ctggggagg     60 cttggtgcag cctggggggt ctctgagact ctcctgtaca gcctctgaat tcactttgga   120
ttaccattcc ataggctggt ccgccaggc cccaggaag gagcgtgagg gggtctcatg     180
tattagttat ggtgatggta ccacatttta tacagactcc gtgaagggcc gattcaccat    240
ctccagagac aacgccaaga acacggtgac tctgcaaatg aacagcctga acctgagga    300 cacagccgtt tattactgtg cagcatcacc cggtcgatta ctattgttca ggctatgtat    360
gtccgaggat gaatatgact tttgggggcca ggggacccag gtcaccgtct cctcagaacc   420
caagacacca aaaccacaag gccccgagg ccttgcggcc gcaggtgcgc cggtgccgta    480
tccggatccg ctggaaccgc gtgccgcata g                                   511

<210> SEQ ID NO 14
<211> LENGTH: 506
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgcaggccc agctggccgg tcagttgcag ctcgtggagt ccggggagg cttggtgcaa     60
```

```
cctgggggt ctctgagact ctcctgtgta gtctctggag tcaccttcaa taattatggt    120
atgacctggg tccgccaggc tccgggaaag gggctcgagt ggatctcaac tatttatagt    180
aatggtcaca catactatgc ggacttcgtg aagggccgat tcaccatctc cagagacaac    240
gccaagaaca cgttgtatct gcaaatgatc agcctgaaac ctgaggacac ggccaagtat    300
tattgtagat tgacgggaga gacctaccgg ggccagggga cccaggtcac cgtctcctca    360
gaacccaaga cacgaaaacc acaaggcccc cgaggccttg cggccgcagg tgcgccggtg    420
ccgtatccgg atccgctgga accgcgtgcc gcatatactg ttgaaagttg tttagcaaaa    480
cctcatacag aaaattcatt tactag                                        506
```

```
<210> SEQ ID NO 15
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgcaggccc agctggccgg tcagttgcag ctcgtggagt ctgggggagg cttggtgcaa     60 cctgggggt ctctgatgct ctcctgtgta gtctctggag tcaccatcag taattatggt    120
atgacctggg tccgccaggc tccgggaaag gggctcgagt ggatctcaac tatttatagt    180
aatggtcaca catactatgc ggactccgtg aagggccgat tcaccgcctc cagagacaac    240
gccaagaaca cgctgtatct gcaaatgaac agcctgaaac ctgaggacac ggccaagtat    300
tattgtaaat tgacgggaga gacccaccgg ggccagggga cccaggtcac cgtctcctca    360
gaacccaaga caccaaaacc acaaggcccc cgaggccttg cggccgcagg tgcgccggtg    420
ccgtatccgg atccgctgga accgcgtgcc gcatag                             456
```

```
<210> SEQ ID NO 16
<211> LENGTH: 561
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgcaggccc agctggccgt tcagttgcag ctcgtggagt ctgggggagg cttggtgcaa     60 cctgggggt ctctgagact ctcctgtgca gcctctggaa tcatcttgaa tttctatggg    120
atgggctggg accgccagac tccaggccag gggctcgagg ggtctcata tgttaataat    180 aatggtatga caaactatgc agactccgtg aagggccgat tcaccatctc cagagacaac    240
gccaagaaca caatgtatct gcaaatgaac agcctgaaac ctgaggacac ggccgactat    300
tactgtaatg tgagtgcata cacctatagg agtaattact actacccctg gggccaggca    360
aaccacgtca cagtctcatc acaacgcaag acacgaaaag cacaaggacg cgcacgcctt    420
gcggacgcag gtgcgccggt gccgcatgcc gatcagatgg aacaacgtgc ctcataaact    480
gttgaaagtt gtttatcaaa tcctcatata taaaattaat atacaaattt ctataaatac    540
gataaatctt aagatcgtta g                                             561
```

```
<210> SEQ ID NO 17
<211> LENGTH: 456
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 17

```
atgcaggccc agctggccgg tcagttgcag ctcgtggagt ctggggggagg cttggtgcaa     60
cctgggggt ctctgagact ctcctgtgta gtctctggag tcaccatcag taattatggt     120
atgacctggg tccgccaggc tccgggaaag gggctcgaat ggatctcaac tgtttatagt    180
aatggtcaca catactatgc ggactccgtg aagggccgat tcaccatctc cagagacaac    240
gccaagaaca cgctgtatct gcaaatgaac agcctgaaac tgaggacac ggccaagtat    300
tattgtaaat tgacgggaga gacccaccgg ggccagggga cccaggtcac cgtctcctca    360
gaacccaaga caccaaaacc acaaggcccc cgaggccttg cggccgcagg tgcgccggtg    420
ccgtatccgg atccgctgga accgcgtgcc gcatag                              456
```

<210> SEQ ID NO 18
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atgcaggccc agctggccgt tcagttgcag ctcgtggagt caggggggagg cttggtgcaa     60
cctgggggt ctctgagact ctcctgtgta gtctctggag tcaccatcag taattatggt     120
atgagctggg tccgccaggc tccgggaaag gggctcgagt ggatctcaac tatttatagt    180
aatggtcaca catactctgc ggactccgtg aagggccgat tcaccatctc cagagacaac    240
gccaagaaca cgctgtatct gcaaatgaac agcctgaaac tgaggacac ggccaagtat    300
tattgtaaat tggtgggaga gacccaccgg ggccagggga cccaggtcac cgtctcctca    360
gaacccaaga caccaaaacc acaaggcccc cgaggccttg cggccgcagg tgcgccggtg    420
ccgtatccgg atccgctgga accgcgtgcc gcatag                              456
```

<210> SEQ ID NO 19
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atgcaggccc agctggccgg tcagttgcag ctcgtggagt ctggggggagg cttggtgcaa     60
cctgggggt ctctgatgct ctcctgtgta gtctctggag tcaccatcag taattatggt     120
atgacctggg tccgccaggc tccgggaaag gggctcgagt ggatctcaac tatttatagt    180
aatggtcaca catactatgc ggactccgtg aagggccgat tcaccgcctc cagagacaac    240
gccaagaaca cgctgtatct gcaaatgaac agcctgaaac tgaggacac ggccaagtat    300
tattgtaaat tgacgggaga gacccaccgg ggccagggga cccaggtcac cgtctcctca    360
gaacccaaga caccaaaacc acaaggcccc cgaggccttg cggccgcagg tgcgccggtg    420
ccgtatccgg atccgctgga accgcgtgcc gcatag                              456
```

<210> SEQ ID NO 20
<211> LENGTH: 334

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

| atgtattagt tatggtgatg gtaccacatt ttatacagac tccgtgaagg gccgattcac | 60 |
| catctccaga gacaacgcca agaacacggt gactctgcaa atgaacagcc tgaaacctga | 120 |
| ggacacagcc gtttattact gtgcagcatc acccggtcga ttactattgt tcaggctatg | 180 |
| tatgtccgag gatgaaatatg acttttgggg ccaggggacc caggtcaccg tctcctcaga | 240 |
| acccaagaca ccaaaaccac aaggcccccg aggccttgcg ccgcaggtg cgccggtgcc | 300 |
| gtatccggat ccgctggaac cgcgtgccgc atag | 334 |

<210> SEQ ID NO 21
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

| atgcaggccc agctggccgt tcagttgcag ctcgtggagt cggggggagg cttggtgcaa | 60 |
| cctgggggt ctctgatgct ctcctgtgta gtctctggag tcaccatcag taattatggt | 120 |
| atgacctggg tccgccaggc tccgggaaag gggctcgagt ggatctcaac tatttatagt | 180 |
| aatggtcaca catactatgc ggactccgtg aagggccgat tcaccgcctc cagagacaac | 240 |
| gccaagaaca cgctgtatct gcaaatgaac agcctgaaac ctgaggacac ggccaagtat | 300 |
| tattgtaaat tgacgggaga gacccaccgg ggccagggga cccaggtcac cgtctcctca | 360 |
| gaacccaaga caccaaaaacc acaaggcccc gaggccttg cggccgcagg tgcgccggtg | 420 |
| ccgtatccgg atccgctgga accgcgtgcc gcatag | 456 |

<210> SEQ ID NO 22
<211> LENGTH: 471
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

| atgcaggccc agctggccgg tcagttgcag ctcgtggagt ctgggggagg cttggtgcag | 60 |
| cctgggggt ctctgagact ctcctgtgca gcctccggaa gagccttcag tgtgtatgcc | 120 |
| gtgggctggt atcgccagcc tccagggaag cagcgcgagc tggtcgcgag tatcactgat | 180 |
| ggtggaagca caaactatgc agactcggtg aagggccgat tcaccgtctc cagagacaac | 240 |
| gccagaaata cggcgtacct ggatatgaac agcctgaaag ttgaggacac ggccgtctat | 300 |
| tactgtaatg caaattatgg gggtagtgtc ctatacaact actggggccc gggaacccaa | 360 |
| gtcaccgtct ccacagaacc caagacacca aaaccacaag ccccgagg ccttgcggcc | 420 |
| gcaggtgcgc cggtgccgta tccggatccg ctggaaccgc gtgccgcata g | 471 |

<210> SEQ ID NO 23
<211> LENGTH: 456
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23

```
atgcaggccc agctggccgg tcagttgcag ctcgtggagt ctgggggagg cttggtgcaa      60
cctggggggt ctctgagact ctcctgtgta gtctctggag tcaccatcag taattatggt     120
atgacctggg tccgccaggc tccgggaaag gggctcgaat ggatctcaac tgtttatagt     180
aatggtcaca catactatgc ggactccgtg aagggccgat tcaccatctc cagagacaac     240
gccaagaaca cgctgtatct gcaaatgaac agcctgaaac tgaggacac ggccaagtat      300
tattgtaaat tgacgggaga gacccaccgg ggccagggga cccaggtcac cgtctcctca     360
gaacccaaga caccaaaacc acaaggcccc cgaggccttg cggccgcagg tgcgccggtg     420
ccgtatccgg atccgctgga accgcgtgcc gcatag                                456
```

<210> SEQ ID NO 24
<211> LENGTH: 465
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24

```
atgcaggccc agctggccgt tcagttgcag ctcgtggagt caggggggagg cttggtgcag     60
cctggggggt ctctgagact ctcctgtgaa gtctctggaa gcagaggcag tatctatttc    120
tcgggctggt accgccaggc tccagggaag cagcgcgagt tggtcgcaag tattactagt    180
ggtggtacta caaattatgc agactccgtg aagggccgat tcaccatctc cagagacaac    240
gccaagaaca cggtgtatct gcaaatgaac agcctgaaac tgaggacac ggccgtctat     300
tactgtaata taggtcgata cggattgggc gggtcctggg gtcaggggac ccaggtcacc    360
gtctcctcag aacccaagac accaaaacca caaggccccc gaggccttgc ggccgcaggt    420
gcgccggtgc cgtatccgga tccgctggaa ccgcgtgccg catag                     465
```

<210> SEQ ID NO 25
<211> LENGTH: 489
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25

```
atgcaggccc agctggccgg tcagttgcag ctcgtggagt ccggtggagg cttggtgcag     60
cctggggggt ctctgagact ctcctgtgaa gcctctggct tcactttcga cgattatgcc    120
ataggctggt tccgccaggc cccagggaag gagcgtgagg aggtctcatg tattagtcat    180
aatggaggta ccacaaacta tgcagactcc gtgaagggcc gattctccat ctccagagac    240
aacgccaaga acacggtgta tctgcaaatg aacgcctga  aacctgagga cacagccaac    300
tattactgtg caggcgcgcg ttccggacta tgtgtgtttt ttgagttgca agattatgac    360
tactggggcc aggggaccca ggtcaccgtc tcctcagcgc accacagcga agaccccggc    420
ccccgaggcc ttgcggccgc aggtgcgccg gtgccgtatc cggatccgct ggaaccgcgt    480
gccgcatag                                                              489
```

<210> SEQ ID NO 26
<211> LENGTH: 532
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atgcaggccc agccggccgt cctggctgct cttctacaag gtgtccaggc tcaggtgaag      60
ctggtggagt ctgggggagg ctcggtgcag gctggagggt ctctgagact ctcctgtaca     120
gcctctggat cagactacag atggatgtac atcgcccgt  ttcgccaatg ccagggaag     180
gagcgcgagg gggtcgcagc aatttatact gatgatactg atgatagtag tccgatctat     240
gccacctccg ccaagggccg attcaccatc tcccaagaca aggacaagaa cgcggtatat     300
ctgcaaatga acagcccgaa acctgaggac actgccatgt actactgtgc ggcaagagcg     360
ttcggtggta cctggagctt gagctccccg gacgacttta gtgcctgggg ccaggggacc     420
caggtcaccg tctcctcagg aacgaatgaa gtatgcaagt ggcccccgag gccttgcggc     480
cgcaggtgcg ccggtgccgt atccggatcc gctggaaccg cgtgccgcat ag            532
```

<210> SEQ ID NO 27
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atgcaggccc agctggccgg tcagttgcag ctcgtggagt ctgggggagg cttggtgcag      60
cctgggggt  ctctgagact ctcctgtaca gcctctaaat tccatttgga ttcttatgcc     120
gtagcctggt tccgccagac cccagggaag gagcgtgagg cggtctcatt tataaatact     180
agtgatgatg tcacatactt tgctgactcc gtaaagggcc gattcaccat ctccagagac     240
aactccaaga cacggtata  tctgcaaatg aacgtcctga accagaagaa cacttccgtt     300
tatgtgtgtg cagcggtaag aagtcccggc cctaccggcc ctagtatgca gcctatgtgg     360
tcggtgcctg acctgtatga ctactggggc caggggaccc aggtcaccgt ctcctcagcg     420
caccacagcg aagaccccgg cccccgaggc cttgcggccg caggtgcgcc ggtgccgtat     480
ccggatccgc tggaaccgcg tgccgcatag                                      510
```

<210> SEQ ID NO 28
<211> LENGTH: 471
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
atgcaggccc agctggccgt tcagttgcag ctcgtggagt ccggtggagg cacggtgcag      60
cctgggggt  ctctgaacct ctcctgtgta acttctggat tcaccttcag taggcatgat     120
atgagttggg tccgccaggc tccagggaag gggcccgagt ggatctcagg tattggtact     180
agtggtacaa gcggacgtta tgcgagctcc gtgaagggcc gattcaccat ctccagagac     240
aacgccaaga tacgctgta  tctccaaatg gatagcctga aacctgaaga cacgggccta     300
tattactgca cgaccggcgg cgtttatagc gcctatgtac aaccccgggg caaggggacg     360
```

```
caggtcaccg tctcctcggc gcaccacagc gaagacccca gccccgagg ccttgcggcc    420 gcaggtgcgc cggtgccgta tccggatccg ctggaaccgc gtgccgcata g            471
```

<210> SEQ ID NO 29
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atgcaggccc agctggccgt tcagttgcag ctcgtggagt cgggtggagg cttggtgcag    60 cctgggggt ctctgagact ctcctgtgca gcctccggaa gagccttcag tgtgtatgcc    120
gtgggctggt accgccagat tccagggaat cagcgcgaaa tggtcgcagc tattagtagc    180
ggtggtaaca caaatactc ggactccgtg aagggccgct tcaccgtctc ctcagaaccc    240
aagacaccaa aaccacaagg cccccgaggc cttgcggccg caggtgcgcc ggtgccgtat    300
ccggatccgc tggaaccgcg tgccgcatag                                    330
```

<210> SEQ ID NO 30
<211> LENGTH: 532
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
atgcaggccc agccggccgt cctggctgct cttctacaag gtgtccaggc tcaggtgaag    60
ctggtggagt ctgggggagg ctcggtgcag gctggagggt ctctgagact ctcctgtaca    120
gcctctggat cagactacag atggatgtac atcgcccgt tcgccaatg tccagggaag    180 gagcgcgagg gggtcgcagc aatttatact gatgatactg atgatagtag tccgatctat    240
gccacctccg ccaagggccg attcaccatc tcccaagaca aggacaagaa cgcggtatat    300
ctgcaaatga acagcccgaa acctgaggac actgccatgt actactgtgc ggcaagagcg    360
ttcggtggta cctggagctt gagctccccg gacgacttta gtgcctgggg ccaggggacc    420
caggtcaccg tctcctcagg aacgaatgaa gtatgcaagt ggcccccgag gccttgcggc    480
cgcaggtgcg ccggtgccgt atccggatcc gctggaaccg cgtgccgcat ag           532
```

<210> SEQ ID NO 31
<211> LENGTH: 494
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
atgcaggccc agctggccgg tcagttgcag ctcgtggagt cgggtggagg catggtgcag    60 cctgggggt ctctgagact ctcctgtgca gcctctggat tcattttcag tgctatgac    120 atgggttggg tccgccaaac tccagggaag gggcgcgagt gggtctcagg tattaattct    180
ggtggtgggc gtacatacta tgcggactcc gtgaagggcc gattcaccat ctccagagac    240
gacgataagc tacgttgta tttgtcaatg gacggcctga aacctgagga cacggccctg    300
taccattgtg tgagattcac cgtgaaaacg ccgcaaggtt actactacct gaacgatttc    360
```

```
gactactggg gccagggac ccaggtcacc gtctcctccg aacccaagac accaaaacca    420
caaggccccc gaggccttgc ggccgcaggt gcgccggtgc cgtatccgga tccgctggaa    480
ccgcgtgccg cata                                                      494
```

<210> SEQ ID NO 32
<211> LENGTH: 483
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atgcaggccc agctggccgg tcagttgcag ctcgtggagt ctgggggagg cttggtgcag    60 attgggggt ctctgagact ctcctgtgca gcctctggaa gcgacttcag tatctatcac     120
atgggctggt accgccaggc tccagggaag cagcgcgagt tggtcgcagc tattactagt    180
ggtggtagca caaactatgc agactccgtg aagggccgat tcaccatctc cagtgacaac    240
gccaagaaca cggtgtatct gcaaatgaac agcctgaaac tgaggacac ggccgtctat     300 tattgtaatg cagatggggt ccccgagtat agcgactatg cctccggccc ggtgtactgg    360
ggccagggga cccaggtcac cgtctcctca gcgcaccaca gcgaagaccc cggcccccga    420
ggccttgcgg ccgcaggtgc gccggtgccg tatccggatc cgctggaacc gcgtgccgca    480
tag                                                                  483
```

<210> SEQ ID NO 33
<211> LENGTH: 468
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
atgcaggccc agctggccgt tcagttgcag ctcgtggagt cgggtggagg cttggtgcag    60 gctgggggt ctctgagact gtcctgtgtg gcctctggaa gtatgttcaa tttctatggc     120
atggcctggt accggcaggc tccagggaag cagcgcgagt tggtcgcatc aattgatagt    180
gagggtagaa cgacaaacta tccagactcc ctgaagggcc gattcaccat ctccagggac    240
gacgccaaga gcacggcgta tctgcaaatg aacaacctga ttcctgacga cacggccgtc    300
tattactgta tgccttccg agggaggatg tatgactact ggggccaggg gacccaggtc     360
accgtctcct cagaacccaa gacaccaaaa ccacaaggcc ccgaggcct gcggccgca     420 ggtgcgccgg tgccgtatcc ggatccgctg aaccgcgtg ccgcatag                  468
```

<210> SEQ ID NO 34
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atgcaggccc agctggccgg tcagttgcag ctcgtggagt ctggtggaag gttggttgca    60
cccgggaggt ctttgaaact ctcccggacc ttctctggtc tctatttgca ttcaagtgcc    120
tttggctggt tccccacgt tcccagggaa gcgcgtgaag gggttgcctt cctttgtaat     180
```

```
tccggttctg acccaatata tttacacccc gagaagggca ttttcactct ctccagacac    240
tgtgtcaaat gaacggtttc tccgtttgag gacaacgata ctgtagaaca caccccctact    300 tatcagtgcc aacacatct ag                                              322
```

<210> SEQ ID NO 35
<211> LENGTH: 510
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
atgcaggccc agctggccgg tcagttgcag ctcgtggagt cgggtggagg cagggtgcag     60 gctgggggt ctctgacact ctcctgtgca gcctctggag acatcttcac tctcgcttcc    120
atgggatggt atcgtgaaga tctacacaaa aagcgcgagt tggtggccca actgatgagt    180
gatggtaccg cgaattatgg agattccgtg aagggccgat caccatctc agagacgac     240 gtcgatacca cagtgcatct gcgaatgaat accctgcaac cgtccgacac gggagaatat    300
ttttgttata tccatacttc ccgcgaaatt acctggggcc ggggaccca ggtcaccgtc     360 tcccagggag agtcctcggc gcctcagtcc tcggcgcctc aggccaccgt ctcctcggcg    420
caccacagcg aagaccccgg ccccgaggc cttgcggccg caggtgcgcc ggtgccgtat     480
ccggatccgc tggaaccgcg tgccgcatag                                     510
```

<210> SEQ ID NO 36
<211> LENGTH: 495
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atgcaggccc agctggccgg tcagttgcag ctcgtggagt ctggggggagg cctggtcgaa     60 gttggggagt ctctgagact ctcctgtgta gcactcggat tcactttgga cgggtatgcc    120
attggctggt tccgccaggc cccggggaag gagcgtgaga aaatctcatg cattagtagt    180
actggcgata gtacaaatta tgatgactcc gtgaagggcc gattcaccat ctccagagac    240
actgccaaga gcacggtgtt tctgcaaatg aacaacctga tacctgagga cacagccatt    300
tattactgtg cgcagacct cttggcgcgg tgtggtcgtg tttggtactt ccgccgac      360 cttaattacc ggggccaggg gacccaggtc accgtttctt cagcgcacca cagcgaagac    420
cccgcccccc gaggccttgc ggccgcaggt gcgccggtgc cgtatccgga tccgctggaa    480
ccgcgtgccg catag                                                    495
```

<210> SEQ ID NO 37
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Met Gln Ala Gln Leu Ala Gly Gln Leu Gln Leu Val Glu Ser Gly Gly
1               5                   10                  15
```

```
Gly Leu Val Gln Pro Gly Gly Ser Leu Lys Leu Ser Cys Thr Ala Ser
            20                  25                  30

Glu Thr Thr Phe Glu Ile Tyr Pro Met Ala Trp Tyr Arg Gln Ala Pro
            35                  40                  45

Gly Lys Gln Arg Glu Leu Val Ala Gly Ile Asn Met Ile Ser Ser Thr
50                  55                  60

Lys Tyr Ile Asp Ser Val Lys Gly Arg Phe Thr Ile Ser Arg Asp Asn
65                  70                  75                  80

Asp Lys Asn Thr Met Tyr Leu Gln Met Asn Ser Leu Lys Pro Glu Asp
            85                  90                  95

Thr Ala Val Tyr Tyr Cys Asn Leu Asp Thr Thr Met Val Glu Gly Val
            100                 105                 110

Glu Tyr Trp Gly Gln Gly Thr Gln Val Thr Val Ser Ser Ala His His
            115                 120                 125

Ser Glu Asp Pro Gly Pro Arg Gly Leu Ala Ala Ala Gly Ala Pro Val
            130                 135                 140

Pro Tyr Pro Asp Pro Leu Glu Pro Arg Ala Ala
145                 150                 155

<210> SEQ ID NO 38
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gln Ala Gln Leu Ala Val Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Ile Ser Asn Tyr Gly Met Ser Trp Val Arg Gln Ala Pro
            35                  40                  45

Gly Lys Gly Leu Glu Trp Ile Ser Thr Ile Tyr Ser Asn Gly His Thr
50                  55                  60

Tyr Ser Ala Asp Ser Val Lys Gly Arg Phe Thr Ile Ser Arg Asp Asn
65                  70                  75                  80

Ala Lys Asn Thr Leu Tyr Leu Gln Met Asn Ser Leu Lys Pro Glu Asp
            85                  90                  95

Thr Ala Lys Tyr Tyr Cys Lys Leu Val Gly Glu Thr His Arg Gly Gln
            100                 105                 110

Gly Thr Gln Val Thr Val Ser Ser Glu Pro Lys Thr Pro Lys Pro Gln
            115                 120                 125

Gly Pro Arg Gly Leu Ala Ala Ala Gly Ala Pro Val Pro Tyr Pro Asp
            130                 135                 140

Pro Leu Glu Pro Arg Ala Ala
145                 150

<210> SEQ ID NO 39
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

Met Gln Ala Gln Leu Ala Val Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Phe Asn Asn Tyr Gly Met Ser Trp Val Arg Gln Ala Pro
            35                  40                  45

Gly Lys Gly Leu Glu Trp Ile Ser Ser Ile Tyr Ser Asn Gly His Thr
        50                  55                  60

Tyr Ser Ala Asp Ser Val Lys Gly Arg Phe Thr Ile Ser Arg Asp Asn
65                  70                  75                  80

Ala Asn Asn Thr Leu Tyr Leu Gln Met Asn Ser Leu Lys Pro Glu Asp
                85                  90                  95

Thr Ala Asn Tyr Tyr Cys Lys Leu Val Gly Glu Thr His Arg Gly Gln
            100                 105                 110

Gly Thr Gln Val Thr Val Ser Ser Glu Pro Asn Thr Pro Lys Pro Gln
            115                 120                 125

Gly Pro Arg Gly Leu Ala Ala Ala Gly Ala Pro Val Pro Tyr Pro Asp
        130                 135                 140

Pro Leu Glu Pro Arg Ala Ala Tyr Thr Val Glu Ser Cys Leu Ala
145                 150                 155

<210> SEQ ID NO 40
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gln Ala Gln Leu Ala Val Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Ile Ser Asn Tyr Gly Met Ser Trp Val Arg Gln Ala Pro
            35                  40                  45

Gly Lys Gly Leu Glu Trp Ile Ser Thr Ile Tyr Ser Asn Gly His Thr
        50                  55                  60

Tyr Ser Ala Asp Ser Val Lys Gly Arg Phe Thr Ile Ser Arg Asp Asn
65                  70                  75                  80

Ala Lys Asn Thr Leu Tyr Leu Gln Met Asn Ser Leu Lys Pro Glu Asp
                85                  90                  95

Thr Ala Lys Tyr Tyr Cys Lys Leu Val Gly Glu Thr His Arg Gly Gln
            100                 105                 110

Gly Thr Gln Val Thr Val Ser Ser Glu Pro Lys Thr Pro Lys Pro Gln
            115                 120                 125

Gly Pro Arg Gly Leu Ala Ala Ala Gly Ala Pro Val Pro Tyr Pro Asp
        130                 135                 140

Pro Leu Glu Pro Arg Ala Ala
145                 150

<210> SEQ ID NO 41
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 41

Leu Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Ile Ser Asn Tyr Gly Met Thr Trp Val Arg Gln Ala Pro
        35                  40                  45

Gly Lys Gly Leu Glu Trp Ile Ser Thr Val Tyr Ser Asn Gly His Thr
    50                  55                  60

Tyr Tyr Ala Asp Ser Val Lys Gly Arg Phe Thr Ile Ser Arg Asp Asn
65                  70                  75                  80

Ala Lys Asn Thr Leu Tyr Leu Gln Met Asn Ser Leu Lys Pro Glu Asp
                85                  90                  95

Thr Ala Lys Tyr Tyr Cys Lys Leu Thr Gly Glu Thr His Arg Gly Gln
            100                 105                 110

Gly Thr Gln Val Thr Val Ser Ser Glu Pro Lys Thr Pro Lys Pro Gln
        115                 120                 125

Gly Pro Arg Gly Leu Ala Ala Gly Ala Pro Val Pro Tyr Pro Asp
    130                 135                 140

Pro Leu Glu Pro Arg Ala Ala
145                 150

<210> SEQ ID NO 42
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Ile Ser Asn Tyr Gly Met Thr Trp Val Arg Gln Ala Pro
        35                  40                  45

Gly Lys Gly Leu Glu Trp Ile Ser Thr Val Tyr Ser Asn Gly His Thr
    50                  55                  60

Tyr Tyr Ala Asp Ser Val Lys Gly Arg Phe Thr Ile Ser Arg Asp Asn
65                  70                  75                  80

Ala Lys Asn Thr Leu Tyr Leu Gln Met Asn Ser Leu Lys Pro Glu Asp
                85                  90                  95

Thr Ala Lys Tyr Tyr Cys Lys Leu Thr Gly Glu Thr His Arg Gly Gln
            100                 105                 110

Gly Thr Gln Val Thr Val Ser Ser Glu Pro Lys Thr Pro Lys Pro Gln
        115                 120                 125

Gly Pro Arg Gly Leu Ala Ala Gly Ala Pro Val Pro Tyr Pro Asp
    130                 135                 140

Pro Leu Glu Pro Arg Ala Ala
145                 150

<210> SEQ ID NO 43
<211> LENGTH: 146
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 43

Ala Gly Gln Leu Gln Leu Val Glu Ser Gly Gly Leu Val Gln Pro
1               5                   10                  15

Gly Gly Ser Leu Met Leu Ser Cys Val Val Ser Gly Val Thr Ile Ser
            20                  25                  30

Asn Tyr Gly Met Thr Trp Val Arg Gln Ala Pro Gly Lys Gly Leu Glu
        35                  40                  45

Trp Ile Ser Thr Ile Tyr Ser Asn Gly His Thr Tyr Tyr Ala Asp Ser
    50                  55                  60

Val Lys Gly Arg Phe Thr Ala Ser Arg Asp Asn Ala Lys Asn Thr Leu
65                  70                  75                  80

Tyr Leu Gln Met Asn Ser Leu Lys Pro Glu Asp Thr Ala Lys Tyr Tyr
                85                  90                  95

Cys Lys Leu Thr Gly Glu Thr His Arg Gly Gln Gly Thr Gln Val Thr
            100                 105                 110

Val Ser Ser Glu Pro Lys Thr Pro Lys Pro Gln Gly Pro Arg Gly Leu
        115                 120                 125

Ala Ala Ala Gly Ala Pro Val Pro Tyr Pro Asp Pro Leu Glu Pro Arg
    130                 135                 140

Ala Ala
145

<210> SEQ ID NO 44
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Thr Ala Ser
            20                  25                  30

Glu Phe Thr Leu Asp Tyr His Ser Ile Gly Trp Phe Arg Gln Ala Pro
        35                  40                  45

Gly Lys Glu Arg Glu Gly Val Ser Cys Ile Ser Tyr Gly Asp Gly Thr
    50                  55                  60

Thr Phe Tyr Thr Asp Ser Val Lys Gly Arg Phe Thr Ile Ser Arg Asp
65                  70                  75                  80

Asn Ala Lys Asn Thr Val Thr Leu Gln Met Asn Ser Leu Lys Pro Glu
                85                  90                  95

Asp Thr Ala Val Tyr Tyr Cys Ala Ala Ser Pro Gly Arg Leu Leu Leu
            100                 105                 110

Phe Arg Leu Cys Met Ser Glu Asp Glu Tyr Asp Phe Trp Gly Gln Gly
        115                 120                 125

Thr Gln Val Thr Val Ser Ser Pro Lys Thr Pro Lys Pro Gln Gly
    130                 135                 140

Pro Arg Gly Leu Ala Ala Ala Gly Ala Pro Val Pro Tyr Pro Asp Pro
145                 150                 155                 160

Leu Glu Pro Arg Ala Ala
                165
```

<210> SEQ ID NO 45
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Phe Asn Asn Tyr Gly Met Thr Trp Val Arg Gln Ala Pro
        35                  40                  45

Gly Lys Gly Leu Glu Trp Ile Ser Thr Ile Tyr Ser Asn Gly His Thr
    50                  55                  60

Tyr Tyr Ala Asp Phe Val Lys Gly Arg Phe Thr Ile Ser Arg Asp Asn
65                  70                  75                  80

Ala Lys Asn Thr Leu Tyr Leu Gln Met Ile Ser Leu Lys Pro Glu Asp
                85                  90                  95

Thr Ala Lys Tyr Tyr Cys Arg Leu Thr Gly Glu Thr Tyr Arg Gly Gln
            100                 105                 110

Gly Thr Gln Val Thr Val Ser Ser Glu Pro Lys Thr Arg Lys Pro Gln
        115                 120                 125

Gly Pro Arg Gly Leu Ala Ala Ala Gly Ala Pro Val Pro Tyr Pro Asp
    130                 135                 140

Pro Leu Glu Pro Arg Ala Ala
145                 150

<210> SEQ ID NO 46
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Gln Ala Gln Leu Ala Gly Gln Leu Gln Leu Val Glu Ser Gly Gly
1               5                   10                  15

Gly Leu Val Gln Pro Gly Gly Ser Leu Met Leu Ser Cys Val Val Ser
            20                  25                  30

Gly Val Thr Ile Ser Asn Tyr Gly Met Thr Trp Val Arg Gln Ala Pro
        35                  40                  45

Gly Lys Gly Leu Glu Trp Ile Ser Thr Ile Tyr Ser Asn Gly His Thr
    50                  55                  60

Tyr Tyr Ala Asp Ser Val Lys Gly Arg Phe Thr Ala Ser Arg Asp Asn
65                  70                  75                  80

Ala Lys Asn Thr Leu Tyr Leu Gln Met Asn Ser Leu Lys Pro Glu Asp
                85                  90                  95

Thr Ala Lys Tyr Tyr Cys Lys Leu Thr Gly Glu Thr His Arg Gly Gln
            100                 105                 110

Gly Thr Gln Val Thr Val Ser Ser Glu Pro Lys Thr Pro Lys Pro Gln
        115                 120                 125

Gly Pro Arg Gly Leu Ala Ala Ala Gly Ala Pro Val Pro Tyr Pro Asp
    130                 135                 140

```
Pro Leu Glu Pro Arg Ala Ala
145                 150

<210> SEQ ID NO 47
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Gln Ala Gln Leu Ala Val Gln Leu Gln Leu Val Glu Ser Gly Gly
1               5                   10                  15

Gly Leu Val Gln Pro Gly Gly Ser Leu Arg Leu Ser Cys Ala Ala Ser
            20                  25                  30

Gly Ile Ile Leu Asn Phe Tyr Gly Met Gly Trp Asp Arg Gln Thr Pro
        35                  40                  45

Gly Gln Gly Leu Glu Gly Val Ser Tyr Val Asn Asn Asn Gly Met Thr
    50                  55                  60

Asn Tyr Ala Asp Ser Val Lys Gly Arg Phe Thr Ile Ser Arg Asp Asn
65                  70                  75                  80

Ala Lys Asn Thr Met Tyr Leu Gln Met Asn Ser Leu Lys Pro Glu Asp
                85                  90                  95

Thr Ala Asp Tyr Tyr Cys Asn Val Ser Ala Tyr Thr Tyr Arg Ser Asn
            100                 105                 110

Tyr Tyr Tyr Pro Trp Gly Gln Ala Asn His Val Thr Val Ser Ser Gln
        115                 120                 125

Arg Lys Thr Arg Lys Ala Gln Gly Arg Ala Arg Leu Ala Asp Ala Gly
    130                 135                 140

Ala Pro Val Pro His Ala Asp Gln Met Glu Gln Arg Ala Ser
145                 150                 155

<210> SEQ ID NO 48
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Ile Ser Asn Tyr Gly Met Thr Trp Val Arg Gln Ala Pro
        35                  40                  45

Gly Lys Gly Leu Glu Trp Ile Ser Thr Val Tyr Ser Asn Gly His Thr
    50                  55                  60

Tyr Tyr Ala Asp Ser Val Lys Gly Arg Phe Thr Ile Ser Arg Asp Asn
65                  70                  75                  80

Ala Lys Asn Thr Leu Tyr Leu Gln Met Asn Ser Leu Lys Pro Glu Asp
                85                  90                  95

Thr Ala Lys Tyr Tyr Cys Lys Leu Thr Gly Glu Thr His Arg Gly Gln
            100                 105                 110

Gly Thr Gln Val Thr Val Ser Ser Glu Pro Lys Thr Pro Lys Pro Gln
        115                 120                 125
```

Gly Pro Arg Gly Leu Ala Ala Gly Ala Pro Val Pro Tyr Pro Asp
        130                 135                 140

Pro Leu Glu Pro Arg Ala Ala
145                 150

<210> SEQ ID NO 49
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Gln Ala Gln Leu Ala Val Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Ile Ser Asn Tyr Gly Met Ser Trp Val Arg Gln Ala Pro
        35                  40                  45

Gly Lys Gly Leu Glu Trp Ile Ser Thr Ile Tyr Ser Asn Gly His Thr
    50                  55                  60

Tyr Ser Ala Asp Ser Val Lys Gly Arg Phe Thr Ile Ser Arg Asp Asn
65                  70                  75                  80

Ala Lys Asn Thr Leu Tyr Leu Gln Met Asn Ser Leu Lys Pro Glu Asp
                85                  90                  95

Thr Ala Lys Tyr Tyr Cys Lys Leu Val Gly Glu Thr His Arg Gly Gln
            100                 105                 110

Gly Thr Gln Val Thr Val Ser Ser Glu Pro Lys Thr Pro Lys Pro Gln
        115                 120                 125

Gly Pro Arg Gly Leu Ala Ala Gly Ala Pro Val Pro Tyr Pro Asp
    130                 135                 140

Pro Leu Glu Pro Arg Ala Ala
145                 150

<210> SEQ ID NO 50
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Gln Ala Gln Leu Ala Gly Gln Leu Gln Leu Val Glu Ser Gly Gly
1               5                   10                  15

Gly Leu Val Gln Pro Gly Gly Ser Leu Met Leu Ser Cys Val Val Ser
            20                  25                  30

Gly Val Thr Ile Ser Asn Tyr Gly Met Thr Trp Val Arg Gln Ala Pro
        35                  40                  45

Gly Lys Gly Leu Glu Trp Ile Ser Thr Ile Tyr Ser Asn Gly His Thr
    50                  55                  60

Tyr Tyr Ala Asp Ser Val Lys Gly Arg Phe Thr Ala Ser Arg Asp Asn
65                  70                  75                  80

Ala Lys Asn Thr Leu Tyr Leu Gln Met Asn Ser Leu Lys Pro Glu Asp
                85                  90                  95

Thr Ala Lys Tyr Tyr Cys Lys Leu Thr Gly Glu Thr His Arg Gly Gln
            100                 105                 110

```
Gly Thr Gln Val Thr Val Ser Ser Glu Pro Lys Thr Pro Lys Pro Gln
        115                 120                 125

Gly Pro Arg Gly Leu Ala Ala Ala Gly Ala Pro Val Pro Tyr Pro Asp
130                 135                 140

Pro Leu Glu Pro Arg Ala Ala
145                 150

<210> SEQ ID NO 51
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Thr Ala Ser
            20                  25                  30

Glu Phe Thr Leu Asp Tyr His Ser Ile Gly Trp Phe Arg Gln Ala Pro
        35                  40                  45

Gly Lys Glu Arg Glu Gly Val Ser Cys Ile Ser Tyr Gly Asp Gly Thr
    50                  55                  60

Thr Phe Tyr Thr Asp Ser Val Lys Gly Arg Phe Thr Ile Ser Arg Asp
65                  70                  75                  80

Asn Ala Lys Asn Thr Val Thr Leu Gln Met Asn Ser Leu Lys Pro Glu
                85                  90                  95

Asp Thr Ala Val Tyr Tyr Cys Ala Ala Ser Pro Gly Arg Leu Leu Leu
            100                 105                 110

Phe Arg Leu Cys Met Ser Glu Asp Glu Tyr Asp Phe Trp Gly Gln Gly
        115                 120                 125

Thr Gln Val Thr Val Ser Ser Glu Pro Lys Thr Pro Lys Pro Gln Gly
    130                 135                 140

Pro Arg Gly Leu Ala Ala Ala Gly Ala Pro Val Pro Tyr Pro Asp Pro
145                 150                 155                 160

Leu Glu Pro Arg Ala Ala
                165

<210> SEQ ID NO 52
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Gln Ala Gln Leu Ala Val Gln Leu Gln Leu Val Glu Ser Gly Gly
1               5                   10                  15

Gly Leu Val Gln Pro Gly Gly Ser Leu Met Leu Ser Cys Val Val Ser
            20                  25                  30

Gly Val Thr Ile Ser Asn Tyr Gly Met Thr Trp Val Arg Gln Ala Pro
        35                  40                  45

Gly Lys Gly Leu Glu Trp Ile Ser Thr Ile Tyr Ser Asn Gly His Thr
    50                  55                  60

Tyr Tyr Ala Asp Ser Val Lys Gly Arg Phe Thr Ala Ser Arg Asp Asn
65                  70                  75                  80
```

```
Ala Lys Asn Thr Leu Tyr Leu Gln Met Asn Ser Leu Lys Pro Glu Asp
                85                  90                  95

Thr Ala Lys Tyr Tyr Cys Lys Leu Thr Gly Glu Thr His Arg Gly Gln
            100                 105                 110

Gly Thr Gln Val Thr Val Ser Ser Glu Pro Lys Thr Pro Lys Pro Gln
        115                 120                 125

Gly Pro Arg Gly Leu Ala Ala Ala Gly Ala Pro Val Pro Tyr Pro Asp
    130                 135                 140

Pro Leu Glu Pro Arg Ala Ala
145                 150

<210> SEQ ID NO 53
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Ala Ala Ser
            20                  25                  30

Gly Arg Ala Phe Ser Val Tyr Ala Val Gly Trp Tyr Arg Gln Pro Pro
        35                  40                  45

Gly Lys Gln Arg Glu Leu Val Ala Ser Ile Thr Asp Gly Gly Ser Thr
    50                  55                  60

Asn Tyr Ala Asp Ser Val Lys Gly Arg Phe Thr Val Ser Arg Asp Asn
65                  70                  75                  80

Ala Arg Asn Thr Ala Tyr Leu Asp Met Asn Ser Leu Lys Val Glu Asp
                85                  90                  95

Thr Ala Val Tyr Tyr Cys Asn Ala Asn Tyr Gly Gly Ser Val Leu Tyr
            100                 105                 110

Asn Tyr Trp Gly Pro Gly Thr Gln Val Thr Val Ser Thr Glu Pro Lys
        115                 120                 125

Thr Pro Lys Pro Gln Gly Pro Arg Gly Leu Ala Ala Ala Gly Ala Pro
    130                 135                 140

Val Pro Tyr Pro Asp Pro Leu Glu Pro Arg Ala Ala
145                 150                 155

<210> SEQ ID NO 54
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Val Val Ser
            20                  25                  30

Gly Val Thr Ile Ser Asn Tyr Gly Met Thr Trp Val Arg Gln Ala Pro
        35                  40                  45

Gly Lys Gly Leu Glu Trp Ile Ser Thr Val Tyr Ser Asn Gly His Thr
    50                  55                  60
```

Tyr Tyr Ala Asp Ser Val Lys Gly Arg Phe Thr Ile Ser Arg Asp Asn
65                  70                  75                  80

Ala Lys Asn Thr Leu Tyr Leu Gln Met Asn Ser Leu Lys Pro Glu Asp
            85                  90                  95

Thr Ala Lys Tyr Tyr Cys Lys Leu Thr Gly Glu Thr His Arg Gly Gln
        100                 105                 110

Gly Thr Gln Val Thr Val Ser Ser Glu Pro Lys Thr Pro Lys Pro Gln
    115                 120                 125

Gly Pro Arg Gly Leu Ala Ala Gly Ala Pro Val Pro Tyr Pro Asp
130                 135                 140

Pro Leu Glu Pro Arg Ala Ala
145                 150

<210> SEQ ID NO 55
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gln Ala Gln Leu Ala Val Gln Leu Gln Leu Val Glu Ser Gly Gly
1               5                   10                  15

Gly Leu Val Gln Pro Gly Gly Ser Leu Arg Leu Ser Cys Glu Val Ser
            20                  25                  30

Gly Ser Arg Gly Ser Ile Tyr Phe Ser Gly Trp Tyr Arg Gln Ala Pro
        35                  40                  45

Gly Lys Gln Arg Glu Leu Val Ala Ser Ile Thr Ser Gly Gly Thr Thr
    50                  55                  60

Asn Tyr Ala Asp Ser Val Lys Gly Arg Phe Thr Ile Ser Arg Asp Asn
65                  70                  75                  80

Ala Lys Asn Thr Val Tyr Leu Gln Met Asn Ser Leu Lys Pro Glu Asp
            85                  90                  95

Thr Ala Val Tyr Tyr Cys Asn Ile Gly Arg Tyr Gly Leu Gly Gly Ser
        100                 105                 110

Trp Gly Gln Gly Thr Gln Val Thr Val Ser Ser Glu Pro Lys Thr Pro
    115                 120                 125

Lys Pro Gln Gly Pro Arg Gly Leu Ala Ala Gly Ala Pro Val Pro
130                 135                 140

Tyr Pro Asp Pro Leu Glu Pro Arg Ala Ala
145                 150

<210> SEQ ID NO 56
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Glu Ala Ser
            20                  25                  30

Gly Phe Thr Phe Asp Asp Tyr Ala Ile Gly Trp Phe Arg Gln Ala Pro
        35                  40                  45

Gly Lys Glu Arg Glu Val Ser Cys Ile Ser His Asn Gly Gly Thr
    50                  55                  60

Thr Asn Tyr Ala Asp Ser Val Lys Gly Arg Phe Ser Ile Ser Arg Asp
65                  70                  75                  80

Asn Ala Lys Asn Thr Val Tyr Leu Gln Met Asn Gly Leu Lys Pro Glu
                85                  90                  95

Asp Thr Ala Asn Tyr Tyr Cys Ala Gly Ala Arg Ser Gly Leu Cys Val
                100                 105                 110

Phe Phe Glu Leu Gln Asp Tyr Asp Tyr Trp Gly Gln Gly Thr Gln Val
            115                 120                 125

Thr Val Ser Ser Ala His His Ser Glu Asp Pro Gly Pro Arg Gly Leu
        130                 135                 140

Ala Ala Ala Gly Ala Pro Val Pro Tyr Pro Asp Pro Leu Glu Pro Arg
145                 150                 155                 160

Ala Ala

<210> SEQ ID NO 57
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gln Ala Gln Pro Ala Val Leu Ala Ala Leu Leu Gln Gly Val Gln
1               5                   10                  15

Ala Gln Val Lys Leu Val Glu Ser Gly Gly Gly Ser Val Gln Ala Gly
            20                  25                  30

Gly Ser Leu Arg Leu Ser Cys Thr Ala Ser Gly Ser Asp Tyr Arg Trp
        35                  40                  45

Met Tyr Ile Ala Arg Phe Arg Gln Cys Pro Gly Lys Glu Arg Glu Gly
    50                  55                  60

Val Ala Ala Ile Tyr Thr Asp Thr Asp Ser Ser Pro Ile Tyr
65                  70                  75                  80

Ala Thr Ser Ala Lys Gly Arg Phe Thr Ile Ser Gln Asp Lys Asp Lys
                85                  90                  95

Asn Ala Val Tyr Leu Gln Met Asn Ser Pro Lys Pro Glu Asp Thr Ala
                100                 105                 110

Met Tyr Tyr Cys Ala Ala Arg Ala Phe Gly Gly Thr Trp Ser Leu Ser
            115                 120                 125

Ser Pro Asp Asp Phe Ser Ala Trp Gly Gln Gly Thr Gln Val Thr Val
        130                 135                 140

Ser Ser Gly Thr Asn Glu Val Cys Lys Trp Pro Pro Arg Pro Cys Gly
145                 150                 155                 160

Arg Arg Cys Ala Gly Ala Val Ser Gly Ser Ala Gly Thr Ala Cys Arg
                165                 170                 175

Ile Asp

<210> SEQ ID NO 58
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 58

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Thr Ala Ser
            20                  25                  30

Lys Phe His Leu Asp Ser Tyr Ala Val Ala Trp Phe Arg Gln Thr Pro
        35                  40                  45

Gly Lys Glu Arg Glu Ala Val Ser Phe Ile Asn Thr Ser Asp Asp Val
    50                  55                  60

Thr Tyr Phe Ala Asp Ser Val Lys Gly Arg Phe Thr Ile Ser Arg Asp
65                  70                  75                  80

Asn Ser Lys Asn Thr Val Tyr Leu Gln Met Asn Val Leu Lys Pro Glu
                85                  90                  95

Asp Thr Ser Val Tyr Val Cys Ala Ala Val Arg Ser Pro Gly Pro Thr
            100                 105                 110

Gly Pro Ser Met Gln Pro Met Trp Ser Val Pro Asp Leu Tyr Asp Tyr
        115                 120                 125

Trp Gly Gln Gly Thr Gln Val Thr Val Ser Ser Ala His His Ser Glu
130                 135                 140

Asp Pro Gly Pro Arg Gly Leu Ala Ala Ala Gly Ala Pro Val Pro Tyr
145                 150                 155                 160

Pro Asp Pro Leu Glu Pro Arg Ala Ala
                165

<210> SEQ ID NO 59
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Gln Ala Gln Leu Ala Val Gln Leu Gln Leu Val Glu Ser Gly Gly
1               5                   10                  15

Gly Thr Val Gln Pro Gly Gly Ser Leu Asn Leu Ser Cys Val Thr Ser
            20                  25                  30

Gly Phe Thr Phe Ser Arg His Asp Met Ser Trp Val Arg Gln Ala Pro
        35                  40                  45

Gly Lys Gly Pro Glu Trp Ile Ser Gly Ile Gly Thr Ser Gly Thr Ser
    50                  55                  60

Gly Arg Tyr Ala Ser Val Lys Gly Arg Phe Thr Ile Ser Arg Asp
65                  70                  75                  80

Asn Ala Lys Asp Thr Leu Tyr Leu Gln Met Asp Ser Leu Lys Pro Glu
                85                  90                  95

Asp Thr Gly Leu Tyr Tyr Cys Thr Thr Gly Val Tyr Ser Ala Tyr
            100                 105                 110

Val Gln Pro Arg Gly Lys Gly Thr Gln Val Thr Val Ser Ser Ala His
        115                 120                 125

His Ser Glu Asp Pro Gly Pro Arg Gly Leu Ala Ala Ala Gly Ala Pro
    130                 135                 140

Val Pro Tyr Pro Asp Pro Leu Glu Pro Arg Ala Ala
145                 150                 155

<210> SEQ ID NO 60
<211> LENGTH: 109

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Gln Ala Gln Leu Ala Val Gln Leu Gln Leu Val Glu Ser Gly Gly
1               5                   10                  15

Gly Leu Val Gln Pro Gly Gly Ser Leu Arg Leu Ser Cys Ala Ala Ser
            20                  25                  30

Gly Arg Ala Phe Ser Val Tyr Ala Val Gly Trp Tyr Arg Gln Ile Pro
        35                  40                  45

Gly Asn Gln Arg Glu Met Val Ala Ala Ile Ser Ser Gly Gly Asn Thr
    50                  55                  60

Lys Tyr Ser Asp Ser Val Lys Gly Arg Phe Thr Val Ser Ser Glu Pro
65                  70                  75                  80

Lys Thr Pro Lys Pro Gln Gly Pro Arg Gly Leu Ala Ala Ala Gly Ala
                85                  90                  95

Pro Val Pro Tyr Pro Asp Pro Leu Glu Pro Arg Ala Ala
            100                 105

<210> SEQ ID NO 61
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gln Ala Gln Pro Ala Val Leu Ala Ala Leu Leu Gln Gly Val Gln
1               5                   10                  15

Ala Gln Val Lys Leu Val Glu Ser Gly Gly Gly Ser Val Gln Ala Gly
            20                  25                  30

Gly Ser Leu Arg Leu Ser Cys Thr Ala Ser Gly Ser Asp Tyr Arg Trp
        35                  40                  45

Met Tyr Ile Ala Arg Phe Arg Gln Cys Pro Gly Lys Glu Arg Glu Gly
    50                  55                  60

Val Ala Ala Ile Tyr Thr Asp Asp Thr Asp Ser Ser Pro Ile Tyr
65                  70                  75                  80

Ala Thr Ser Ala Lys Gly Arg Phe Thr Ile Ser Gln Asp Lys Asp Lys
                85                  90                  95

Asn Ala Val Tyr Leu Gln Met Asn Ser Pro Lys Pro Glu Asp Thr Ala
            100                 105                 110

Met Tyr Tyr Cys Ala Ala Arg Ala Phe Gly Gly Thr Trp Ser Leu Ser
        115                 120                 125

Ser Pro Asp Asp Phe Ser Ala Trp Gly Gln Gly Thr Gln Val Thr Val
    130                 135                 140

Ser Ser Gly Thr Asn Glu Val Cys Lys Trp Pro Pro Arg Pro Cys Gly
145                 150                 155                 160

Arg Arg Cys Ala Gly Ala Val Ser Gly Ser Ala Gly Thr Ala Cys Arg
                165                 170                 175

Ile Asp Cys

<210> SEQ ID NO 62
<211> LENGTH: 164
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 62

Met Gln Ala Gln Leu Ala Gly Gln Leu Gln Leu Val Glu Ser Gly Gly
1               5                   10                  15

Gly Met Val Gln Pro Gly Gly Ser Leu Arg Leu Ser Cys Ala Ala Ser
            20                  25                  30

Gly Phe Ile Phe Ser Arg Tyr Asp Met Gly Trp Val Arg Gln Thr Pro
        35                  40                  45

Gly Lys Gly Arg Glu Trp Val Ser Gly Ile Asn Ser Gly Gly Gly Arg
    50                  55                  60

Thr Tyr Tyr Ala Asp Ser Val Lys Gly Arg Phe Thr Ile Ser Arg Asp
65                  70                  75                  80

Asp Asp Lys Ala Thr Leu Tyr Leu Ser Met Asp Gly Leu Lys Pro Glu
                85                  90                  95

Asp Thr Ala Leu Tyr His Cys Val Arg Phe Thr Val Lys Thr Pro Gln
            100                 105                 110

Gly Tyr Tyr Tyr Leu Asn Asp Phe Asp Tyr Trp Gly Gln Gly Thr Gln
        115                 120                 125

Val Thr Val Ser Ser Glu Pro Lys Thr Pro Lys Pro Gln Gly Pro Arg
    130                 135                 140

Gly Leu Ala Ala Ala Gly Ala Pro Val Pro Tyr Pro Asp Pro Leu Glu
145                 150                 155                 160

Pro Arg Ala Ala

<210> SEQ ID NO 63
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Gln Ala Gln Leu Ala Gly Gln Leu Gln Leu Val Glu Ser Gly Gly
1               5                   10                  15

Gly Leu Val Gln Ile Gly Gly Ser Leu Arg Leu Ser Cys Ala Ala Ser
            20                  25                  30

Gly Ser Asp Phe Ser Ile Tyr His Met Gly Trp Tyr Arg Gln Ala Pro
        35                  40                  45

Gly Lys Gln Arg Glu Leu Val Ala Ala Ile Thr Ser Gly Gly Ser Thr
    50                  55                  60

Asn Tyr Ala Asp Ser Val Lys Gly Arg Phe Thr Ile Ser Ser Asp Asn
65                  70                  75                  80

Ala Lys Asn Thr Val Tyr Leu Gln Met Asn Ser Leu Lys Pro Glu Asp
                85                  90                  95

Thr Ala Val Tyr Tyr Cys Asn Ala Asp Gly Val Pro Glu Tyr Ser Asp
            100                 105                 110

Tyr Ala Ser Gly Pro Val Tyr Trp Gly Gln Gly Thr Gln Val Thr Val
        115                 120                 125

Ser Ser Ala His His Ser Glu Asp Pro Gly Pro Arg Gly Leu Ala Ala
    130                 135                 140

Ala Gly Ala Pro Val Pro Tyr Pro Asp Pro Leu Glu Pro Arg Ala Ala
145                 150                 155                 160

<210> SEQ ID NO 64
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Gln Ala Gln Leu Ala Val Gln Leu Gln Leu Val Glu Ser Gly Gly
1               5                   10                  15

Gly Leu Val Gln Ala Gly Gly Ser Leu Arg Leu Ser Cys Val Ala Ser
            20                  25                  30

Gly Ser Met Phe Asn Phe Tyr Gly Met Ala Trp Tyr Arg Gln Ala Pro
        35                  40                  45

Gly Lys Gln Arg Glu Leu Val Ala Ser Ile Asp Ser Glu Gly Arg Thr
    50                  55                  60

Thr Asn Tyr Pro Asp Ser Leu Lys Gly Arg Phe Thr Ile Ser Arg Asp
65                  70                  75                  80

Asp Ala Lys Ser Thr Ala Tyr Leu Gln Met Asn Asn Leu Ile Pro Asp
                85                  90                  95

Asp Thr Ala Val Tyr Tyr Cys Asn Ala Phe Arg Gly Arg Met Tyr Asp
            100                 105                 110

Tyr Trp Gly Gln Gly Thr Gln Val Thr Val Ser Ser Glu Pro Lys Thr
        115                 120                 125

Pro Lys Pro Gln Gly Pro Arg Gly Leu Ala Ala Ala Gly Ala Pro Val
    130                 135                 140

Pro Tyr Pro Asp Pro Leu Glu Pro Arg Ala Ala
145                 150                 155

<210> SEQ ID NO 65
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Gln Ala Gln Leu Ala Gly Gln Leu Gln Leu Val Glu Ser Gly Gly
1               5                   10                  15

Arg Leu Val Ala Pro Gly Arg Ser Leu Lys Leu Ser Arg Thr Phe Ser
            20                  25                  30

Gly Leu Tyr Leu His Ser Ser Ala Phe Gly Trp Phe Pro His Val Pro
        35                  40                  45

Arg Glu Ala Arg Glu Gly Val Ala Phe Leu Cys Asn Ser Gly Ser Asp
    50                  55                  60

Pro Ile Tyr Leu His Pro Glu Lys Gly Ile Phe Thr Leu Ser Arg His
65                  70                  75                  80

Cys Val Lys Thr Val Ser Pro Phe Glu Asp Asn Asp Thr Val Glu His
                85                  90                  95

Thr Pro Thr Tyr Gln Cys Pro Thr His Leu Val Ile Thr His Pro Cys
            100                 105                 110

Ile Cys Ile Pro Ser Ala Met Asp Tyr Arg Gly Lys Gly Thr Leu Val
        115                 120                 125

Pro Leu Ser Ser Lys Pro Thr Thr Pro Lys Pro Arg Ala Pro Lys Ala
    130                 135                 140

```
Leu Arg Pro Gln Val Pro Arg Cys Arg Ile Arg Phe Arg
145                 150                 155
```

<210> SEQ ID NO 66
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Met Gln Ala Gln Leu Ala Gly Gln Leu Gln Leu Val Glu Ser Gly Gly
1               5                   10                  15

Gly Arg Val Gln Ala Gly Gly Ser Leu Thr Leu Ser Cys Ala Ala Ser
                20                  25                  30

Gly Asp Ile Phe Thr Leu Ala Ser Met Gly Trp Tyr Arg Glu Asp Leu
            35                  40                  45

His Lys Lys Arg Glu Leu Val Ala Gln Leu Met Ser Asp Gly Thr Ala
    50                  55                  60

Asn Tyr Gly Asp Ser Val Lys Gly Arg Val Thr Ile Ser Arg Asp Asp
65                  70                  75                  80

Val Asp Thr Thr Val His Leu Arg Met Asn Thr Leu Gln Pro Ser Asp
                85                  90                  95

Thr Gly Glu Tyr Phe Cys Tyr Ile His Thr Ser Arg Glu Ile Thr Trp
            100                 105                 110

Gly Arg Gly Thr Gln Val Thr Val Ser Gln Gly Glu Ser Ser Ala Pro
        115                 120                 125

Gln Ser Ser Ala Pro Gln Ala Thr Val Ser Ser Ala His His Ser Glu
    130                 135                 140

Asp Pro Gly Pro Arg Gly Leu Ala Ala Ala Gly Ala Pro Val Pro Tyr
145                 150                 155                 160

Pro Asp Pro Leu Glu Pro Arg Ala Ala
                165
```

<210> SEQ ID NO 67
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Met Gln Ala Gln Leu Ala Gly Gln Leu Gln Leu Val Glu Ser Gly Gly
1               5                   10                  15

Gly Leu Val Glu Val Gly Glu Ser Leu Arg Leu Ser Cys Val Ala Leu
                20                  25                  30

Gly Phe Thr Leu Asp Gly Tyr Ala Ile Gly Trp Phe Arg Gln Ala Pro
            35                  40                  45

Gly Lys Glu Arg Glu Lys Ile Ser Cys Ile Ser Ser Thr Gly Asp Ser
    50                  55                  60

Thr Asn Tyr Asp Asp Ser Val Lys Gly Arg Phe Thr Ile Ser Arg Asp
65                  70                  75                  80

Thr Ala Lys Ser Thr Val Phe Leu Gln Met Asn Asn Leu Ile Pro Glu
                85                  90                  95

Asp Thr Ala Ile Tyr Tyr Cys Gly Ala Asp Leu Leu Ala Arg Cys Gly
            100                 105                 110
```

-continued

Arg Val Trp Tyr Phe Pro Pro Asp Leu Asn Tyr Arg Gly Gln Gly Thr
            115                 120                 125

Gln Val Thr Val Ser Ser Ala His His Ser Glu Asp Pro Gly Pro Arg
    130                 135                 140

Gly Leu Ala Ala Ala Gly Ala Pro Val Pro Tyr Pro Asp Pro Leu Glu
145                 150                 155                 160

Pro Arg Ala Ala

```
<210> SEQ ID NO 68
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (22)..(45)
<223> OTHER INFORMATION: Any amino acid
<220> FEATURE:
<221> NAME/KEY: MOD_RES
<222> LOCATION: (47)..(67)
<223> OTHER INFORMATION: Any amino acid and this region may encompass 1
      to 21 residues, wherein some positions may be absent
<220> FEATURE:
<221> NAME/KEY: MOD_RES
<222> LOCATION: (70)..(73)
<223> OTHER INFORMATION: Any amino acid
<220> FEATURE:
<221> NAME/KEY: MOD_RES
<222> LOCATION: (75)..(93)
<223> OTHER INFORMATION: Any amino acid and this region may encompass 1
      to 19 residues, wherein some positions may be absent
<220> FEATURE:
<221> NAME/KEY: MOD_RES
<222> LOCATION: (95)..(96)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (100)..(149)
<223> OTHER INFORMATION: Any amino acid and this region may encompass 1
      to 50 residues, wherein some positions may be absent
<220> FEATURE:
<221> NAME/KEY: MOD_RES
<222> LOCATION: (151)..(172)
<223> OTHER INFORMATION: Any amino acid and this region may encompass 1
      to 22 residues, wherein some positions may be absent
<220> FEATURE:
<221> NAME/KEY: MOD_RES
<222> LOCATION: (174)..(181)
```

```
<223> OTHER INFORMATION: Any amino acid and this region may encompass 1
     to 8 residues, wherein some positions may be absent
<220> FEATURE:
<223> OTHER INFORMATION: see specification as filed for detailed
     description of substitutions and preferred embodiments

<400> SEQUENCE: 68

Gln Xaa Xaa Leu Val Glu Ser Gly Gly Xaa Xaa Val Xaa Xaa Gly Xaa
 1               5                  10                  15

Ser Leu Xaa Leu Ser Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Glu Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Lys Gly Xaa Xaa Xaa Xaa Ser Xaa Xaa Xaa Xaa Xaa Xaa
65                  70                  75                  80

Xaa Xaa Xaa Xaa Xaa Xaa Xaa Xaa Xaa Xaa Xaa Xaa Xaa Thr Xaa Xaa
                85                  90                  95

Tyr Xaa Cys Xaa Xaa Xaa Xaa Xaa Xaa Xaa Xaa Xaa Xaa Xaa Xaa Xaa
               100                 105                 110

Xaa Xaa Xaa Xaa Xaa Xaa Xaa Xaa Xaa Xaa Xaa Xaa Xaa Xaa Xaa Xaa
           115                 120                 125

Xaa Xaa Xaa Xaa Xaa Xaa Xaa Xaa Xaa Xaa Xaa Xaa Xaa Xaa Xaa Xaa
       130                 135                 140

Xaa Xaa Xaa Xaa Xaa Ser Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Val Xaa Xaa Xaa
               165                 170                 175

Xaa Xaa Xaa Xaa Xaa Arg
           180

<210> SEQ ID NO 69
<211> LENGTH: 183
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (53)..(53)
<223> OTHER INFORMATION: Any amino acid
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (62)..(62)
```

```
<223> OTHER INFORMATION: Any amino acid
<220> FEATURE:
<221> NAME/KEY: MOD_RES
<222> LOCATION: (64)..(67)
<223> OTHER INFORMATION: Any amino acid
<220> FEATURE:
<221> NAME/KEY: MOD_RES
<222> LOCATION: (102)..(102)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (108)..(108)
<223> OTHER INFORMATION: Any amino acid
<220> FEATURE:
<221> NAME/KEY: MOD_RES
<222> LOCATION: (110)..(129)
<223> OTHER INFORMATION: Any amino acid
<220> FEATURE:
<221> NAME/KEY: MOD_RES
<222> LOCATION: (135)..(143)
<223> OTHER INFORMATION: Any amino acid
<220> FEATURE:
<221> NAME/KEY: MOD_RES
<222> LOCATION: (151)..(152)
<223> OTHER INFORMATION: Any amino acid

<400> SEQUENCE: 69

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Val Xaa Ser
            20                  25                  30

Gly Thr Ile Ser Xaa Tyr Gly Met Gly Trp Xaa Arg Gln Ala Pro Gly
        35                  40                  45

Lys Gly Arg Glu Xaa Val Ser Thr Ile Xaa Ser Xaa Gly Xaa Thr Xaa
    50                  55                  60

Xaa Xaa Xaa Tyr Tyr Ala Asp Ser Val Lys Gly Arg Phe Thr Ile Ser
65                  70                  75                  80

Arg Asp Asn Ala Lys Asn Thr Leu Tyr Leu Gln Met Asn Ser Leu Lys
                85                  90                  95

Pro Glu Asp Thr Ala Xaa Tyr Tyr Cys Xaa Leu Xaa Gly Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa His Arg Gly Gln Gly Xaa Xaa Xaa Xaa Xaa Xaa Xaa Xaa Xaa Thr
    130                 135                 140

Gln Val Thr Val Ser Ser Xaa Xaa Glu Pro Lys Thr Pro Lys Pro Gln
145                 150                 155                 160

Gly Pro Arg Gly Leu Ala Ala Gly Ala Pro Val Pro Tyr Pro Asp
                165                 170                 175

Pro Leu Glu Pro Arg Ala Ala
            180

<210> SEQ ID NO 70
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
```

```
<223> OTHER INFORMATION: This region may encompass 'Leu Gln' or
      'Val Lys'
<220> FEATURE:
<221> NAME/KEY: MOD_RES
<222> LOCATION: (10)..(11)
<223> OTHER INFORMATION: This region may encompass 'Gly Ser,' 'Gly Leu,'
      'Gly Arg,' 'Gly Met,' 'Arg Leu' or 'Gly Thr'
<220> FEATURE:
<221> NAME/KEY: MOD_RES
<222> LOCATION: (13)..(14)
<223> OTHER INFORMATION: This region may encompass 'Gln Ala,' 'Gln Pro,'
      'Gln Ile,' 'Ala Pro' or 'Glu Val'
<220> FEATURE:
<221> NAME/KEY: MOD_RES
<222> LOCATION: (16)..(16)
<223> OTHER INFORMATION: Arg, Gly or Glu
<220> FEATURE:
<221> NAME/KEY: MOD_RES
<222> LOCATION: (19)..(19)
<223> OTHER INFORMATION: Lys, Asn, Arg, Met or Thr
<220> FEATURE:
<221> NAME/KEY: MOD_RES
<222> LOCATION: (22)..(45)
<223> OTHER INFORMATION: This region may encompass the sequences
      'CTASGSDYRWMYIARFRQCPGKER,' 'CAASGRAFSVYAVGWYRQIPGNQR,'
      'CTASETTFEIYPMAWYRQAPGKQR,' 'CAASGSDFSIYHMGWYRQAPGKQR,'
      'CAASGDIFTLASMGWYREDLHKKR,' 'CEASGFTFDDYAIGWFRQAPGKER,'
<220> FEATURE:
<221> NAME/KEY: MOD_RES
<222> LOCATION: (22)..(45)
<223> OTHER INFORMATION: continued from above;
      'CVALGFTLDGYAIGWFRQAPGKER,' 'CTASKPHLDSYAVAWFRQTPGKER,'
      'CVVSGVTISNYGMTWVRQAPGKGL,' 'CVVSGVTFNNYGMTWVRQAPGKGL,'
      'CVTSGFTFSRHDMSWVRQAPGKGP,' 'CAASGFIFSRYDMGWVRQTPGKGR,'
      'CAASGIILNFYGMGWDRQTPGQGL,'
<220> FEATURE:
<221> NAME/KEY: MOD_RES
<222> LOCATION: (22)..(45)
<223> OTHER INFORMATION: continued from above;
      'CTASEFTLDYHSIGWFRQAPGKER,' 'CAASGRAFSVYAVGWYRQPPGKQR,'
      'CEVSGSRGSIYFSGWYRQAPGKQR,' 'CVASGSMFNFYGMAWYRQAPGKQR' or
      'RTFSGLYLHSSAFGWFPHVPREAR'
<220> FEATURE:
<221> NAME/KEY: MOD_RES
<222> LOCATION: (47)..(67)
<223> OTHER INFORMATION: This region may be 17 to 21 residues and
      encompasses the sequences: 'GVAAIYTDDTDDSSPIYATSA,'
      'MVAAISSGGNTKYSDSV,' 'LVAGINMISSTKYIDSV,' 'LVAAITSGGSTNYADSV,'
      'LVAQLMSDGTANYGDSV,' 'EVSCISHNGGTTNYADSV,' 'KISCISSTGDSTNYDDSV,'
<220> FEATURE:
<221> NAME/KEY: MOD_RES
<222> LOCATION: (47)..(67)
<223> OTHER INFORMATION: continued from above; 'AVSFINTSDDVTYFADSV,'
      'WISTIYSNGHTYSADSV,' 'WISSIYSNGHTYSADSV,' 'WISGIGTSGTSGRYASSV,'
      'WVSGINSGGGRTYYADSV,' 'GVSYVNNNGMTNYADSV,' 'GVSCISYGDGTTFYTDSV,'
      'LVASITDGGSTNYADSV,' 'LVASITSGGTTNYADSV,'
<220> FEATURE:
<221> NAME/KEY: MOD_RES
<222> LOCATION: (47)..(67)
<223> OTHER INFORMATION: continued from above; 'LVASIDSEGRTTNYPDSL' or
      'GVAFLCNSGSDPIYLHPE,' wherein some positions may be absent
<220> FEATURE:
<221> NAME/KEY: MOD_RES
<222> LOCATION: (70)..(73)
<223> OTHER INFORMATION: This region may encompass the sequences 'RFTI,'
      'RVTI,' 'RFSI,' 'RFTA,' 'RFTV' or 'IFTL'
<220> FEATURE:
<221> NAME/KEY: MOD_RES
<222> LOCATION: (75)..(93)
<223> OTHER INFORMATION: This region may be 18 to 19 residues and
      encompasses the sequences: 'QDKDKNAVYLQMNSPKPED,'
      'RDNDKNTMYLQMNSLKPED,' 'SDNAKNTVYLQMNSLKPED,'
      'RDDVDTTVHLRMNTLQPSD,' 'RDNAKNTVYLQMNGLKPED,'
      'RDTAKSTVFLQMNNLIPED,'
<220> FEATURE:
<221> NAME/KEY: MOD_RES
<222> LOCATION: (75)..(93)
<223> OTHER INFORMATION: continued from above; 'RDNSKNTVYLQMNVLKPED,'
      'RDNANNTLYLQMNSLKPED,' 'RDNAKNTLYLQMISLKPED,'
```

```
        'RDNAKDTLYLQMDSLKPED,' 'RDDDKATLYLSMDGLKPED,'
        'RDNAKNTMYLQMNSLKPED,' 'RDNAKNTVTLQMNSLKPED,'
        'RDNARNTAYLDMNSLKVED,'
<220> FEATURE:
<221> NAME/KEY: MOD_RES
<222> LOCATION: (75)..(93)
<223> OTHER INFORMATION: continued from above; 'RDNAKNTVYLQMNSLKPED,'
        'RDDAKSTAYLQMNNLIPDD,' 'RHCVKTVSPFEDNDTVEH,'
        RDNAKNTLYLQMNSLKPED,' wherein some positions may be absent or
        this region is absent in its entirety
<220> FEATURE:
<221> NAME/KEY: MOD_RES
<222> LOCATION: (95)..(96)
<223> OTHER INFORMATION: This region encompasses 'Pro Thr,' 'Ala Val,'
        'Ala Asp,' 'Ala Leu,' 'Gly Leu,' 'Ala Lys,' 'Ala Asn,' 'Ala Ile,'
        'Ser Val,' 'Gly Glu,' 'Ala Met' or this region is absent in its
        entirety
<220> FEATURE:
<221> NAME/KEY: MOD_RES
<222> LOCATION: (98)..(98)
<223> OTHER INFORMATION: Any amino acid or absent
<220> FEATURE:
<221> NAME/KEY: MOD_RES
<222> LOCATION: (100)..(135)
<223> OTHER INFORMATION: This region may be 17 to 36 residues and
        encompasses the sequences: 'AARAFGGTWSLSSPDDFSAWGQGTQVTVS,'
        'NLDTTMVEGVEYWGQGTQVTVS,' 'NADGVPEYSDYASGPVYWGQGTQVTVS,'
        'YIHTSREITWGRGTQVTVSQGESSAPQSSAPQATVS,'
<220> FEATURE:
<221> NAME/KEY: MOD_RES
<222> LOCATION: (100)..(135)
<223> OTHER INFORMATION: continued from above;
        'AGARSGLCVFFELQDYDYWGQGTQVTVS,' 'GADLLARCGRVWYFPPDLNYRGQGTQVTVS,'
        'AAVRSPGPTGPSMQPMWSVPDLYDYWGQGTQVTVS,' 'KLTGETHRGQGTQVTVS,'
        'KLVGETHRGQGTQVTVS,' 'RLTGETYRGQGTQVTVS,'
        'TTGGVYSAYVQPRGKGTQVTVS,'
<220> FEATURE:
<221> NAME/KEY: MOD_RES
<222> LOCATION: (100)..(135)
<223> OTHER INFORMATION: continued from above;
        'VRFTVKTPQGYYYLNDFDYWGQGTQVTVS,' 'NVSAYTYRSNYYYPWGQANHVTVS,'
        'AASPGRLLLFRLCMSEDEYDFWGQGTQVTVS,' 'NANYGGSVLYNYWGPGTQVTVS,'
        'NIGRYGLGGSWGQGTQVTVS,' 'NAFRGRMYDYWGQGTQVTVS,'
<220> FEATURE:
<221> NAME/KEY: MOD_RES
<222> LOCATION: (100)..(135)
<223> OTHER INFORMATION: continued from above;
        'PTHLVITHPCICIPSAMDYRGKGTLVPLS,' wherein some positions may be
        absent or this region is absent in its entirety
<220> FEATURE:
<221> NAME/KEY: MOD_RES
<222> LOCATION: (137)..(156)
<223> OTHER INFORMATION: This region may be 17 to 20 residues and
        encompasses the sequences: 'STNEVCKWPPRPCGRRCAGA,'
        'SHHSEDPGPRGLAAAGAP,' 'SEPKTPKPQGPRGLAAAGAP,'
        'TEPKTPKPQGPRGLAAAGAP,' 'SKPTTPKPRAPKALRPQ,'
        'SAHHSEDPGPRGLAAAGAP,'
<220> FEATURE:
<221> NAME/KEY: MOD_RES
<222> LOCATION: (137)..(156)
<223> OTHER INFORMATION: continued from above; 'SQRKTRKAQGRARLADAGAP'
        wherein some positions may be absent
<220> FEATURE:
<221> NAME/KEY: MOD_RES
<222> LOCATION: (158)..(165)
<223> OTHER INFORMATION: This region may be 7 to 8 residues and
        encompasses the sequences: 'PYPDPLEP,' 'SGSAGTAC,' 'PHADQMEQ' or
        'PRCRIRF' wherein some positions may be absent
<220> FEATURE:
<223> OTHER INFORMATION: see specification as filed for detailed
        description of substitutions and preferred embodiments

<400> SEQUENCE: 70

Gln Xaa Xaa Leu Val Glu Ser Gly Gly Xaa Xaa Val Xaa Xaa Gly Xaa
1               5                   10                  15

Ser Leu Xaa Leu Ser Xaa Xaa Xaa Xaa Xaa Xaa Xaa Xaa Xaa Xaa
            20                  25                  30
```

```
Xaa Xaa Xaa Xaa Xaa Xaa Xaa Xaa Xaa Xaa Xaa Xaa Glu Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Lys Gly Xaa Xaa Xaa Xaa Ser Xaa Xaa Xaa Xaa Xaa
65                  70                  75                  80

Xaa Xaa Xaa Xaa Xaa Xaa Xaa Xaa Xaa Xaa Xaa Xaa Thr Xaa Xaa
                85                  90                  95

Tyr Xaa Cys Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Ser Xaa Xaa Xaa Xaa Xaa Xaa Xaa
    130                 135                 140

Xaa Xaa Xaa Xaa Xaa Xaa Xaa Xaa Xaa Xaa Xaa Val Xaa Xaa Xaa
145                 150                 155                 160

Xaa Xaa Xaa Xaa Xaa Arg
            165

<210> SEQ ID NO 71
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Thr Ala Ser Gly Ser Asp Tyr Arg Trp Met Tyr Ile Ala Arg Phe
1               5                   10                  15

Arg Gln Cys Pro Gly Lys Glu Arg
            20

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Ala Ala Ser Gly Arg Ala Phe Ser Val Tyr Ala Val Gly Trp Tyr
1               5                   10                  15

Arg Gln Ile Pro Gly Asn Gln Arg
            20

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr Ala Ser Glu Thr Thr Phe Glu Ile Tyr Pro Met Ala Trp Tyr
1               5                   10                  15

Arg Gln Ala Pro Gly Lys Gln Arg
            20
```

<210> SEQ ID NO 74
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Ala Ala Ser Gly Ser Asp Phe Ser Ile Tyr His Met Gly Trp Tyr
1               5                   10                  15

Arg Gln Ala Pro Gly Lys Gln Arg
            20

<210> SEQ ID NO 75
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Ala Ala Ser Gly Asp Ile Phe Thr Leu Ala Ser Met Gly Trp Tyr
1               5                   10                  15

Arg Glu Asp Leu His Lys Lys Arg
            20

<210> SEQ ID NO 76
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Glu Ala Ser Gly Phe Thr Phe Asp Asp Tyr Ala Ile Gly Trp Phe
1               5                   10                  15

Arg Gln Ala Pro Gly Lys Glu Arg
            20

<210> SEQ ID NO 77
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Val Ala Leu Gly Phe Thr Leu Asp Gly Tyr Ala Ile Gly Trp Phe
1               5                   10                  15

Arg Gln Ala Pro Gly Lys Glu Arg
            20

<210> SEQ ID NO 78
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Cys Thr Ala Ser Lys Phe His Leu Asp Ser Tyr Ala Val Ala Trp Phe
1               5                   10                  15

Arg Gln Thr Pro Gly Lys Glu Arg
            20
```

<210> SEQ ID NO 79
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Cys Val Val Ser Gly Val Thr Ile Ser Asn Tyr Gly Met Thr Trp Val
1               5                   10                  15

Arg Gln Ala Pro Gly Lys Gly Leu
            20
```

<210> SEQ ID NO 80
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Cys Val Val Ser Gly Val Thr Phe Asn Asn Tyr Gly Met Thr Trp Val
1               5                   10                  15

Arg Gln Ala Pro Gly Lys Gly Leu
            20
```

<210> SEQ ID NO 81
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Cys Val Thr Ser Gly Phe Thr Phe Ser Arg His Asp Met Ser Trp Val
1               5                   10                  15

Arg Gln Ala Pro Gly Lys Gly Pro
            20
```

<210> SEQ ID NO 82
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

```
Cys Ala Ala Ser Gly Phe Ile Phe Ser Arg Tyr Asp Met Gly Trp Val
1               5                   10                  15

Arg Gln Thr Pro Gly Lys Gly Arg
            20
```

<210> SEQ ID NO 83
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 83

Cys Ala Ala Ser Gly Ile Ile Leu Asn Phe Tyr Gly Met Gly Trp Asp
1               5                   10                  15

Arg Gln Thr Pro Gly Gln Gly Leu
            20

<210> SEQ ID NO 84
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Thr Ala Ser Glu Phe Thr Leu Asp Tyr His Ser Ile Gly Trp Phe
1               5                   10                  15

Arg Gln Ala Pro Gly Lys Glu Arg
            20

<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Ala Ala Ser Gly Arg Ala Phe Ser Val Tyr Ala Val Gly Trp Tyr
1               5                   10                  15

Arg Gln Pro Pro Gly Lys Gln Arg
            20

<210> SEQ ID NO 86
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Glu Val Ser Gly Ser Arg Gly Ser Ile Tyr Phe Ser Gly Trp Tyr
1               5                   10                  15

Arg Gln Ala Pro Gly Lys Gln Arg
            20

<210> SEQ ID NO 87
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Val Ala Ser Gly Ser Met Phe Asn Phe Tyr Gly Met Ala Trp Tyr
1               5                   10                  15

Arg Gln Ala Pro Gly Lys Gln Arg
            20
```

```
<210> SEQ ID NO 88
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Thr Phe Ser Gly Leu Tyr Leu His Ser Ser Ala Phe Gly Trp Phe
1               5                   10                  15

Pro His Val Pro Arg Glu Ala Arg
            20

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Val Ala Ala Ile Tyr Thr Asp Asp Thr Asp Asp Ser Ser Pro Ile
1               5                   10                  15

Tyr Ala Thr Ser Ala
            20

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met Val Ala Ala Ile Ser Ser Gly Gly Asn Thr Lys Tyr Ser Asp Ser
1               5                   10                  15

Val

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Val Ala Gly Ile Asn Met Ile Ser Ser Thr Lys Tyr Ile Asp Ser
1               5                   10                  15

Val

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Leu Val Ala Ala Ile Thr Ser Gly Gly Ser Thr Asn Tyr Ala Asp Ser
```

```
1               5                   10                  15
Val

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Leu Val Ala Gln Leu Met Ser Asp Gly Thr Ala Asn Tyr Gly Asp Ser
1               5                   10                  15
Val

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Val Ser Cys Ile Ser His Asn Gly Gly Thr Thr Asn Tyr Ala Asp
1               5                   10                  15
Ser Val

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Lys Ile Ser Cys Ile Ser Ser Thr Gly Asp Ser Thr Asn Tyr Asp Asp
1               5                   10                  15
Ser Val

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Val Ser Phe Ile Asn Thr Ser Asp Asp Val Thr Tyr Phe Ala Asp
1               5                   10                  15
Ser Val

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97
```

```
Trp Ile Ser Thr Ile Tyr Ser Asn Gly His Thr Tyr Ser Ala Asp Ser
1               5                   10                  15

Val

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Ile Ser Ser Ile Tyr Ser Asn Gly His Thr Tyr Ser Ala Asp Ser
1               5                   10                  15

Val

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Trp Ile Ser Gly Ile Gly Thr Ser Gly Thr Gly Arg Tyr Ala Ser
1               5                   10                  15

Ser Val

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Val Ser Gly Ile Asn Ser Gly Gly Gly Arg Thr Tyr Tyr Ala Asp
1               5                   10                  15

Ser Val

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Val Ser Tyr Val Asn Asn Asn Gly Met Thr Asn Tyr Ala Asp Ser
1               5                   10                  15

Val

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102
```

```
Gly Val Ser Cys Ile Ser Tyr Gly Asp Gly Thr Thr Phe Tyr Thr Asp
1               5                   10                  15

Ser Val

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Val Ala Ser Ile Thr Asp Gly Gly Ser Thr Asn Tyr Ala Asp Ser
1               5                   10                  15

Val

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Val Ala Ser Ile Thr Ser Gly Gly Thr Thr Asn Tyr Ala Asp Ser
1               5                   10                  15

Val

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Val Ala Ser Ile Asp Ser Glu Gly Arg Thr Thr Asn Tyr Pro Asp
1               5                   10                  15

Ser Leu

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Val Ala Phe Leu Cys Asn Ser Gly Ser Asp Pro Ile Tyr Leu His
1               5                   10                  15

Pro Glu

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 107

Arg Phe Thr Ile
1

<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Val Thr Ile
1

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Phe Ser Ile
1

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Phe Thr Ala
1

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Phe Thr Val
1

<210> SEQ ID NO 112
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ile Phe Thr Leu
1

<210> SEQ ID NO 113
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 113

Gln Asp Lys Asp Lys Asn Ala Val Tyr Leu Gln Met Asn Ser Pro Lys
1               5                   10                  15

Pro Glu Asp

<210> SEQ ID NO 114
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Asp Asn Asp Lys Asn Thr Met Tyr Leu Gln Met Asn Ser Leu Lys
1               5                   10                  15

Pro Glu Asp

<210> SEQ ID NO 115
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Asp Asn Ala Lys Asn Thr Val Tyr Leu Gln Met Asn Ser Leu Lys
1               5                   10                  15

Pro Glu Asp

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Asp Asp Val Asp Thr Thr Val His Leu Arg Met Asn Thr Leu Gln
1               5                   10                  15

Pro Ser Asp

<210> SEQ ID NO 117
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Asp Asn Ala Lys Asn Thr Val Tyr Leu Gln Met Asn Gly Leu Lys
1               5                   10                  15

Pro Glu Asp

<210> SEQ ID NO 118
<211> LENGTH: 19
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Asp Thr Ala Lys Ser Thr Val Phe Leu Gln Met Asn Asn Leu Ile
1               5                   10                  15

Pro Glu Asp

<210> SEQ ID NO 119
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Asp Asn Ser Lys Asn Thr Val Tyr Leu Gln Met Asn Val Leu Lys
1               5                   10                  15

Pro Glu Asp

<210> SEQ ID NO 120
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Asp Asn Ala Asn Asn Thr Leu Tyr Leu Gln Met Asn Ser Leu Lys
1               5                   10                  15

Pro Glu Asp

<210> SEQ ID NO 121
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Asp Asn Ala Lys Asn Thr Leu Tyr Leu Gln Met Ile Ser Leu Lys
1               5                   10                  15

Pro Glu Asp

<210> SEQ ID NO 122
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Asp Asn Ala Lys Asp Thr Leu Tyr Leu Gln Met Asp Ser Leu Lys
1               5                   10                  15

Pro Glu Asp

<210> SEQ ID NO 123

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Asp Asp Asp Lys Ala Thr Leu Tyr Leu Ser Met Asp Gly Leu Lys
1               5                   10                  15

Pro Glu Asp

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Asp Asn Ala Lys Asn Thr Met Tyr Leu Gln Met Asn Ser Leu Lys
1               5                   10                  15

Pro Glu Asp

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Asp Asn Ala Lys Asn Thr Val Thr Leu Gln Met Asn Ser Leu Lys
1               5                   10                  15

Pro Glu Asp

<210> SEQ ID NO 126
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Asp Asn Ala Arg Asn Thr Ala Tyr Leu Asp Met Asn Ser Leu Lys
1               5                   10                  15

Val Glu Asp

<210> SEQ ID NO 127
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Asp Asn Ala Lys Asn Thr Val Tyr Leu Gln Met Asn Ser Leu Lys
1               5                   10                  15

Pro Glu Asp
```

```
<210> SEQ ID NO 128
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Asp Asp Ala Lys Ser Thr Ala Tyr Leu Gln Met Asn Asn Leu Ile
1               5                   10                  15

Pro Asp Asp

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Arg His Cys Val Lys Thr Val Ser Pro Phe Glu Asp Asn Asp Thr Val
1               5                   10                  15

Glu His

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Arg Asp Asn Ala Lys Asn Thr Leu Tyr Leu Gln Met Asn Ser Leu Lys
1               5                   10                  15

Pro Glu Asp

<210> SEQ ID NO 131
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ala Arg Ala Phe Gly Gly Thr Trp Ser Leu Ser Ser Pro Asp Asp
1               5                   10                  15

Phe Ser Ala Trp Gly Gln Gly Thr Gln Val Thr Val Ser
            20                  25

<210> SEQ ID NO 132
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asn Leu Asp Thr Thr Met Val Glu Gly Val Glu Tyr Trp Gly Gln Gly
1               5                   10                  15

Thr Gln Val Thr Val Ser
```

20

<210> SEQ ID NO 133
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asn Ala Asp Gly Val Pro Glu Tyr Ser Asp Tyr Ala Ser Gly Pro Val
1               5                   10                  15

Tyr Trp Gly Gln Gly Thr Gln Val Thr Val Ser
            20                  25

<210> SEQ ID NO 134
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Tyr Ile His Thr Ser Arg Glu Ile Thr Trp Gly Arg Gly Thr Gln Val
1               5                   10                  15

Thr Val Ser Gln Gly Glu Ser Ser Ala Pro Gln Ser Ser Ala Pro Gln
            20                  25                  30

Ala Thr Val Ser
        35

<210> SEQ ID NO 135
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Gly Ala Arg Ser Gly Leu Cys Val Phe Phe Glu Leu Gln Asp Tyr
1               5                   10                  15

Asp Tyr Trp Gly Gln Gly Thr Gln Val Thr Val Ser
            20                  25

<210> SEQ ID NO 136
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gly Ala Asp Leu Leu Ala Arg Cys Gly Arg Val Trp Tyr Phe Pro Pro
1               5                   10                  15

Asp Leu Asn Tyr Arg Gly Gln Gly Thr Gln Val Thr Val Ser
            20                  25                  30

<210> SEQ ID NO 137
<211> LENGTH: 35
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 137

Ala Ala Val Arg Ser Pro Gly Pro Thr Gly Pro Ser Met Gln Pro Met
1               5                   10                  15

Trp Ser Val Pro Asp Leu Tyr Asp Tyr Trp Gly Gln Gly Thr Gln Val
            20                  25                  30

Thr Val Ser
        35

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Leu Thr Gly Glu Thr His Arg Gly Gln Gly Thr Gln Val Thr Val
1               5                   10                  15

Ser

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Lys Leu Val Gly Glu Thr His Arg Gly Gln Gly Thr Gln Val Thr Val
1               5                   10                  15

Ser

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Leu Thr Gly Glu Thr Tyr Arg Gly Gln Gly Thr Gln Val Thr Val
1               5                   10                  15

Ser

<210> SEQ ID NO 141
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Thr Gly Gly Val Tyr Ser Ala Tyr Val Gln Pro Arg Gly Lys Gly
1               5                   10                  15

Thr Gln Val Thr Val Ser
            20

```
<210> SEQ ID NO 142
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Val Arg Phe Thr Val Lys Thr Pro Gln Gly Tyr Tyr Leu Asn Asp
1               5                   10                  15

Phe Asp Tyr Trp Gly Gln Gly Thr Gln Val Thr Val Ser
            20                  25

<210> SEQ ID NO 143
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asn Val Ser Ala Tyr Thr Tyr Arg Ser Asn Tyr Tyr Pro Trp Gly
1               5                   10                  15

Gln Ala Asn His Val Thr Val Ser
            20

<210> SEQ ID NO 144
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ala Ala Ser Pro Gly Arg Leu Leu Leu Phe Arg Leu Cys Met Ser Glu
1               5                   10                  15

Asp Glu Tyr Asp Phe Trp Gly Gln Gly Thr Gln Val Thr Val Ser
            20                  25                  30

<210> SEQ ID NO 145
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asn Ala Asn Tyr Gly Gly Ser Val Leu Tyr Asn Tyr Trp Gly Pro Gly
1               5                   10                  15

Thr Gln Val Thr Val Ser
            20

<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 146

Asn Ile Gly Arg Tyr Gly Leu Gly Gly Ser Trp Gly Gln Gly Thr Gln
1               5                   10                  15

Val Thr Val Ser
            20

<210> SEQ ID NO 147
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asn Ala Phe Arg Gly Arg Met Tyr Asp Tyr Trp Gly Gln Gly Thr Gln
1               5                   10                  15

Val Thr Val Ser
            20

<210> SEQ ID NO 148
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Pro Thr His Leu Val Ile Thr His Pro Cys Ile Cys Ile Pro Ser Ala
1               5                   10                  15

Met Asp Tyr Arg Gly Lys Gly Thr Leu Val Pro Leu Ser
            20                  25

<210> SEQ ID NO 149
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Thr Asn Glu Val Cys Lys Trp Pro Pro Arg Pro Cys Gly Arg Arg
1               5                   10                  15

Cys Ala Gly Ala
            20

<210> SEQ ID NO 150
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser His His Ser Glu Asp Pro Gly Pro Arg Gly Leu Ala Ala Ala Gly
1               5                   10                  15

Ala Pro

<210> SEQ ID NO 151
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 151

Ser Glu Pro Lys Thr Pro Lys Pro Gln Gly Pro Arg Gly Leu Ala Ala
1               5                   10                  15

Ala Gly Ala Pro
            20

<210> SEQ ID NO 152
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Thr Glu Pro Lys Thr Pro Lys Pro Gln Gly Pro Arg Gly Leu Ala Ala
1               5                   10                  15

Ala Gly Ala Pro
            20

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Lys Pro Thr Thr Pro Lys Pro Arg Ala Pro Lys Ala Leu Arg Pro
1               5                   10                  15

Gln

<210> SEQ ID NO 154
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Ala His His Ser Glu Asp Pro Gly Pro Arg Gly Leu Ala Ala Ala
1               5                   10                  15

Gly Ala Pro

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Gln Arg Lys Thr Arg Lys Ala Gln Gly Arg Ala Arg Leu Ala Asp
1               5                   10                  15

Ala Gly Ala Pro
            20
```

```
<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Tyr Pro Asp Pro Leu Glu Pro
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Gly Ser Ala Gly Thr Ala Cys
1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Pro His Ala Asp Gln Met Glu Gln
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Pro Arg Cys Arg Ile Arg Phe
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Met Gln Ala Gln Lys Ala Gly
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 161

Met Gln Ala Gln Leu Ala Val
1               5

<210> SEQ ID NO 162
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Leu Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Thr Ala Ser
            20                  25                  30

Glu Phe Thr Leu Asp Tyr His Ser Ile Gly Trp Phe Arg Gln Ala Pro
        35                  40                  45

Gly Lys Glu Arg Glu Gly Val Ser Cys Ile Ser Tyr Gly Asp Gly Thr
    50                  55                  60

Thr Phe Tyr Thr Asp Ser Val Lys Gly Arg Phe Thr Ile Ser Arg Asp
65                  70                  75                  80

Asn Ala Lys Asn Thr Val Thr Leu Gln Met Asn Ser Leu Lys Pro Glu
                85                  90                  95

Asp Thr Ala Val Tyr Tyr Cys Ala Ala Ser Pro Gly Arg Leu Leu Leu
            100                 105                 110

Phe Arg Leu Cys Met Ser Glu Asp Glu Tyr Asp Phe Trp Gly Gln Gly
        115                 120                 125

Thr Gln Val Thr Val Ser Ser Glu Pro Lys Thr Pro Lys Pro Gln Gly
    130                 135                 140

Pro Arg Gly Leu Ala Ala Ala Gly Ala Pro Val Pro Tyr Pro Asp Pro
145                 150                 155                 160

Leu Glu Pro Arg Ala Ala
                165
```